United States Patent
Hamrah et al.

(10) Patent No.: US 9,931,031 B2
(45) Date of Patent: Apr. 3, 2018

(54) MEIBOMIAN GLAND DYSFUNCTION

(71) Applicant: Massachusetts Eye & Ear Infirmary, Boston, MA (US)

(72) Inventors: Pedram Hamrah, Wellesley, MA (US); Yureeda Qazi, Boston, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 647 days.

(21) Appl. No.: 14/379,360

(22) PCT Filed: Feb. 21, 2013

(86) PCT No.: PCT/US2013/027177
§ 371 (c)(1),
(2) Date: Aug. 18, 2014

(87) PCT Pub. No.: WO2013/126599
PCT Pub. Date: Aug. 29, 2013

(65) Prior Publication Data
US 2015/0038851 A1 Feb. 5, 2015

Related U.S. Application Data

(60) Provisional application No. 61/601,357, filed on Feb. 21, 2012.

(51) Int. Cl.
| | | |
|---|---|---|
| A61K 38/00 | (2006.01) | |
| A61B 3/10 | (2006.01) | |
| A61K 31/65 | (2006.01) | |
| A61K 31/7052 | (2006.01) | |
| G02B 21/00 | (2006.01) | |
| A61B 3/13 | (2006.01) | |
| A61B 5/00 | (2006.01) | |

(52) U.S. Cl.
CPC ............ *A61B 3/101* (2013.01); *A61B 3/1025* (2013.01); *A61B 5/44* (2013.01); *A61K 31/65* (2013.01); *A61K 31/7052* (2013.01); *A61B 3/13* (2013.01); *A61B 5/0071* (2013.01); *G02B 21/0028* (2013.01)

(58) Field of Classification Search
None
See application file for complete search history.

(56) References Cited

U.S. PATENT DOCUMENTS

| | | |
|---|---|---|
| 6,455,583 B1 | 9/2002 | Pflugfelder et al. |
| 6,726,680 B1 | 4/2004 | Knopp et al. |
| 7,760,927 B2 | 7/2010 | Gholap et al. |
| 7,864,996 B2 | 1/2011 | Hemmer et al. |
| 2006/0188140 A1 | 8/2006 | Gholap et al. |
| 2007/0103693 A1 | 5/2007 | Everett et al. |
| 2007/0206275 A1 | 9/2007 | Hemmer et al. |
| 2010/0057059 A1 | 3/2010 | Makino |
| 2010/0183587 A1 | 7/2010 | Dana et al. |
| 2011/0200242 A1 | 8/2011 | Takama et al. |
| 2011/0274322 A1 | 11/2011 | Kern et al. |
| 2013/0226008 A1 | 8/2013 | Dana et al. |
| 2013/0336557 A1 | 12/2013 | Cruzat et al. |
| 2015/0038431 A1 | 2/2015 | Hamrah et al. |

FOREIGN PATENT DOCUMENTS

| | | |
|---|---|---|
| RU | 2330668 | 8/2008 |
| WO | 2013/126599 | 8/2013 |
| WO | 2013/126602 | 8/2013 |

OTHER PUBLICATIONS

Al-Arfaj et al., "Significant Narrowing of Corneal Blood Vessel Diameter—A Prominent Neovascular Alteration in Response to Topical Bevacizumab Therapy," PowerPoint presentation at ARVO 2008 (Apr. 27 to May 1, 2008), 30 pages.
Alarfaj et al., "Significant Narrowing of Corneal Blood Vessel Diameter—A Prominent Neovascular Alteration in Response to Topical Bevacizumab Therapy," Oasis, The Online Abstract Submission and Invitation System$^{SM}$, Control/Tracking No. 08-A-1311-ARVO (Dec. 6, 2007), 2 pages.
Alhatem, "Peripheral Antigen Presenting Cells Are Differentially Distributed in Normal and Inflamed Murine Corneas," ARVO 2012 Abstract.
Baniasadi et al., "In Vivo Confocal Microscopy for Paecilomyces Lilacinus and Candida Parapsilosis Fungal Keratitis," ARVO 2011 Abstract.
Baniasadi et al., "In Vivo Confocal Microscopy for Paecilomyces Lilacinus and Candida Parapsilosis Fungal Keratitis," ARVO 2011 Poster.
Benitez Del Castillo et al., "An in vivo confocal masked study on corneal epithelium and subbasal nerves in patients with dry eye," Invest Ophthalmol Vis Sci., 45(9):3030-3035 (2004).
Cavalcanti et al., "Contact Lens/Contact Lens solution Combinations Determine the Inflammatory Changes on the Ocular Surface: A Laser In Vivo Confocal Microscopy Study," Abstract (2012).
Cruzat et al., "Diminishment in the Subbasal Corneal Nerve Plexus is Associated with Increased Density of Epithelial Dendritic Cells: An In Vivo Confocal Microscopy Study in Patients with Infectious Keratitis" 2010 ARVO Poster.
Cruzat et al., "Diminishment in the Subbasal Corneal Nerve Plexus is Associated with Increased Density of Epithelial Dendritic Cells: An In Vivo Confocal Microscopy Study in Patients with Infectious Keratitis" 2010 ARVO Abstract.
Cruzat, "In Vivo Confocal Microscopy (IVCM) in Dry Eye: Corneal Epithelial Cell and Nerve Alterations," 2010 AAO Abstract.
Cruzat, "In Vivo Confocal Microscopy in Dry Eye: Corneal Epithelial Cell and Nerve Alterations," AAO 2010 Poster.
Cruzat, "In Vivo Confocal Microscopy in Dry Eye: Corneal Epithelial Cell and Nerve Alterations," AAO, Chicago Presentation (Oct. 16-19, 2010), 10 pages.
Cruzat et al., "Contralateral Clinically Unaffected Eyes of Patients with Unilateral Infectious Keratitis Demonstrate Subclinical Diminishment of Corneal Nerves and Increase Dendritic Cell Density," ARVO 2011 Abstract.

(Continued)

*Primary Examiner* — Jeanette Lieb
(74) *Attorney, Agent, or Firm* — Fish & Richardson P.C.

(57) ABSTRACT

Provided herein are methods of diagnosing meibomian gland dysfunction (MGD), determining the severity of meibomian gland dysfunction in a subject, evaluating efficacy of treatment of MGD in a subject, selecting a subject for treatment of MGD, and selecting a subject for participation in a clinical study.

6 Claims, 18 Drawing Sheets

(56) References Cited

OTHER PUBLICATIONS

Cruzat et al., "Contralateral Clinically Unaffected Eyes of Patients with Unilateral Infectious Keratitis Demonstrate Subclinical Diminishment of Corneal Nerves and Increase Dendritic Cell Density," ARVO 2011, 16 pages.

Cruzat et al., "Inflammation and the Nervous System: The Connection in the Cornea in Patients with Infectious Keratitis," Investigative Ophthalmology & Visual Science, 52(8):5136-5143 (2011).

Dastjerdi et al., "Corneal sensation and morphology of corneal nerves in herpes zoster ophthalmicus: an in vivo confocal microscopy study," 2007 Abstract, 1 page.

Dastjerdi et al., "Corneal Sensation and Morphology of Corneal Nerves in Herpes Zoster Ophthalmicus," PowerPoint presentation at ARVO 2007 (May 6-10, 2007), 22 pages.

Dastjerdi et al., "Disparate Corneal Nerve Alterations between the Two Eyes in Dry Eye Patients with Asymmetric Ocular Surface Manifestations: In Vivo Confocal Microscopy Study," Oasis, The Online Abstract Submission and Invitation System[SM], Control/Tracking No. 08-A-3724-ARVO (Dec. 6, 2007), 2 pages.

Dastjerdi et al., "Disparate Corneal Nerve Changes among Fellow Eyes of Patients with Asymmetric Dry Eye Disease: In Vivo Confocal Microscopy Study," Oasis, The Online Abstract Submission and Invitation Systems[SM], Control/Tracking No. 08-PP-30019585-AAO (Apr. 9, 2008), 2 pages.

Ghafournian et al., "In Vivo Confocal Microscopy Study of Epithelial Cell Changes and Nerve Alterations in Patients with Dry Eye Syndrome," Poster (2009).

Ghafournian et al., "In Vivo Confocal Microscopy Study of Epithelial Cell Changes and Nerve Alterations in Patients with Dry Eye Syndrome," Abstract (2009).

Hamrah et al., "Novel Characterization of MHC Class II-Negative Population of Resident Corneal Langerhans Cell-Type Dendritic Cells," Invest. Ophthalmol. Vis. Sci. 43:639-646 (2002).

Hamrah et al., "The Corneal Stroma is Endowed with a Significant Number of Resident Dendritic Cells," Invest. Ophthalmol. Vis. Sci., 44:581-589 (2003).

Hamrah et al., "Alterations in Corneal Stromal Dendritic Cell Phenotype and Distribution in Inflammation," Arch. Ophthalmol., 121:1132-1140 (2003).

Hamrah et al., "Comparison of Corneal Nerve Alterations and Corneal Sensitivity in Herpes Simplex Keratitis with In Vivo Confocal Microscopy," ARVO Abstract, Control #07-A-4430-ARVO (Dec. 20, 2006), 3 pages.

Hamrah et al., "#774 Comparison of Corneal Nerve Alterations and Corneal Sensitivity in Herpes Simplex Keratitis with In Vivo Confocal Microscopy," ARVO 2007 Poster.

Hamrah et al., "Deletion of Chemokine Receptor CCR1 Prolongs Corneal Survival," Invest. Ophthalmol. Vis. Sci., 48:1228-1236 (2007).

Hamrah et al., "Cellular Changes of the Cornea in Herpes Zoster Ophthalmicus: An In Vivo Confocal Microscopy Study," ARVO Abstract, Control/Tracking No. 08-A-2436-ARVO (2007), 2 pages.

Hamrah et al., "Cellular Changes of the Cornea in Herpes Zoster Ophthalmicus: An In Vivo Confocal Microscopy Study," ARVO 2008 Presentation (Apr. 27 to May 1, 2008), 24 pages.

Hamrah et al., "Cellular Changes of the Cornea in Herpes Zoster Ophthalmicus: An In Vivo Confocal Microscopy Study," ARVO 2008 Abstract.

Hamrah et al., "Corneal Epithelial and Stromal Changes in Patients with Herpes Simplex Keratitis: an In Vivo Confocal Microscopy Study," Abstract, Control/Tracking No. 09-A-977-ARVO (Nov. 27, 2008), 2 pages.

Hamrah et al., "Corneal Epithelial and Stromal Changes in Patients with Herpes Simplex Keratitis: an In Vivo Confocal Microscopy Study" ARVO 2009 Abstract.

Hamrah et al., "Corneal Epithelial and Stromal Changes in Patients with Herpes Simplex Keratitis: an In Vivo Confocal Microscopy Study #2389," ARVO 2009 Poster.

Hamrah, "In Vivo Confocal Microscopy of the Cornea in Health and Disease," Harvard Medical School Presentation 2009, 48 pages.

Hamrah, "In Vivo Imaging and Quantification of Corneal Inflammation," WOC 2010, Berlin, Germany, 5 pages.

Hamrah et al., Visualization of Corneal Antigen-Presenting Cell Migration by Multi-Photon Intravital Microscopy (2010), 32 pages.

Hamrah, "In Vivo Imaging of Corneal Nerves," New Frontiers in Corneal Research Presentation, May 2010, 89 pages.

Hamrah, "Corneal Imaging," University of Louisville Presentation, Sep. 17, 2010, 105 pages.

Hamrah, "Immunobiology of Corneal Graft Rejection," Emory Eye Center Presentation Dec. 17, 2010, 110 pages.

Hamrah et al. "Antigen-Presenting Cells in the Eye and Ocular Surface," In Encyclopedia of the Eye, Oxford: Academic Press, 1:120-127 (2010).

Hamrah et al., "Corneal Sensation and Subbasal Nerve Alterations in Patients with Herpes Simplex Keratitis," Ophthalmology, 117:1930-1936 (2010).

Hamrah et al., "Physiologic Homeostasis and Turnover of Corneal Bone Marrow-Derived Cells: Lessons from the Parabiosis Model," ARVO 2011 Poster, 1 page.

Hamrah, "The Evolving Story of Corneal Antigen Presenting Cells: From Bench to Bedside," Duke Presentation Feb. 25, 2011, 121 pages.

Hamrah et al., "In vivo Imaging of Inflammatory Cell-Vessel Interactions at the Ocular Surface," ARVO 2011 Meeting (May 2011), 33 pages.

Hamrah, "Immuno-Imaging of the Ocular Surface: Studying Immune System Dynamics In Vivo," Duke Presentation May 18, 2011, 150 pages.

Hamrah, "An Explanation for Refractory Dry Eye Symptoms Despite Significant Improvement in Dry Eye Signs Post-Treatment for Meibomian Gland Dysfunction," AAOPT Abstract 2011.

Hamrah, "An Explanation for Refractory Dry Eye Symptoms Despite Significant Improvement in Dry Eye Signs Post-Treatment for Meibomian Gland Dysfunction," AAOPT Presentation, Oct. 2011, 38 pages.

Hamrah et al., "Cellular Changes of the Corneal Epithelium and Stroma in Herpes Simplex Keratitis: An In Vivo Confocal Microscopy Study," Ophthalmology, 119(9):1791-1797 (2012).

Hamrah et al., "Unilateral Herpes Zoster Ophthalmicus Results in Bilateral Corneal Nerve Alteration: An In Vivo Confocal Microscopy Study," Ophthalmology, 120(1):40-47 (2013).

Hoesl et al., "Cellular and Subbasal Nerve Alterations in Fuchs' Endothelial Dystrophy: An in vivo Confocal Microscopy Study," Abstract, ARVO (Nov. 28, 2008).

Hoesl et al., "Cellular and Subbasal Nerve Alterations in Fuchs' Endothelial Dystrophy: An in vivo Confocal Microscopy Study," ARVO 2009 Poster.

Hu et al., "Conjunctival in vivo confocal scanning laser microscopy in patients with atopic keratoconjunctivitis," Molecular Vision, 13:1379-89 (2007).

Hu et al., Infection of the Cornea with Herpes Simplex Virus-1 Results in Immediate Destruction of Subbasal Corneal Nerves and Increased Density and Maturation of Corneal Antigen-Presenting Cell, ARVO 2011 Abstract.

Hu et al., Infection of the Cornea with Herpes Simplex Virus-1 Results in Immediate Destruction of Subbasal Corneal Nerves and Increased Density and Maturation of Corneal Antigen-Presenting Cell, ARVO 2011 Poster.

International Search Report and Written Opinion for App. Ser. No. PCT/US2013/027181, dated Jun. 20, 2013, 8 pages.

Kurbanyan et al., "Corneal Nerve Alterations in Acute Acanthamoeba and Fungal Keratitis: An in vivo Confocal Microscopy Study," ARVO 2009 Abstract.

Kurbanyan et al., "#D709 Corneal Nerve Alterations in Acute Acanthamoeba and Fungal Keratitis: An in Vivo Confocal Microscopy Study," ARVO 2009 Poster.

Kurbanyan et al., "Corneal Nerve Alterations in Acute Acanthamoeba and Fungal Keratitis: An in Vivo Confocal Microscopy Study," Eye, 26:126-132 (2012), Epub Nov. 11, 2011.

(56) References Cited

OTHER PUBLICATIONS

Le et al., "In Vivo Confocal Microscopy of Long-standing Mixed-form Vernal Keratoconjunctivitis," Ocular Immunology & Inflammation, 18(5):349-351 (2010).
Le et al., "In vivo laser scanning confocal microscopy of vernal keratoconjunctivitis," Clinical and Experimental Ophthalmology, 39:53-60 (2011).
Lee et al., "In Vivo Confocal Microscopy in Diagnosis and Management of Acanthamoeba Keratitis Improves Patient Outcome," ARVO 2010 Abstract.
Lee et al., "In Vivo Confocal Microscopy in Diagnosis and Management of Acanthamoeba Keratitis Improves Patient Outcome," ARVO 2010 Poster.
Lee et al., "Diagnosis and Management of Acanthamoeba Keratitis by In Vivo Confocal Microscopy Improves Outcomes," ARVO 2010, 14 pages.
Lee et al., "Diagnosis and Management of Acanthamoeba Keratitis by in Vivo Confocal Microscopy Improves Outcomes," ARVO 2010 Abstract.
Mantopoulos et al., "P- and E-Selectins Mediate Dendritic Cell Homing to the Cornea," ARVO 2010 Abstract.
Mantopoulos et al., "P- and E-Selectins Mediate Dendritic Cell Homing to the Cornea," ARVO 2010 Poster.
Qazi et al., "Early Effects of Contact Lens Wear on Immune Cell Density of the Ocular Surface: Preliminary Results of a Laser In Vivo Confocal Microscopy Study," ARVO 2011 Abstract.
Qazi et al., "Early Effects of Contact Lens Wear on Immune Cell Density of the Ocular Surface: Preliminary Results of a Laser In Vivo Confocal Microscopy Study," ARVO 2011 Poster.
Schneider, "The Appearance of Hyper-Reflective Superficial Epithelial Cells Observed Using in vivo Confocal Microscopy," A thesis presented to the University of Waterloo. Waterloo, Ontario, Canada, 2010. Retrieved from the Internet: <URL: http://libdspace.uwaterloo.ca/4983/1/Schneider_Simone.pdf> abstract, pp. 41, 185, 207.
Schrems et al., "In Vivo Confocal Microscopy Comparison of the Anterior Human Corneal Structures by Laser Scanning and White Light Systems in Normal Diseased Corneas," ARVO 2009 Poster.
Shahatit et al., "#D975 In Vivo Morphology of Corneal Nerves in Patients with Corneal Allodynia," ARVO 2009 Poster.
Shahatit et al., In Vivo Morphology of Corneal Nerves in Patients with Corneal Allodynia, ARVO 2009 Abstract.
Turhan et al., "Dendritic Cell Recruitment to the Cornea is Differentially Regulated in Steady State and Inflammation," ARVO 2011 Meeting Abstract.
Turhan et al., "Dendritic Cell Recruitment to the Cornea is Differentially Regulated in Steady State and Inflammation," ARVO 2011 Poster.
Yamagami et al., "Distinct populations of dendritic cells in the normal human donor corneal epithelium," Invest Ophthalmol Vis Sci., 46(12):4489-4494 (2005).
Zheng et al., "Identification of Novel Subsets of Plasmacytoid and Conventional Dendritic Cells in the Cornea," ARVO 2010 Meeting Poster.
Zheng et al., "Identification of Novel Subsets of Plasmacytoid and Conventional Dendritic Cells in the Cornea," ARVO 2010 Meeting Abstract.
Office Action issued in U.S. Appl. No. 13/971,609 dated Dec. 2, 2014, 79 pages.

Notice of Allowance issued in U.S. Appl. No. 13/971,609 dated Jul. 8, 2015, 13 pages.
You et al., "Laser in Vivo Confocal Microscopy Demonstrates a Lower Density of Peripheral Corneal Nerve Fibers Compared to the Central Cornea in Normal Subjects," Investigative Ophthalmology & Visual Science Jun. 2013, vol. 54, 531, Abstract, 1 page.
Colon et al., "Morphologic Dendritic Immune Cells Parameters Reveal Differential Characteristics between the Central and Peripheral Cornea: an In Vivo Confocal Microscopy Normative Data," Investigative Ophthalmology & Visual Science Jun. 2013, vol. 54, 2063, Abstract, 1 page.
Cavalcanti et al., "In Vivo Confocal Microscopy Demonstrates Bilateral Increase in Epithelial Corneal Dendritic Immune Cells in Unilateral Herpes Zoster Ophthalmicus," Investigative Ophthalmology & Visual Science Jun. 2013, vol. 54, 2159, Abstract, 1 page.
Hamrah et al., "An explanation for refractory dry eye symptoms despite significant improvement in dry eye signs post-treatment for meibomian gland dysfunction (MGD)," American Academy of Optometry, Program No. 110010, Oct. 2011, Abstract, 1 page.
Qazi et al., "Immune Response in Meibomian Gland Dysfunction (MGD) and the Effect of Anti-Inflammatory Therapy: An In Vivo Confocal Microscopy (IVCM) Study," Investigative Ophthalmology & Visual Science Mar. 2012, vol. 53, 593, Poster, 1 page.
Colon et al, "In Vivo Confocal Microscopy of the Immune Cells in the Cornea of Normal Subjects Demonstrates Irregular Peripheral Distribution of Dendritic Cells," Investigative Ophthalmology & Visual Science Mar. 2012, vol. 53, 94, Poster, 1 page.
Williams et al., "In Vivo Confocal Microscopy as a Tool to Evaluate Cellular Changes in the Cornea and Conjunctiva in Ocular Allergy and Non-Allergic Ocular Inflammatory Diseases," Conjunctiva: Biology and Pathophysiology, May 8, 2012, Poster, 1 page.
Hamrah et al., "An Explanation for Refractory Dry Eye Symptoms Despite Significant Improvement in Dry Eye Signs Post-Treatment for Meibomian Gland Dysfunction," American Academy of Optometry, Program No. 110010, Oct. 2011, Poster, 1 page.
Yao et al., "Dry Eye Syndrome: An Update in Office Management," Am. J. Med. 124:1016-1018, 2011.
Girish et al., "Affordable image analysis using NIH Image/ImageJ," Indian J. Cancer 41(1):47, 2004.
Meijering et al., "Design and validation of a tool for neurite tracing and analysis in fluorescence microscopy images," Cytometry Part A, 58A(2):167-176, Apr. 2004.
Oliveira-Soto and Efron, "Morphology of corneal nerves using confocal microscopy," Cornea 20(4):374-384, May 2001.
Ibrahim et al., "The efficacy, sensitivity, and specificity of in vivo laser confocal microscopy in the diagnosis of meibomian gland dysfunction," Ophthalmology, 117(4):665-672, Apr. 2010.
Geerling et al., "The International Workshop on Meibomian Gland Dysfunction: Report of the Subcommittee on Management and Treatment of Meibomian Gland Dysfunction," Investigative Ophthalmology & Visual Science, 52(4):2050-2064 (Special Issue, 2011).
Asbell et al., "The International Workshop on Meibomian Gland Dysfunction: Report of the Clinical Trials Subcommittee," Investigative Ophthalmology & Visual Science, 52(4):2065-2085 (Special Issue, 2011).
International Search Report and Written Opinion issued in PCT/US2013/027177 dated Jul. 11, 2013 (8 pages).
Em et al., "In vivo confocal microscopy in blepharitis," Klin Monbl Augenheilkd, 222(11):894-900 (2005) (Abstract).
International Preliminary Report on Patentability issued in PCT/US2013/027177 dated Aug. 26, 2014 (6 pages).

Study Design

MEIBOMIAN GLAND DYSFUNCTION

CLAIM OF PRIORITY

This application is the U.S. national stage under 35 U.S.C. § 371 of International Patent Application No. PCT/US2013/027177, filed on Feb. 21, 2013, which claims priority to U.S. Provisional Patent Application Ser. No. 61/601,357, filed on Feb. 21, 2012. The entire contents of the foregoing are hereby incorporated by reference.

FEDERALLY SPONSORED RESEARCH

This invention was made with Government support under grant number NIH K12-EY016335 and NIH K08-EY020575 awarded by the National Institutes of Health. The Government has certain rights in the invention.

BACKGROUND OF THE INVENTION

Meibomian glands are specialized sebaceous glands in the eyelids that are responsible for producing meibum. Meibum is an oily substance that forms the outermost layer of the tear film slowing its evaporation. In humans, there are approximately 50 meibomian glands present in the upper eyelid, and approximately 25 meibomian glands in the lower eyelid.

Meibomian gland dysfunction (MGD) is generally described as a chronic, diffuse abnormality of the meibomian glands. MGD may result in an alteration of the tear film. MGD is thought to be a significant cause of dry eye disease throughout the world (Nichols et al., *Invest. Ophthalmol. Vis. Sci.* 52:1922-1929, 2011).

SUMMARY OF THE INVENTION

The invention is based, at least in part, on the discovery that subjects with meibomian gland dysfunction (MGD) have one or more of: an elevation in the number and/or density of immune cells in the palpebral conjunctival epithelium, an elevation in the number and/or density of immune cells in the palpebral conjunctival substantia propria, an elevation in the number, area, and/or density of immune cells present within one or more ducts/ductules of meibomian gland(s) and/or around one or more meibomian glands, an elevation in the level of glandular/ductal obstruction of one or more meibomian gland(s), and an elevation in the size of one or more ducts/ductules of one or more meibomian gland(s) in one or both of the eyelids, as compared to an asymptomatic and clinically unremarkable, healthy control (e.g., a subject that does not have any dry eye symptoms or an eye disorder, e.g., a subject that does not have MGD). The invention is also based, in part, on the discovery that subjects with MGD that are successfully treated have one or more of: a decrease in the number and/or density of immune cells in the palpebral conjunctival epithelium, a decrease in the number and/or density of immune cells in the palpebral conjunctival substantia propria, a decrease in the number, area, and/or density of immune cells present within one or more ducts/ductules of one or more meibomian glands and/or one or more meibomian glands, a decrease in the level of glandular/ductal obstruction of one or more meibomian gland(s), and a decrease in the size of one or more ducts/ductules of one or more meibomian gland(s) in one or both of the eyelids, following or at a later time point in treatment as compared to a time point prior to treatment or an earlier time point in treatment.

In view of these discoveries, provided herein are methods of diagnosing an eyelid disorder (e.g., MGD) in a subject, methods of determining the severity of an eyelid disorder in a subject (e.g., MGD), methods of evaluating the efficacy of treatment in a subject having an eyelid disorder (e.g., MGD), methods of selecting a subject for treatment of an eyelid disorder (e.g., MGD), and methods of selecting a subject for participation in a clinical study. These methods include determining in an eyelid of a subject, or alternatively obtaining, providing, or using previously determined information regarding, (e.g., at one or more time points) one or more of: the number and/or density of immune cells in the palpebral conjunctival epithelium, the number and/or density of immune cells in the palpebral conjunctival substantia propria, the number, area, and/or density of immune cells present within one or more ducts/ductules in one or more meibomian glands and/or around one or more meibomian glands, the level of glandular/ductal obstruction of one or more meibomian gland(s), and the size of one or more ducts/ductules of one or more meibomian gland(s). Also provided are methods of treating a subject having an eyelid disorder (e.g., MGD) that include selectively orally administering to a subject (e.g., a subject having MGD) and determined to have an elevated number and/or density of immune cells in the palpebal conjunctival substantia propria as compared to a reference level, at least one anti-inflammatory antimicrobial agent, and/or selectively performing meibomian gland probing on the subject (e.g., a subject having MGD) determined to have an elevation in the level of glandular/ductal obstruction of one or more meibomian gland(s) as compared to a reference level. Also provided are methods of using at least one anti-inflammatory antimicrobial agent (e.g., formulated for oral administration) for treating a subject having an eyelid disorder (e.g., MGD) determined to have an elevated number and/or density of immune cells in the palpebral conjunctival substantia propria as compared to a reference level. Also provided herein are at least one anti-inflammatory antimicrobial agent (e.g., formulated for oral administration) for use in treating a subject having an eyelid disorder (e.g., MGD) determined to have an elevated number and/or density of immune cells in the palpebral conjunctival substantia propria as compared to a reference level and/or for use in the manufacture of a medicament for treatment of an eyelid disorder (e.g., MGD) (e.g., for treatment of a subject having an eyelid disorder (e.g., MGD) determined to have an elevated number and/or density of immune cells in the palpebral conjunctival substantia propria as compared to a reference level).

Provided herein are methods of diagnosing meibomian gland dysfunction (MGD) in a subject that include (a) determining in an eyelid of a subject, or alternatively obtaining, providing, or using previously determined information regarding, one or more of: (i) a number, area, and/or density of immune cells present within one or more ducts/ductules in one or more meibomian gland(s) and/or around one or more meibomian gland(s), (ii) a level of glandular/ductal obstruction in one or more meibomian gland(s), and (iii) a size of one or more ducts/ductules present in one or more meibomian gland(s); and (b) comparing the one or more of: (i) the number, area, and/or density of immune cells present within one or more ducts/ductules in one or more meibomian gland(s) and/or around one or more meibomian glands, (ii) the level of glandular/ductal obstruction in one or more meibomian gland(s), and (iii) the size of one or more ducts/ductules present in one or more meibomian gland(s), determined in the eyelid of the subject to one or more corresponding reference values, where one or more of: (i) an elevation in the number, area, and/or density of immune cells present within one or more ducts/ductules in one or more meibomian gland(s) and/or around one or more meibomian gland(s), (ii) an elevation in the level of glandular/ductal obstruction in one or more meibomian gland(s), and (iii) an elevation in the size of one or more ducts/ductules present in one or more meibomian gland(s) in the eyelid of the subject, compared to the one or more corresponding reference values, indicates that the subject has MGD; and optionally, further including (c) identifying a subject having in an eyelid one or more of: (i) an elevation in the number, area, and/or density of immune cells present within one or more ducts/ductules in one or more meibomian gland(s) and/or around one or more meibomian gland(s), (ii) an elevation in the level of glandular/ductal obstruction in one or more meibomian gland(s), and (iii) an elevation in the size of one or more ducts/ductules present in one or more meibomian gland(s), compared to the one or more corresponding reference values, as having MGD. In some embodiments, the determining in (a) is performed using in vivo confocal microscopy.

Some embodiments further include (c) determining, or alternatively obtaining, providing, or using previously determined information regarding, the number and/or density of immune cells in a palpebral conjunctival epithelium, and/or a number and/or density of immune cells in a palpebral conjunctival substantia propria in the eyelid of the subject; (d) comparing the number and/or density of immune cells in the palpebral conjunctival epithelium, and/or the number and/or density of immune cells in the palpebral conjunctival substantia propria determined in the eyelid of the subject, to one or more corresponding reference values, where one or more of an elevation in the number and/or density of immune cells in the palpebral conjunctival epithelium, and an elevation in the number and/or density of immune cells in the palpebral conjunctival substantia propria in the eyelid of the subject, compared to the one or more corresponding reference values, indicates that the subject has MGD, and optionally, including (e) further identifying a subject having in an eyelid one or more of an elevation in the number and/or density of immune cells in the palpebral conjunctival epithelium, and an elevation in the number and/or density of immune cells in the palpebral conjunctival substantia propria, compared to the one or more corresponding reference values, as having MGD. In some embodiments, the determining in (c) is performed using in vivo confocal microscopy.

In some embodiments, the one or more of the reference values are threshold values. In some embodiments, the one or more of the reference values is selected from the group consisting of: (i) the number, area, and/or density of immune cells present within one or more ducts/ductules in one or more meibomian gland(s) and/or around one or more meibomian glands, (ii) the level of glandular/ductal obstruction in one or more meibomian gland(s), and (iii) the size of one or more ducts/ductules present in one or more meibomian gland(s), determined in (or recorded or previously observed for) an eyelid of a healthy subject. In some embodiments, the one or more of the reference values is selected from the group consisting of the number and/or density of immune cells in the palpebral conjunctival epithelium, and the number and/or density of immune cells in the palpebral conjunctival substantia propria, determined in (or recorded or previously observed for) an eyelid of a healthy subject. In some embodiments, the reference value is determined in a cohort of reference subjects. In some embodiments, the reference value is statistically determined in a cohort of reference subjects, e.g., is the median, mean, or a percentile (e.g., tertile, quartile, quintile) cut-off value (e.g., the top percentile, e.g., top tertile, quartile, or quintile cut-off value) in a cohort of reference subjects.

In some embodiments, the subject is not diagnosed as having an allergy or does not have allergy. In some embodiments, the subject is not diagnosed as having atopic keratoconjunctivitis or vernal conjunctivitis, or does not have atopic keratoconjunctivitis or vernal conjunctivitis. Some embodiments further include assessing, or alternatively obtaining, providing, or using previously determined information regarding, one or more additional symptoms of MGD in the subject. Some embodiments further include determining, or alternatively obtaining, providing, or using previously determined information regarding, the tear break-up time in an eye of the subject and/or performing, or alternatively obtaining, providing, or using previously determined information regarding, corneal fluorescein staining in an eye of the subject.

Also provided are methods of evaluating efficacy of a treatment in a subject having meibomian gland dysfunction (MGD) that include: (a) determining in an eyelid of a subject having MGD, or alternatively obtaining, providing, or using previously determined information regarding, one or more of (i) a number, area, and/or density of immune cells present within one or more ducts/ductules in one or more meibomian gland(s) and/or around one or more meibomian glands, (ii) a level of glandular/ductal obstruction in one or more meibomian gland(s), and (iii) a size of one or more ducts/ductules present in one or more meibomian gland(s) at a first time point; (b) determining in the eyelid of the subject, or alternatively obtaining, providing, or using previously determined information regarding, one or more of (i) the number, area, and/or density of immune cells present within one or more ducts/ductules in one or more meibomian gland(s) and/or around one or more meibomian glands, (ii) the level of glandular/ductal obstruction in one or more meibomian gland(s), and (iii) the size of one or more ducts/ductules present in one or more meibomian gland(s) at a second time point; and (c) comparing the one or more of (i) the number, area, and/or density of immune cells present within one or more ducts/ductules in one or more meibomian gland(s) and/or around one or more meibomian glands, (ii) the level of glandular/ductal obstruction in one or more meibomian gland(s), and (iii) the size of one or more ducts/ductules present in one or more meibomian gland(s) determined at the first and second time points, where (i) the first time point is prior to treatment and the second time point is any time point following the initiation of treatment, or (ii) the first time point is following the initiation of treatment and the second time point is at a later time point during or after treatment; and one or more of (i) a decrease in the number, area, and/or density of immune cells present within one or more ducts/ductules of one or more meibomian glands, (ii) a decrease in the level of glandular/ductal obstruction in one or more meibomian gland(s), and (iii) a decrease in the size of one or more ducts/ductules present in one or more meibomian gland(s) determined at the second time point compared to the first time point indicates that the treatment was effective in the subject, and optionally (d) identifying the treatment administered to a subject having in an eyelid one or more of (i) a decrease in the number, area, and/or density of immune cells present within one or more ducts/ductules of one or more meibomian gland(s) and/or around one or more meibomian glands, (ii) a decrease in the level of glandular/ductal obstruction in one or more meibomian gland(s), and (iii) a decrease in the size of one or more ducts/ductules present in one or more meibomian gland(s) determined at the second time point compared to the first time point as being effective in the subject. In some embodiments, the determining in (a) and (b) is performed using in vivo confocal microscopy.

Some embodiments further include (d) determining in the eyelid of the subject, or alternatively obtaining, providing, or using previously determined information regarding, one or more of a number and/or density of immune cells in the palpebral conjunctival epithelium, and a number and/or density of immune cells in a palpebral conjunctival substantia propria at a first time point; (e) determining in the eyelid of the subject, or alternatively obtaining, providing, or using previously determined information regarding, one or more of a number and/or density of immune cells in a palpebral conjunctival epithelium, and a number and/or density of immune cells in a palpebral conjunctival substantia propria, at a second time point; and (f) comparing the one or more of the number and/or density of immune cells in the palpebral conjunctival epithelium, and the number and/or density of immune cells in the palpebral conjunctival substantia propria, determined at the first and second time points, where one or more of a decrease in the number and/or density of immune cells in the palpebral conjunctival epithelium, and a decrease in the number and/or density of immune cells in the palpebral conjunctival substantia propria, determined at the second time point compared to the first time point further indicates that the treatment was effective in the subject, and optionally, (g) further identifying the treatment administered to a subject having in an eyelid one or more of a decrease in the number and/or density of immune cells in the palpebral conjunctival epithelium, and a decrease in the number and/or density of immune cells in the palpebral conjunctival substantia propria, determined at the second time point compared to the first time point, as being effective in the subject. In some embodiments, the determining in (d) and (e) is performed using in vivo confocal microscopy.

Some embodiments further include assessing, or alternatively obtaining, providing, or using previously determined information regarding, one or more additional symptoms of MGD in the subject at the first and/or second time point. Some embodiments further include determining, or alternatively obtaining, providing, or using previously determined information regarding, the tear break-up time in an eye of the subject and/or performing, or alternatively obtaining, providing, or using previously determined information regarding, corneal fluorescein staining in an eye of the subject at the first and/or second time point. In some embodiments, the first and the second time point are at least one week apart. In some embodiments, the subject is not diagnosed as having an allergy or does not have allergy. In some embodiments, the subject is not diagnosed as having atopic keratoconjunctivitis or vernal conjunctivitis, or does not have atopic keratoconjunctivitis or vernal conjunctivitis.

Also provided are methods of treating a subject having meibomian gland dysfunction (MGD) that include selectively orally or topically administering to a subject having MGD and determined to have an elevated number and/or density of immune cells in the palpebral conjunctival substantia propria as compared to a reference level, at least one anti-inflammatory antimicrobial agent, and/or selectively performing meibomian gland probing on a subject having MGD, determined to have an elevation in the level of glandular/ductal obstruction in one or more meibomian gland(s) compared to a reference level. Also provided are methods of using at least one anti-inflammatory antimicrobial agent (e.g., formulated for oral or topical administration) for treating a subject having MGD determined to have an elevated number and/or density of immune cells in the palpebral conjunctival substantia propria as compared to a reference level. Also provided are at least one anti-inflammatory antimicrobial agent (e.g., formulated for oral or topical administration) for use in treating a subject having MGD determined to have an elevated number and/or density of immune cells in the palpebral conjunctival substantia propria as compared to a reference level and/or for use in the manufacture of a medicament for treating a subject a subject as described herein (e.g., for treating a subject having MGD determined to have an elevated number and/or density of immune cells in the palpebral conjunctival substantia propria as compared to a reference level). In some embodiments, the anti-inflammatory antimicrobial agent is selected from the group consisting of: azithromycin, doxycycline, clarithromycin, dirithromycin, erythromycin, roxithromycin, telithromycin, carbomycin A, josamycin, kitasamycin, midecamycin, oleandomycin, solithomycin, spiramycin, troleandomycin, tylocine, and rapamycin. In some embodiments, the anti-inflammatory antimicrobial agent is doxycycline or azithromycin.

Some embodiments further include determining, or alternatively obtaining, providing, or using previously determined information regarding, a number and/or density of immune cells in a palpebral conjunctival substantia propria of the subject and/or a level of glandular/ductal obstruction in one or more meibomian gland(s) in the subject; and comparing the number and/or density of immune cells in the palpebral conjunctival substantia propria and/or the level of glandular/ductal obstruction in one or more meibomian gland(s) in the subject to a corresponding reference value. In some embodiments, the determining is performed using in vitro confocal microscopy.

Some embodiments further include selecting a subject determined to have an elevated number and/or density of immune cells in the palpebral conjunctival substantia propria and/or an elevated level of glandular/ductal obstruction in one or more meibomian glands as compared to the corresponding reference value.

Also provided are methods of selecting a subject for treatment of meibomian gland dysfunction that include: (a) determining in an eyelid of a subject, or alternatively obtaining, providing, or using previously determined information regarding, one or more of (i) a number, area, and/or density of immune cells present within one or more ducts/ductules in one or more meibomian gland(s) and/or around one or more meibomian glands, (ii) a level of glandular/ductal obstruction in one or more meibomian gland(s), and (iii) a size of one or more ducts/ductules present in one or more meibomian gland(s); (b) comparing the one or more of (i) the number, area, and/or density of immune cells present within one or more ducts/ductules in one or more meibomian gland(s) and/or around one or more meibomian glands, (ii) the level of glandular/ductal obstruction in one or more meibomian gland(s), and (iii) the size of one or more ducts/ductules present in one or more meibomian gland(s), determined in the eyelid of the subject to one or more corresponding reference values; and (c) selecting a subject having one or more of (i) an elevation in the number, area, and/or density of immune cells present within one or more ducts/ductules in one or more meibomian gland(s) and/or within one or more meibomian glands, (ii) an elevation in the level of glandular/ductal obstruction in one or more meibomian gland(s), and (iii) an elevation in the size of one or more ducts/ductules present in one or more meibomian gland(s), compared to the one or more corresponding reference values, for treatment of MGD. In some embodiments, the determining in (a) is performed using in vivo confocal microscopy.

Some embodiments further include (d) determining in the eyelid of the subject, or alternatively obtaining, providing, or using previously determined information regarding, one or more of a number and/or density of immune cells in the palpebral conjunctival epithelium, and a number and/or density of immune cells in a palpebral conjunctival substantia propria; (e) comparing the one or more of the number and/or density of immune cells in the palpebral conjunctival epithelium, and the number and/or density of immune cells in the palpebral conjunctival substantia propria, determined in the eyelid of the subject to one or more corresponding reference values; and (f) further selecting a subject having one or more of an elevation in the number and/or density of immune cells in the palpebral conjunctival epithelium, and an elevation in the number and/or density of immune cells in the palpebral conjunctival substantia propria, compared to the one or more corresponding reference values, for treatment of MGD. In some embodiments, the determining in (d) is performed using in vivo confocal microscopy.

In some embodiments, the one or more of the reference values are threshold values. In some embodiments, the one or more of the reference values is selected from the group consisting of: (i) the number, area, and/or density of immune cells present within one or more ducts/ductules in one or more meibomian gland(s) and/or around one or more meibomian glands, (ii) the level of glandular/ductal obstruction in one or more meibomian gland(s), and (iii) the size of one or more ducts/ductules present in one or more meibomian gland(s), determined in (or recorded or previously observed for) an eyelid of a healthy subject. In some embodiments, the one or more of the reference values is selected from the group consisting of: the number and/or density of immune cells in the palpebral conjunctival epithelium, and the number and/or density of immune cells in the palpebral conjunctival substantia propria, determined in (or recorded or previously observed for) an eyelid of a healthy subject.

Some embodiments further include assessing, or alternatively obtaining, providing, or using previously determined information regarding, one or more additional symptoms of MGD in the subject. Some embodiments further include determining, or alternatively obtaining, providing, or using previously determined information regarding, the tear break-up time in an eye of the subject and/or performing, or alternatively obtaining, providing, or using previously determined information regarding, corneal fluorescein staining in an eye of the subject. In some embodiments, the subject is not diagnosed as having an allergy or does not have an allergy. In some embodiments, the subject is not diagnosed as having atopic keratoconjunctivitis or vernal conjunctivitis, or does not have atopic keratoconjunctivitis or vernal conjunctivitis.

Also included are methods of selecting a subject for participation in a clinical study that include: (a) determining in an eyelid of a subject, or alternatively obtaining, providing, or using previously determined information regarding, one or more of (i) a number and/or density of immune cells in the palpebral conjunctival epithelium, (ii) a number and/or density of immune cells in the palpebral conjunctival substantia propria, (iii) a number, area, and/or density of immune cells present within one or more ducts/ductules in one or more meibomian gland(s) and/or within one or more meibomian glands, (iv) a level of glandular/ductal obstruction in one or more meibomian gland(s), and (v) a size of one or more ducts/ductules present in one or more meibomian gland(s); (b) comparing the one or more of (i) the number and/or density of immune cells in the palpebral conjunctival epithelium, (ii) the number and/or density of immune cells in the palpebral conjunctival substantia propria, (iii) the number, area, and/or density of immune cells present within one or more ducts/ductules in one or more meibomian gland(s) and/or around one or more meibomian glands, (iv) the level of glandular/ductal obstruction in one or more meibomian gland(s), and (v) the size of one or more ducts/ductules present in one or more meibomian gland(s), determined in the eyelid of the subject to one or more corresponding reference values; and (c) selecting a subject having one or more of (i) an elevation in the number and/or density of immune cells in the palpebral conjunctival epithelium, (ii) an elevation in the number and/or density of immune cells in the palpebral conjunctival substantia propria, (iii) an elevation in the number, area, and/or density of immune cells present within one or more ducts/ductules in one or more meibomian gland(s) and/or around one or more meibomian glands, (iv) an elevation in the level of glandular/ductal obstruction in one or more meibomian gland(s), and (v) an elevation in the size of one or more ducts/ductules present in one or more meibomian gland(s), compared to the one or more corresponding reference values for participation in a clinical study. In some embodiments, the determining in (a) is performed using in vivo confocal microscopy. In some embodiments, the reference values are threshold values. In some embodiments, the one or more of the reference values is selected from the group consisting of: (i) the number and/or density of immune cells in the palpebral conjunctival epithelium, (ii) the number and/or density of immune cells in the palpebral conjunctival substantia propria, (iii) the number, area, and/or density of immune cells present within one or more ducts/ductules in one or more meibomian gland(s) and/or around one or more meibomian glands, (iv) the level of glandular/ductal obstruction in one or more meibomian gland(s), and (v) the size of one or more ducts/ductules present in one or more meibomian gland(s), determined in (or recorded or previously observed for) the eyelid of a healthy subject.

Some embodiments further include assessing, or alternatively obtaining, providing, or using previously determined information regarding, one or more additional symptoms of MGD in the subject. Some embodiments further include determining, or alternatively obtaining, providing, or using previously determined information regarding, the tear break-up time in an eye of the subject and/or performing corneal fluorescein staining in an eye of the subject.

Also provided are methods of determining the severity of meibomian gland dysfunction (MGD) in a subject that include (a) determining in an eyelid of a subject, or alternatively obtaining, providing, or using previously determined information regarding, one or more of: (i) a number and/or density of immune cells present within one or more ducts/ductules in one or more meibomian gland(s), (ii) a level of glandular/ductal obstruction in one or more meibomian gland(s), and (iii) a size of one or more ducts/ductules present in one or more meibomian gland(s); and (b) comparing the one or more of: (i) the number and/or density of immune cells present within one or more ducts/ductules in one or more meibomian gland(s), (ii) the level of glandular/ductal obstruction in one or more meibomian gland(s), and (iii) the size of one or more ducts/ductules present in one or more meibomian gland(s), determined in the eyelid of the subject to one or more corresponding reference values, where one or more of: (i) an elevation in the number and/or density of immune cells present within one or more ducts/ductules in one or more meibomian gland(s), (ii) an elevation in the level of glandular/ductal obstruction in one or more meibomian gland(s), and (iii) an elevation in the size of one or more ducts/ductules present in one or more meibomian gland(s) in the eyelid of the subject, compared to the one or more corresponding reference values, indicates that the subject has a severe or advanced form of MGD, and optionally include (c) identifying a subject having in an eyelid one or more of (i) an elevation in the number and/or density of immune cells present within one or more ducts/ductules in one or more meibomian gland(s), (ii) an elevation in the level of glandular/ductal obstruction in one or more meibomian gland(s), and (iii) an elevation in the size of one or more ducts/ductules present in one or more meibomian gland(s), as compared to the one or more corresponding reference values, as having a severe or advanced form of MGD. In some embodiments, the determining in (a) is performed using in vivo confocal microscopy.

Some embodiments further include, (c) determining, or alternatively obtaining, providing, or using previously determined information regarding, the number and/or density of immune cells in a palpebral conjunctival epithelium, and/or a number and/or density of immune cells in a palpebral conjunctival substantia propria in the eyelid of the subject; (d) comparing the number and/or density of immune cells in the palpebral conjunctival epithelium, and/or the number and/or density of immune cells in the palpebral conjunctival substantia propria determined in the eyelid of the subject, to one or more corresponding reference values, where one or more of an elevation in the number and/or density of immune cells in the palpebral conjunctival epithelium, and an elevation in the number and/or density of immune cells in the palpebral conjunctival substantia propria in the eyelid of the subject, compared to the one or more corresponding reference values, indicates that the subject has a severe of advanced form of MGD, and optionally including (e) further identifying a subject having in an eyelid one or more of an elevation in the number and/or density of immune cells in the palpebral conjunctival epithelium, and an elevation in the number and/or density of immune cells in the palpebral conjunctival substantia propria, compared to the one or more corresponding reference values, as having a severe or advanced form of MGD. In some embodiments, the determining in (c) is performed using in vivo confocal microscopy. In some embodiments, one or more of the reference values are threshold values. In some embodiments, one or more of the reference values is selected from the group of: (i) the number and/or density of immune cells present within one or more ducts/ductules in one or more meibomian gland(s), (ii) the level of glandular/ductal obstruction in one or more meibomian gland(s), and (iii) the size of one or more ducts/ductules present in one or more meibomian gland(s), determined in (or recorded or previously observed for) an eyelid of a healthy subject or a subject having a low severity form of an eyelid disorder (e.g., MGD). In some embodiments, one or more of the reference values is selected from the group of the number and/or density of immune cells in the palpebral conjunctival epithelium, and the number and/or density of immune cells in the palpebral conjunctival substantia propria, determined in (or recorded or previously observed for) an eyelid of a healthy subject or a subject having a low severity form of an eyelid disorder (e.g., MGD).

In some embodiments, the subject is not diagnosed as having an allergy or does not have allergy. In some embodiments, the subject is not diagnosed as having atopic keratoconjunctivitis or vernal conjunctivitis, or does not have atopic keratoconjunctivitis or vernal conjunctivitis. Some embodiments further include assessing, or alternatively obtaining, providing, or using previously determined information regarding, one or more additional symptoms of MGD in the subject. Some embodiments further include determining, or alternatively obtaining, providing, or using previously determined information regarding, the tear breakup time in an eye of the subject and/or performing corneal fluorescein staining in an eye of the subject.

By the term "meibomian gland" is meant a specialized sebaceous gland present in the eyelid that produces and secretes meibum, an oily substance that retards or slows evaporation tears. Methods for detecting immune cells present within, around, or proximal to the meibomian gland, and methods for detecting immune cells and sub-anatomical structures present within meibomian glands and within the palpebral conjunctiva using in vivo confocal microscopy are described herein.

By the term "meibomian gland dysfunction" or "MGD" is meant an abnormality (e.g., a chronic abnormality) of meibomian gland function in the eyelid of a subject that results in meibomian gland obstruction, terminal duct obstruction, and/or a decrease (e.g., an observable, detectable, or significant decrease) in meibomian gland secretion. Non-limiting symptoms of MGD include but are not limited to dry eyes, and pain or a burning sensation in the eyes. MGD has a variety of different causes including, but not limited to, androgen deficiency, menopause, Sjogren's syndrome, and psoriasis. Methods of diagnosing, treating, and determining the efficacy of a treatment for MGD are provided herein.

By the term "glandular or ductal obstruction" is meant an alteration (e.g., a structural alteration, e.g., such as the change in the size or shape of a meibomian gland, a change in the size or shape of one or more meibomian gland acini and/or one or more meibomian gland ducts/ductules, complete or partial blockage in a meibomian gland duct, and complete or partial blockage in the orifice of a meibomian gland on the eyelid margin) in a meibomian gland that results in a decrease (e.g., an observable, a significant, or a detectable decrease) in meibomian gland production and/or secretion (e.g., meibum production and/or secretion).

By the term "acini" or "acini present in a meibomian gland" is meant one or more three-dimensional grape-like cluster(s) of cells interlinked by ductules and ducts that collectively form a meibomian gland that produce(s) and secrete(s) meibum. In healthy individuals, meibum is released through the duct of the meibomian gland onto the ocular surface to form the external layer of the tear film.

By the term "duct or ductule of a meibomian gland" is meant an anatomical sub-structure present in a meibomian gland that allows for the passage of secretions produced within the meibomian gland to the orifice at the lid margin.

By the term "immune cells" is meant any type of immune cell that can infiltrate the eyelid. Non-limiting examples of immune cells include macrophages, dendritic (Langerhans) cells, mast cells, neutrophils, and T- and B-lymphocytes. Exemplary methods for detecting the presence of immune cells in the palpebral conjunctival epithelium, in the palpebral conjunctival substantia propria, within meibomian gland(s) (intraglandular, e.g., within ducts, ductules, and/or acini), and proximal to meibomian gland(s) using in vivo confocal microscopy are described herein.

By the term "palpebral conjunctival epithelium" is meant the layer of columnar and/or cuboidal, stratified epithelial cells that lines the inside of the eyelid and directly abuts the conjunctiva of the eyeball (bulbar conjunctiva) (e.g., when the eyelid is closed or partially closed). In some embodiments, the layer of epithelial cells constituting the palpebral conjunctival epithelium can be less than 30 µm (e.g., less than 25 µM or less than 20 µM) thick or can contain 2 layers of epithelial cells.

By the term "palpebral conjunctival substantia propria" is meant the connective tissue layer (submucosa) of the eyelid that the palpebral conjunctival epithelium rests upon. The palpebral conjunctival substantial propria of a healthy (normal) subject typically contains mast cells, lymphocytes, plasma cells, neutrophils, and collagen, and can also contain blood and lymph vessels, and nerves. One or more meibomian glands are typically located in the palpebral conjunctival substantia propria of the eyelid.

By the term "allergy" is meant a hypersensitivity disorder of the immune system that is triggered by an allergen. Several of the symptoms of allergy are mediated by the activation of mast cells and basophils in a subject (e.g., in the eyelid or eye of a subject) that release several mediators into the tissue of the subject (e.g., one or more mediators selected from the group consisting of: serine proteases, histamine, serotonin, heparin, thromboxane, prostaglandin D2, leukotriene C4, platelet-activating factor, and eosinophil-activating factor).

By the term "atopic keratoconjunctivitis" or "AKC" is meant a form of conjunctivitis caused by allergy. In some embodiments, AKC is a bilateral chronic disease that is associated with atopic dermatitis.

By the term "vernal keratoconjunctivitis" or "VKC" is meant a long-term (e.g., chronic) swelling of the outer lining of the eyes caused by an allergic reaction.

By the term "tear break-up time" is meant a clinical score that indicates the stability of the tear film in a subject. A number of clinical tests are available for determining the tear break-up time in a subject. In some embodiments, the tear break-up time is assessed by: adding a sodium fluorescein dye to a subject's eye; observing the dye, while the patient avoids blinking; and recording the elapsed amount of time before tiny dry spots appear on the cornea. In such embodiments, the longer it takes for the dry spots to develop, the more stable the tear film is in the subject. A variety of additional assays for determining the tear break-up time in a subject are available in the art.

By the term "corneal fluorescein staining" is meant a clinical procedure that is used to assess corneal injury, corneal defect(s), or defects in the tear film in a subject. In some embodiments of this procedure, a piece of hydrated blotting paper containing a dye (e.g., fluorescein) is brought into contact with the subject's eye, who is then asked to blink, and the subject's eye is visualized with a blue light. Any corneal abrasions, corneal defect(s), or structural inconsistencies in the tear film will be observed by a speckled, uneven distribution of the dye in the eye of the subject.

By the term "anti-inflammatory antimicrobial agent" is meant an antimicrobial agent that has one or more anti-inflammatory properties when administered to a subject (e.g., one or more of reducing inflammation, reducing swelling, inhibiting cyclooxygenase activity, and decreasing the activation or migration of immune cells). In some embodiments, an anti-inflammatory antimicrobial agent can have one or more activities selected from: the ability to reduce interleukin-8 levels, interleukin-6 levels, and TNF-α levels in a subject. Non-limiting examples of anti-inflammatory antimicrobial agents include doxycycline and azithromycin. Additional non-limiting examples of anti-inflammatory antimicrobial agents are described herein, and are known in the art.

By the term "meibomian gland probing" is meant a technique by which one or more meibomian glands are decompressed with a cannula and optionally lavaged with a pharmaceutically acceptable solvent (e.g., a pharmaceutically acceptable solvent containing one or more pharmaceutical agents). Methods for performing meibomian gland probing are known in the art.

By the term "efficacy" or "efficacy of treatment" is meant the ability of a treatment (e.g., a therapeutic treatment for MGD) to reduce the number of symptoms of a disease or disorder in a subject (e.g., reduce the number of symptoms of MGD) and/or decrease (e.g., a significant, detectable, or observable decrease) the severity, frequency, and/or duration of one or more (e.g., at least two, three, or four) symptoms of a disease or disorder in a subject (e.g., reduce the severity, frequency, and/or duration of one or more symptoms of MGD in a subject).

By the term "in vivo confocal microscopy" is meant the use of real-time confocal microscope to visualize one or more tissue(s), glands, glandular sub-anatomical structures, cells, and/or cellular substructures present within a mammal (e.g., a human). Exemplary methods of performing in vivo confocal microscopy are described herein.

By the term "reference value" is meant a value that is used for comparative purposes. In some embodiments, a reference value for one or more of the physical parameters described herein can be a threshold value. In some embodiments, a reference value for the one or more physical parameters can be a level or value of the one or more physical parameters measured in a healthy subject (e.g., a subject that does not present with one or more symptoms of an eye disorder (e.g., MGD) or a subject that has not been diagnosed as having an eye disorder (e.g., MGD)). Additional examples of reference values are described herein.

By the term "subject" is meant any mammal (e.g., a human, mice, rat, or rabbit).

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF THE INVENTION

Figure 1:
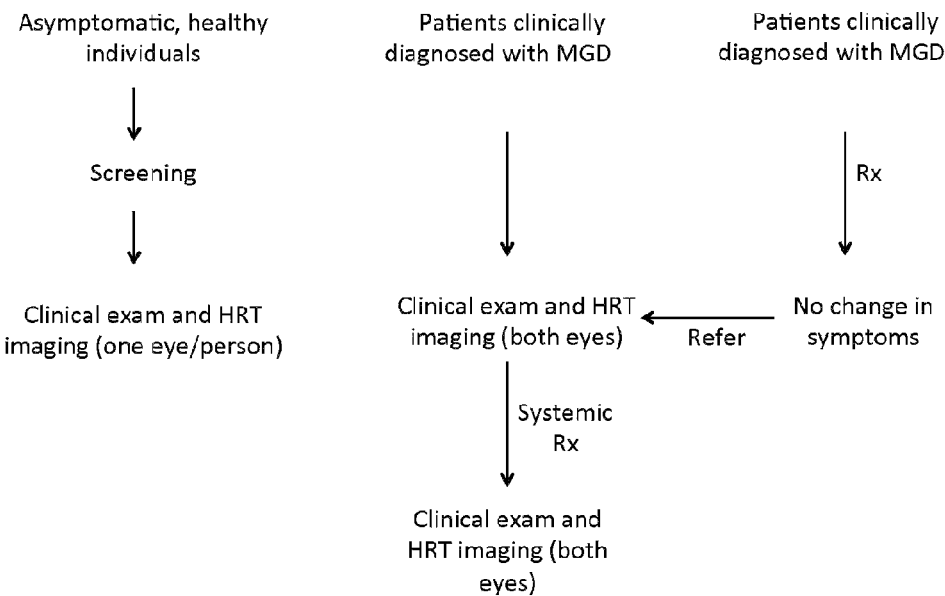
FIG. 1 is a diagram of the design of a study performed to determine changes in the eyelids of subjects having meibomian gland dysfunction (MGD) that are measured using in vivo confocal microscopy (e.g., Heidelberg Retina Tomograph or HRT).

The invention is based, at least in part, on the discovery that subjects with meibomian gland dysfunction (MGD) have observable, quantifiable, physical changes including one or more of an elevation in the number and/or density of immune cells in the palpebral conjunctival epithelium, an elevation in the number and/or density of immune cells in the palpebral conjunctival substantia propria, an elevation in the number, area, and/or density of immune cells within one or more ducts/ductules of one or more meibomian gland(s) and/or around one or more meibomian glands, an elevation in the level of glandular/ductal obstruction in one or more meibomian gland(s), and an elevation in the size of one or more ducts/ductules present in one or more meibomian gland(s) in one or both of the eyelids, as compared to a normal healthy control (e.g., a subject not having eye disease, e.g., a subject not having MGD). The invention is also based, in part, on the discovery that subjects having MGD that are successfully treated have one or more of a decrease in the number and/or density of immune cells in the palpebral conjunctival epithelium, a decrease in the number and/or density of immune cells in the palpebral conjunctival substantia propria, a decrease in the number, area, and/or density of immune cells present within one or more ducts/ductules of one or more meibomian glands and/or around one or more meibomian glands, a decrease in the level of glandular/ductal obstruction in one or more meibomian gland(s), and a decrease in the size of one or more ducts/ductules in one or more meibomian gland(s) in one or both of the eyelids following treatment as compared to prior to treatment.

In view of these discoveries, provided herein are methods of diagnosing an eyelid disorder (e.g., MGD) in a subject, determining the severity of an eyelid disorder (e.g., MGD) in a subject, evaluating the efficacy of treatment in a subject having an eyelid disorder (e.g., MGD), selecting a subject for treatment of an eyelid disorder (e.g., MGD), and selecting a subject for participation in a clinical study. These methods include determining in the eyelid of a subject (e.g., at one or more time points) one or more of: the number and/or density of immune cells in the palpebral conjunctival epithelium, the number and/or density of immune cells in the palpebral conjunctival substantia propria, the number, area, and/or density of immune cells present within one or more ducts/ductules of one or more meibomian glands and/or around one or more meibomian glands, the level of glandular/ductal obstruction in one or more meibomian gland(s), and the size of one or more ducts/ductules present in one or more meibomian gland(s). Also provided are methods of treating a subject (e.g., a subject having MGD) that include selectively orally administering to a subject having an eyelid disorder (e.g., MGD) and determined to have an elevated number and/or density of immune cells in the palpebral conjunctival substantia propria as compared to a reference level, at least one anti-inflammatory antimicrobial agent, and/or selectively performing meibomian gland probing on a subject (e.g., a subject having an eyelid disorder, e.g., MGD) and determined to have an elevation in the level of glandular/ductal obstruction in one or more meibomian gland(s) as compared to a reference level. Various embodiments of these methods are described herein.

Meibomian Gland Dysfunction (MGD)

Meibomian gland dysfunction is an abnormality (e.g., a chronic abnormality) of meibomian gland function in the eyelid of a subject that can result in meibomian gland obstruction, terminal duct obstruction, and/or a decrease (e.g., an observable, detectable, or significant decrease) in meibomian gland secretion. Meibomian glands are large sebaceous glands located in the eyelids. These glands normally actively synthesize and secrete lipids and proteins that are delivered at the upper and lower eyelid margins just anterior to the mucocutaneous junctions. The secreted lipids spread onto the tear film and promote its stability, and prevent its evaporation. Meibomian glands contain multiple secretory acini that contain meibocytes, lateral ductules, a central duct, and a terminal excretory duct that opens at the posterior lid margin. Meibomian glands produce both polar and nonpolar lipids (also called meibum) that are secreted into the ducts. Meibum delivery onto the lid margin occurs with muscular contraction during lid movement.

Non-limiting symptoms of MGD include dry eyes, pain or a burning sensation in the eyes, tear evaporation, hyperosmolarity, and instability of the tear film, increased bacterial growth on the lid margin, and ocular surface inflammation and damage. MGD has a variety of different causes including, but not limited to, androgen deficiency, menopause, Sjogren's syndrome, and psoriasis. In some embodiments, the MGD is a hyposecretory form of MGD (e.g., a condition of decreased meibum delivery due to abnormalities in meibomian glands without remarkable obstruction). In some embodiments, the MGD is a hypersecretory form of MGD (e.g., a condition characterized by the release of a large volume of lipid at the lid margin that becomes visible on application of pressure onto the tarsus during examination). In some embodiments, a subject having MGD is not diagnosed as having an allergy, does not have allergy, and/or has a form of MGD that is not caused by allergy. In some embodiments, a subject having MGD is not diagnosed or does not have atopic keratoconjunctivitis or vernal conjunctivitis.

MGD can be diagnosed in a subject by assessing one or more (e.g., two, three, or four) symptoms of MGD including, but not limited to: dry eyes, pain or a burning sensation in the eyes, increased evaporation, hyperosmolarity, and instability of the tear film, increased bacterial growth on the lid margin, and ocular surface inflammation and damage. MGD can further be diagnosed by assessment of gland expression and secretion quality (e.g., by the application of moderate digital pressure to the central lower lid, and tests of tear osmolarity, secretion, volume, stability, and evaporation known in the art) or assessment of ocular surface damage and dry eye (e.g., using the corneal fluorescein staining, tear break-up time, Ocular Surface Disease Index (OSDI), and Dry Eye Questionnaire (DEQ) methods known in the art). Additional methods for diagnosing MGD in a subject (e.g., using in vivo confocal microscopy) are provided herein. Additional methods for diagnosing MGD in a subject are known in the art.

In some embodiments, a subject can be diagnosed as having MGD by a health care professional (e.g., a physician, a physician's assistant, a nurse, a nurse's assistant, and a laboratory technician). In some embodiments, a subject diagnosed as having MGD can be a child, a teenager, or an adult (e.g., at least 18, 20, 25, 30, 35, 40, 45, 50, 55, 60, 65, 70, 75, 80, 85, or 90 years old). A subject diagnosed as having MGD may present with one or more (e.g., at least two, three, or four) of the symptoms of MGD described herein. In some embodiments, a subject having MGD may not present with a symptom of MGD that can be easily detected by basic examination of an eye(s) of the subject (examination of the patient that does not involve the magnification of the tissues of the eye). In some embodiments, the subject can be diagnosed as having MGD based, in part, on the detection of one or more (e.g., two, three, four, or five) of the physical parameters described herein. For example, the subject can be diagnosed (e.g., alone or in part) as having MGD based on the detection of one or more (e.g., two, three, four, or five) of the following physical parameters in an eyelid of the subject (e.g., using in vivo confocal microscopy): (i) the number and/or density of immune cells present in the palpebral conjunctival epithelium, (ii) the number and/or density of immune cells present in the palpebral conjunctival substantia propria, (iii) the number, area, and/or density of immune cells present within one or more ducts/ductules present in one or more meibomian gland(s) and/or around one or more meibomian glands, (iv) the level of glandular/ductal obstruction in one or more meibomian gland(s), and (v) the size of one or more ducts/ductules present in one or more meibomian gland(s), where one or more of: an elevation in the number and/or density of immune cells present in the palpebral conjunctival epithelium, an elevation in the number and/or density of immune cells present in the palpebral conjunctival substantia propria, an elevation in the number, area, and/or density of immune cells present within one or more ducts/ductules present within one or more meibomian gland(s) and/or around one or more meibomian glands, an elevation in the level of glandular/ductal obstruction in one or more meibomian gland(s), and an elevation in the size of one or more ducts/ductules present in one or more meibomian gland(s) in the subject compared to one or more corresponding reference values (e.g., a threshold value or the corresponding level(s) present in a healthy subject (e.g., a subject that does not have eye disease, e.g., a subject that does not have MGD)) indicate that the subject has MGD.

In some embodiments, the subject is a woman in menopause or a subject having androgen deficiency, Sjogren's syndrome, psoriasis, rosacea, hypertension, or benign prostatic hyperplasia. In some embodiments, the subject is taking or was previously administered one or more of: an anti-androgen, a post-menopausal hormone therapy (e.g., estrogens and progestins), an anti-histamine, an antidepressant, and a retinoid.

In Vivo Microscopy

In vivo microscopy (e.g., in vivo confocal microscopy) is a noninvasive procedure that allows the imaging of the living tissues present in the eyelid at the cellular level. This technique enables the study of immune cells in the palpebral conjunctival epithelium, immune cells in the palpebral conjunctival substantia propria (stroma), immune cells present within one or more ducts/ductules within one or more meibomian gland(s) and/or around one or more meibomian glands, glandular/ductal obstruction in meibomian glands, and the ducts/ductules present in meibomian gland(s) that are present in the eyelid of a subject. Additional examples of cells and glandular sub-anatomical structures that can be analyzed using in vivo microscopy (e.g., in vivo confocal microscopy) are described in the Examples. Exemplary methods for detecting these specific cells and structures are also described herein (see, the Examples).

In vivo confocal microscopes are commercially available from, e.g., Nidek Technologies (Gamagori, Japan) and Heidelberg Engineering GmbH (Dossenheim, Germany). In the methods described herein, the confocal microscopes are commonly equipped with a 35× to 70× immersion lens.

These methods can be performed, for example, using a Confoscan microscope equipped with a 40×/0.75 objective lens or a Heidelberg Engineering GmbH microscope equipped with a 63× water-contact objective lens covered with a sterile single-use polymethylmethacrylate cap. The Confoscan microscope can produce images of 460×345 µm, with a magnification of 500×, and lateral resolution of 1 µm/pixel. The Heidelberg microscope can produce images of 400×400 µm, having a magnification of 800×, and a resolution of 1 µm/pixel.

In these methods, the subject is typically administered a topical anesthesia (e.g., 0.5% proparacaine hydrochloride) prior to contacting the immersion lens with the subject's eye tissue (e.g., contacting the immersion lens to the folded-back eyelid of the subject). A subject can also be administered a lubricating solution (e.g., 2.5% hydroxypropyl methylcellulose) prior to contacting the immersion lens with the subject's eye tissue. The digital images collected can be stored on a computer workstation using commonly known methods. The resulting images can be analyzed using a variety of commercially available software. A non-limiting example of software that can be used to analyze the collected images is ImageJ software (ImageJ software described in Girish et al., *Indian J. Cancer* 41:47, 2004).

Changes in Immune Cells in Palpebral Conjunctival Epithelium and Substantia Propria As described herein, subjects having MGD have an elevated number and/or density of immune cells (e.g., one or more of dendritic cells, macrophages, T-lymphocytes, and neutrophils) present in the palpebral conjunctival epithelium and/or palpebral conjunctival substantia propria of one or both eyelid(s) as compared to a reference value (e.g., a threshold value or level present in a control (healthy) subject that does not have an eye disorder (e.g., a subject that does not have MGD)). The invention is further based, in part, on the discovery that successful treatment in a subject having MGD is correlated with a decrease in the number and/or density of immune cells present in the palpebral conjunctival epithelium and/or palpebral conjunctival substantia propria.

The palpebral conjunctival epithelium is a layer of columnar and/or cuboidal, stratified epithelial cells that lines the inside of the eyelid and directly abuts the conjunctiva of the eyeball (e.g., when the eyelid is closed or partially closed). In some embodiments, the layer of epithelial cells constituting the palpebral conjunctival epithelium is less than 30 µm (e.g., less than 25 µm) thick. In some embodiments, the immune cells present in the palpebral conjunctival epithelium range in appearance, e.g., appear as (approximately spherical), hyperreflective cells, or polymorphic hyperreflective cells with or without dendrites.

The palpebral conjunctival substantia propria is the connective tissue layer (submucosa or stroma) of the eyelid that the palpebral conjunctival epithelium rests upon. The palpebral conjunctival substantia propria of a healthy (normal) subject typically contains mast cells, lymphocytes, plasma cells, neutrophils, and collagen, and can also contain blood and lymph vessels, and nerves.

The number and density of immune cells present in the palpebral conjunctival epithelium and/or palpebral conjunctival substantia propria can be determined using methods (e.g., in vivo microscopic methods) known in the art or described herein. Exemplary in vivo confocal microscopy methods for determining the number and density of immune cells present in the palpebral conjunctival epithelium and/or palpebral conjunctival substantia propria are described herein. As one of skill in the art will appreciate, a number of variables of the exemplary in vivo confocal microscopic methods described herein can be altered without significantly changing the quality of the results or data obtained (e.g., changes in the laser source and subtle changes in the power of the immersion lens). The number and density of immune cells present in the palpebral conjunctival epithelium and/or palpebral conjunctival substantia propria can be assessed in the collected in vivo confocal micrographs using available software (e.g., ImageJ software described in Girish et al., *Indian J. Cancer* 41:47, 2004). Additional examples of software that can be used to assess the number or density of immune cells present in the palpebral conjunctival epithelium and/or palpebral conjunctival substantia propria are known in the art.

Changes in Immune Cells within Meibomian Glands

The invention is also based, in part, on the discovery that subjects having MGD have an elevated number, area, and/or density of immune cells (e.g., one or more of dendritic cells, macrophages, T-lymphocytes, B-lymphocytes and neutrophils) present within one or more ducts/ductules within one or more meibomian gland(s) in one or both eyelid(s) as compared to a reference value (e.g., a threshold value or a level present in a control (healthy) subject that does not have an eye disorder (e.g., a subject that does not have MGD)). The invention is further based, in part, on the discovery that successful treatment in a subject having MGD is correlated with a decrease in the number, area, and/or density of immune cells present in one or more ducts/ductules within one or more meibomian gland(s) present in one or both eyelids of the subject (e.g., as compared to an earlier time point in treatment or a time point prior to treatment).

As described herein, meibomian glands contain a number of substructures including, but not limited to: multiple secretory acini that contain meibocytes, and lateral ductules, a central duct, and a terminal excretory duct that opens at the posterior lid margin. Meibomian glands have a distinctive ductal morphology that can be easily discerned in an in vivo confocal micrograph by one skilled in the art (see, e.g., Jester et al., *Invest. Ophthalmol. Vis. Sci.* 20:537-547, 1981). In some embodiments, the immune cells present in the palpebral conjunctival epithelium can range in appearance, e.g., appear as punctate (approximately spherical), hyperreflective cells or as polymorphous hyperreflective cells with or without dendrites.

The number and density of immune cells present in the one or more ducts/ductules within one or more meibomian gland(s) in a subject can be determined using the exemplary in vivo confocal microscopy methods described herein. As one of skill in the art will appreciate, a number of variables of the exemplary in vivo confocal microscopic methods described herein can be altered without significantly changing the quality of the results or data obtained (e.g., changes in the laser source and the properties (e.g., power) of the immersion lens). The number, area, and density of immune cells present in one or more ducts/ductules within one or more meibomian gland(s) can be assessed in the gathered in vitro confocal micrographs using available software (e.g., ImageJ software described in Girish et al., *Indian J. Cancer* 41:47, 2004). Additional examples of software that can be used to assess the number or density of immune cells present in one or more ducts/ductules in meibomian gland(s) are known in the art. In some embodiments, the number or density of immune cells is determined in at least two (e.g., at least three, four, five, or six) ducts/ductules within one or more (e.g., at least two, three, four, or five) meibomian glands present in an eyelid of the subject.

Changes in Inflammatory Cells Around Meibomian Glands

As described herein, subjects having MGD have an elevated number, area, and/or density of immune cells around one or more meibomian glands present in one or both eyelid(s) as compared to a reference value (e.g., a threshold value or level present in a control (healthy) subject that does not have an eye disorder (e.g., a subject that does not have MGD)). The invention is further based, in part, on the discovery that successful treatment in a subject having MGD is correlated with a decrease in the number, area, and/or density of immune cells around one or more meibomian gland(s) present in one or both eyelids of the subject (e.g., as compared to an earlier time point in treatment or a time point prior to treatment).

As described herein, meibomian glands contain a number of sub-anatomical structures including, but not limited to: multiple secretory acini that contain meibocytes, and lateral ductules, a central duct, and a terminal excretory duct that opens at the posterior lid margin. Meibomian glands have a distinctive ductal morphology that can be easily discerned in an in vivo confocal micrograph by one skilled in the art (see, e.g., Jester et al., Invest. Ophthalmol. Vis. Sci. 20:537-547, 1981). In some embodiments, the inflammatory cells present in the palpebral conjunctival epithelium range in appearance, e.g., appear as punctate, non-dendriform (approximately spherical), hyperreflective cells, or polymorphous hyperreflective cells with or without dendrites.

The number, area, and/or density of inflammatory cells around one or more meibomian gland(s) in one or both eyelids of a subject can be determined using methods (e.g., in vivo microscopic methods) known in the art or described herein. Exemplary in vivo confocal microscopy methods that can be used to determine the number, area, and/or density of inflammatory cells around one or more meibomian gland(s) are described herein (see, e.g., the Examples). As one of skill in the art will appreciate, a number of variables of the exemplary in vivo confocal microscopic methods described herein can be altered without significantly changing the quality of the results or data obtained (e.g., changes in the laser source and the properties (e.g., power) of the immersion lens). The number, area, and/or density of immune cells around one or more meibomian gland(s) present in one or both eyelids in a subject can be assessed in the gathered in vitro confocal micrographs using available software (e.g., ImageJ software described in Girish et al., Indian J. Cancer 41:47, 2004). Additional examples of software that can be used to assess the number, area, and/or density of inflammatory cells around one or more meibomian gland(s) present in one or both eyelids of a subject are known in the art. In some embodiments, the number, area, and/or density of inflammatory cells is determined around at least two (e.g., at least three, four, five, or six) meibomian glands present in an eyelid of the subject.

Levels of Meibomian Gland Obstruction

The invention is also based, in part, on the discovery that subjects having MGD have an elevated level of glandular/ductal obstruction in one or more meibomian glands present in one or both eyelid(s) as compared to a reference value (e.g., a threshold value or level present in a control (healthy) subject that does not have an eye disease (e.g., a subject that does not have MGD)). The invention is further based, in part, on the discovery that successful treatment in a subject having MGD is correlated with a decrease in the level of glandular/ductal obstruction (e.g., ductal/ductile obstruction) in one or more Meibomian gland(s) present in one or both eyelids of the subject (e.g., as compared to an earlier time point in treatment or a time point prior to treatment).

Meibomian glands have a distinctive ductal morphology that can be easily discerned in an in vivo confocal micrograph by one skilled in the art (see, e.g., Jester et al., Invest. Ophthalmol. Vis. Sci. 20:537-547, 1981). Meibomian gland obstruction can be assessed, for example, by a detection of one or more of the plugging or partial or complete blockage of one or more of the lateral ductules or the central duct in a meibomian gland (e.g., as compared to a threshold value or corresponding reference level(s) in a subject that does not have an eye disorder (e.g., a subject that does not have MGD).

The level/extent of glandular/ductal obstruction in one or more meibomian gland(s) in one or both eyelids of a subject can be determined using the exemplary in vivo confocal microscopy methods described herein. As one of skill in the art will appreciate, a number of variables of the exemplary in vivo confocal microscopic methods described herein can be altered without significantly changing the quality of the results or data obtained (e.g., changes in the laser source and the properties (e.g., power) of the immersion lens). The level/extent of obstruction of one or more ducts of one or more meibomian gland(s) present in one or both eyelids in a subject can be assessed in the gathered in vivo confocal micrographs using available software (e.g., ImageJ software described in Girish et al., Indian J. Cancer 41:47, 2004). Additional examples of software that can be used to assess the level/extent of obstruction of one or more ducts in one or more meibomian gland(s) present in one or both eyelids of a subject are known in the art. In some embodiments, the level of obstruction is determined after analysis of at least two (e.g., at least three, four, five, or six) in vivo confocal micrographs of that eyelid. Meibomian glands present in an eyelid of the subject. The depth of image can, e.g., range from 30-90 µm, but can be more superficial or deep.

Size of Ducts and Ductules in Meibomian Glands

The invention is also based, in part, on the discovery that subjects having MGD have an elevation in the size (luminal dimensions) of one or more ducts/ductules present in one or more meibomian gland(s) (in one or both eyelids) or a decrease in the size (dimensions) of one or more acini present in one or more mebomian glands as compared to a reference value (e.g., a threshold value or level present in a control (healthy) subject that does not have an eye disorder (e.g., a subject that does not have MGD)). The invention is further based, in part, on the discovery that successful treatment in a subject having MGD is correlated with a decrease in the size (luminal dimensions) of one or more ducts/ductules present in one or more meibomian gland(s) and/or an increase in the size (dimensions) of one or more acini (e.g., in one or both eyelid(s)) of the subject (e.g., as compared to an earlier time point in treatment or a time point prior to treatment).

Meibomian glands contain multiple secretory acini that contain meibocytes that produce lipids and proteins (meibum) that are eventually excreted through the ducts of the meibomian gland onto lid margin, which then forms the outermost layer of the tear film. Meibomian gland acini have a distinctive morphology that can be easily discerned in an in vivo confocal micrograph by one skilled in the art (see, e.g., Jester et al., Invest. Ophthalmol. Vis. Sci. 20:537-547, 1981). Meibomian glands also contain ducts and ductules that transport the secretions produced by the meibomian gland to the orifice on at the lid margin. Meibomian gland ducts and ductules can also be detected using the methods known in the art and the methods described herein (see, e.g., the Examples)

The size of one or more acini and/or ducts/ductules in one or more meibomian gland(s) in an eyelid of a subject can be determined using the exemplary in vivo confocal microscopy methods described herein. As one of skill in the art will appreciate, a number of variables of the exemplary in vivo microscopic methods described herein can be altered without significantly changing the quality of the results or data obtained (e.g., changes in the laser source and properties (e.g., power) of the immersion lens).

The size (luminal dimensions) of one or more meibomian gland acini (e.g., the average size of one or more meibomian gland acini) and/or one or more meibomian gland ducts/ductules can be quantitated by determining the maximum length and width of one or more acini and/or one or more ducts/ductules in a two-dimensional in vivo confocal micrograph (e.g., an estimate of the dimensions can be determined by manually placing calipes from one end to another in the lumen of a duct, at the longest longitudinal and widest perpendicularly horizontal meridians of the duct/ductile/acini) and/or by determining the two-dimensional area taken up by one or more ducts/ductules/acini in a two-dimensional in vivo confocal micrograph (e.g., approximately the area of a circle, roughly equivalent to approximately half the measured width of the duct). The maximum length and width of one or more acini/ducts/ductules and the average two-dimensional area taken up by one or more acini/ducts/ductules (as described herein) can be determined in a two-dimensional in vivo confocal micrograph using available software programs (e.g., ImageJ). Additional examples of software that can be used to determine the maximum length and width of one or more acini/ducts/ductules, and the average two-dimensional area taken up by one or more acini/ducts/ductules (as described herein) are known in the art. In some embodiments, the size of one or more acini/ducts/ductules (e.g., the average size of at least two, three, four, or five acini/ducts/ductules) is determined after analysis of one or more (e.g., at least two, three, or four) meibomian glands present in an eyelid of the subject. The acini/ducts/ductules of meibomian glands can be detected in images taken at a depth of magnification of, e.g., 35-90 µm.

In some embodiments, the size of one or more meibomian gland ducts/ductules (e.g., the average diameter of one or more meibomian gland ducts/ductules) can be quantitated by determining the maximum width of one or more ducts or ductules in a two-dimensional in vivo confocal micrograph (e.g., an estimate of the size of a duct/ductule can be determined by measuring the width of a duct/ductule), and/or by determining the two-dimensional area taken up by one or more ducts/ductules in a two-dimensional in vivo confocal micrograph. In some embodiments, the maximum width of one or more duct/ductules and the average two-dimensional area taken up by one or more ducts/ductules (as described herein) can be determined in a two-dimensional in vivo confocal micrograph using available software programs (e.g., ImageJ). Additional examples of software that can be used to determine the maximum width of one or more ducts/ductules, and the average two-dimensional area taken up by one or more ducts/ductules (as described herein) are known in the art. In some embodiments, the size of one or more ducts/ductules (e.g., the average size of at least two, three, four, or five ducts/ductules) is determined after analysis of one or more (e.g., at least two, three, or four) meibomian glands present in an eyelid of the subject. The ducts/ductules of meibomian glands can be detected in images taken at a depth of magnification of, e.g., 35-90 µm.

Methods of Diagnosing Meibomian Gland Dysfunction

Provided herein are methods of diagnosing or assisting in the diagnosis of an eyelid disorder (e.g., MGD) in a subject that include: determining in an eyelid of a subject one or more (e.g., two, three, four, or five) physical characteristics selected from (i) the number and/or density of immune cells in the palpebral conjunctival epithelium, (ii) the number and/or density of immune cells in the palpebral conjunctival substantia propria, (iii) the number, area, and/or density of immune cells present within one or more ducts/ductules in one or more meibomian gland(s) and/or around one or more meibomian glands, (iv) the level of glandular/ductal obstruction in one or more meibomian gland(s), and (v) the size of one or more ducts/ductules present in one or more meibomian gland(s); and comparing the one or more physical characteristics determined in the eyelid of the subject to one or more corresponding reference values, where the determining is performed using methods (e.g., in vivo confocal microscopy) known in the art or described herein, and one or more (e.g., two, three, four, or five) of an elevation in the number and/or density of immune cells in the palpebral conjunctival epithelium, an elevation in the number and/or density of immune cells in the palpebral conjunctival substantia propria, an elevation the number, area, and/or density of immune cells present within one or more ducts/ductules present within one or more meibomian gland(s) and/or around one or more meibomian glands, an elevation in the level of glandular/ductal obstruction in one or more meibomian gland(s), and an elevation in the size of one or more ducts/ductules present in one or more meibomian gland(s), compared to the one or more corresponding reference values, indicates that subject has an eyelid disorder (e.g., MGD). In some embodiments, the determining is performed using in vivo confocal microscopy.

Some embodiments of these methods include determining, i.e., in an eyelid, of a subject one or more (e.g., one, two, or three) physical characteristics selected from the group of (i) the number, area, and/or density of immune cells present within one or more ducts/ductules within one or more meibomian gland(s) and/or around one or more meibomian glands, (ii) the level of glandular/ductal obstruction in one or more meibomian gland(s), and (iii) the size of one or more ducts/ductules present in one or more meibomian gland(s); and comparing the one or more physical characteristics determined in the eyelid of the subject to one or more corresponding reference values, where one or more (e.g., one, two, or three) of an elevation the number, area, and/or density of immune cells present within one or more ducts/ductules in one or more meibomian gland(s) and/or around one or more meibomian glands, an elevation in the level of glandular/ductal obstruction in one or more meibomian gland(s), and an elevation in the size of one or more ducts/ductules present in one or more meibomian gland(s) in the eyelid of the subject compared to the one or more corresponding reference values, indicates that subject has an eyelid disorder (e.g., MGD). In some embodiments, these methods further include determining one or more additional physical characteristics selected from the group of the number and/or density of immune cells present in the palpebral conjunctival epithelium, and/or the number and/or density of immune cells present in the palpebral conjunctival substantia propria in the eyelid of the subject; and comparing the one or more additional physical characteristics determined in the eyelid of the subject to one or more corresponding reference values, where one or more of an elevation in the number and/or density of immune cells in the palpebral conjunctival epithelium and an elevation in the number and/or density of immune cells in the palpebral conjunctival substantia propria in the eyelid of the subject compared to the one or more corresponding reference values, indicates that the subject has an eyelid disorder (e.g., MGD).

In some embodiments of the methods described herein, the reference value is a threshold value. Exemplary, non-limiting, threshold values of the density of immune cells in the palpebral conjunctival epithelium are 200 cells/mm$^2$, 220 cells/mm$^2$, 240 cells/mm$^2$, 260 cells/mm$^2$, or 280 cells/mm$^2$, 300 cells/mm$^2$, 320 cells/mm$^2$, or 340 cells/mm$^2$, or a range of 200-220 cells/mm$^2$, 220-240 cells/mm$^2$, 260-280 cells/mm$^2$, 280-300 cells/mm$^2$, 300-320 cells/mm$^2$, or 320-340 cells/mm$^2$. Exemplary, non-limiting, threshold values of the density of immune cells in the palpebral conjunctival substantia propria include values of 50 cells/mm$^2$, 60 cells/mm$^2$, 70 cells/mm$^2$, 80 cells/mm$^2$, 90 cells/mm$^2$, or 100 cells/mm$^2$, or a range of 50-60 cells/mm$^2$, 60-70 cells/mm$^2$, 70-80 cells/mm$^2$, 80-90 cells/mm$^2$, or 90-100 cells/mm$^2$. Exemplary, non-limiting, threshold values of the density of immune cells present within one or more ducts/ductules of one or more meibomian glands are percent luminal area occupied by intraglandular immune cells values of 10, 15, 20, 25, 30, or 35, or a range of 10-20, 20-25, 25-30, or 30-35. Other exemplary threshold values for the physical characteristics described herein known in the art or can be obtained using methods known in the art. In some embodiments of the methods described herein, the reference value is: the number and/or density of immune cells present in the palpebral conjunctival epithelium, the number and/or density of immune cells present in the palpebral conjunctival substantia propria, the number and/or density of immune cells present within one or more ducts/ductules in one or more meibomian gland(s), the level of glandular/ductal obstruction in one or more meibomian glands, and the size of one or more ducts/ductules present in one or more meibomian gland(s) determined in an eyelid of a healthy subject (e.g., a subject that does not have an eye disease (e.g., a subject that does not have MGD or has not been diagnosed as having MGD). In some embodiments, the subject is not diagnosed as having an allergy and/or does not have an allergy. In some embodiments, the subject is not diagnosed as having atopic keratoconjunctivitis or vernal conjunctivitis, or does not have atopic keratoconjunctivitis or vernal conjunctivitis. In some embodiments, the subject is a woman in menopause or a subject having androgen deficiency, Sjogren's syndrome, psoriasis, rosacea, hypertension, or benign prostatic hyperplasia. In some embodiments, the subject taking or was previously administered one or more of: an anti-androgen, a postmenopausal hormone therapy (e.g., estrogens and progestins), an antihistamine, an antidepressant, or a retinoid. In some embodiments, the MGD is a hyposecretory form of MGD (e.g., a condition of decreased meibum delivery due to abnormalities in meibomian glands without remarkable obstruction). In some embodiments, the MGD is a hypersecretory form of MGD (e.g., a condition characterized by the release of a large volume of lipid at the lid margin that becomes visible on application of pressure onto the tarsus during examination).

In some embodiments, a subject can be diagnosed as having MGD by a health care professional (e.g., a physician, a physician's assistant, a nurse, a nurse's assistant, and a laboratory technician). In some embodiments, a subject diagnosed as having MGD can be a child, a teenager, or an adult (e.g., at least 18, 20, 25, 30, 35, 40, 45, 50, 55, 60, 65, 70, 75, 80, 85, or 90 years old). A subject diagnosed as having MGD may present with one or more (e.g., at least two, three, or four) of the symptoms of MGD described herein. In some embodiments, a subject having MGD may not present with a symptom of MGD that can be easily detected by basic examination of an eye(s) of the subject (examination of the patient that does not involve the magnification of the tissues of the eye). In some embodiments, the subject is suspected of having an eyelid disorder (e.g., MGD) or has an increased risk of developing an eyelid disorder (e.g., MGD).

Some embodiments further include the assessing one or more (e.g., two, three, four, or five) additional symptoms of MGD in the subject (e.g., one or more symptoms of MGD that can be assessed without the aid of an in vivo confocal microscope) (e.g., one or more of dry eyes, pain or a burning sensation in the eyes, increased evaporation, hyperosmolarity, and instability of the tear film, increased bacterial growth on the lid margin, and ocular surface inflammation and damage). Some embodiments further include performing a test to determine tear film quality (e.g., a test to determine tear osmolarity or tear break-up time) or a test to assess corneal damage (e.g., corneal fluorescein staining, Ocular Surface Disease Index (OSDI) scoring, and Dry Eye Questionnaire (DEQ) scoring). Methods for determining tear osmolarity and tear break-up time, and performing corneal fluorescein staining, OSDI scoring, and DEQ scoring are known in the art. In some embodiments, one or more of an elevation in corneal fluorescein staining, tear osmolarity, tear break-up time, OSDI scoring, and DEQ scoring further indicates that the subject has MGD. Some embodiments further include performing a tear production test (e.g., Schirmer's test), wherein a decrease in tear production as compared to a reference value (e.g., a level of tear production in a healthy subject (e.g., a subject not having an eye disease, e.g., a subject not having MGD)) further indicates that the subject has an eyelid disorder (e.g., MGD).

Some embodiments further include selecting a subject identified as having MGD (e.g., using any of the methods described herein) or having one or more of the physical characteristics described herein for participation in a clinical trial. Some embodiments further include administering to a subject identified as having an eyelid disorder (e.g., MGD) (e.g., using any of the methods described herein) a treatment for MGD (e.g., one or more of any of the treatments described herein, see, e.g., FIG. 30, and/or known in the art).

The methods described herein can be periodically performed (e.g., at least one a month, once every six months, or once a year) on a subject that has an increased risk of developing MGD (e.g., woman in menopause or a subject having androgen deficiency, Sjogren's syndrome, psoriasis, rosacea, hypertension, or benign prostatic hyperplasia, or a subject that is taking or a subject that was previously administered one or more of: an antiandrogen, a postmenopausal hormone therapy (e.g., estrogens and progestins), an antihistamine, an antidepressant, and a retinoid)). Some embodiments further include recording the results of the diagnostic test in the subject's medical records (e.g., recording the results in a computer readable medium), performing a diagnostic test for an eyelid disorder (e.g., MGD) on one or more lineal family members of a subject diagnosed as having an eyelid disorder (e.g., MGD) using the methods described herein, or monitoring one or more lineal family members of a subject diagnosed as having an eyelid disorder (e.g., MGD) using the methods described herein for the development of an eyelid disorder (e.g., MGD) (e.g., using any of the methods described herein).

Methods of Determining the Severity of Meibomian Gland Dysfunction

Provided herein are methods of determining the severity of an eyelid disorder (e.g., MGD) in a subject that include: determining in an eyelid of a subject one or more (e.g., two, three, four, or five) physical characteristics selected from (i) the number and/or density of immune cells in the palpebral conjunctival epithelium, (ii) the number and/or density of immune cells in the palpebral conjunctival substantia propria, (iii) the number, area, and/or density of immune cells present within one or more ducts/ductules in one or more meibomian gland(s) and/or around one or more meibomian glands, (iv) the level of glandular/ductal obstruction in one or more meibomian gland(s), and (v) the size of one or more ducts/ductules present in one or more meibomian gland(s); and comparing the one or more physical characteristics determined in the eyelid of the subject to one or more corresponding reference values, where the determining is performed using methods (e.g., in vivo confocal microscopy) known in the art or described herein, and one or more (e.g., two, three, four, or five) of an elevation in the number and/or density of immune cells in the palpebral conjunctival epithelium, an elevation in the number and/or density of immune cells in the palpebral conjunctival substantia propria, an elevation the number, area, and/or density of immune cells present within one or more ducts/ductules present within one or more meibomian gland(s) and/or around one or more meibomian glands, an elevation in the level of glandular/ductal obstruction in one or more meibomian gland(s), and an elevation in the size of one or more ducts/ductules present in one or more meibomian gland(s), compared to the one or more corresponding reference values, indicates that subject has a severe (e.g., advanced) form or case of an eyelid disorder (e.g., MGD). In some embodiments, the determining is performed using in vivo confocal microscopy.

Some embodiments of these methods include determining, i.e., in an eyelid, of a subject one or more (e.g., one, two, or three) physical characteristics selected from the group of (i) the number, area, and/or density of immune cells present within one or more ducts/ductules within one or more meibomian gland(s) and/or around one or more meibomian glands, (ii) the level of glandular/ductal obstruction in one or more meibomian gland(s), and (iii) the size of one or more ducts/ductules present in one or more meibomian gland(s); and comparing the one or more physical characteristics determined in the eyelid of the subject to one or more corresponding reference values, where one or more (e.g., one, two, or three) of an elevation the number, area, and/or density of immune cells present within one or more ducts/ductules in one or more meibomian gland(s) and/or around one or more meibomian glands, an elevation in the level of glandular/ductal obstruction in one or more meibomian gland(s), and an elevation in the size of one or more ducts/ductules present in one or more meibomian gland(s) in the eyelid of the subject compared to the one or more corresponding reference values, indicates that subject has a severe (e.g., advanced) form or case of an eyelid disorder (e.g., MGD). In some embodiments, these methods further include determining one or more additional physical characteristics selected from the group of the number and/or density of immune cells present in the palpebral conjunctival epithelium, and/or the number and/or density of immune cells present in the palpebral conjunctival substantia propria in the eyelid of the subject; and comparing the one or more additional physical characteristics determined in the eyelid of the subject to one or more corresponding reference values, where one or more of an elevation in the number and/or density of immune cells in the palpebral conjunctival epithelium and an elevation in the number and/or density of immune cells in the palpebral conjunctival substantia propria in the eyelid of the subject compared to the one or more corresponding reference values, indicates that the subject has a severe (e.g., advanced) form or case of an eyelid disorder (e.g., MGD).

In some embodiments of the methods described herein, the reference value is a threshold value (e.g., any of the threshold values described herein. Other exemplary threshold values for the physical characteristics described herein known in the art or can be obtained using methods known in the art. In some embodiments of the methods described herein, the reference value is: the number and/or density of immune cells present in the palpebral conjunctival epithelium, the number and/or density of immune cells present in the palpebral conjunctival substantia propria, the number and/or density of immune cells present within one or more ducts/ductules in one or more meibomian gland(s), the level of glandular/ductal obstruction in one or more meibomian glands, and the size of one or more ducts/ductules present in one or more meibomian gland(s) determined in an eyelid of a healthy subject (e.g., a subject that does not have an eye disease (e.g., a subject that does not have MGD or has not been diagnosed as having MGD). In some embodiments, the subject is not diagnosed as having an allergy and/or does not have an allergy. In some embodiments, the subject is not diagnosed as having atopic keratoconjunctivitis or vernal conjunctivitis, or does not have atopic keratoconjunctivitis or vernal conjunctivitis. In some embodiments, the subject is a woman in menopause or a subject having androgen deficiency, Sjogren's syndrome, psoriasis, rosacea, hypertension, or benign prostatic hyperplasia. In some embodiments, the subject taking or was previously administered one or more of: an anti-androgen, a postmenopausal hormone therapy (e.g., estrogens and progestins), an antihistamine, an antidepressant, or a retinoid. In some embodiments, the subject has a hyposecretory form of MGD (e.g., a condition of decreased meibum delivery due to abnormalities in meibomian glands without remarkable obstruction). In some embodiments, the subject has a hypersecretory form of MGD (e.g., a condition characterized by the release of a large volume of lipid at the lid margin that becomes visible on application of pressure onto the tarsus during examination). In some embodiments, the subject has been diagnosed as having an eyelid disorder (e.g., MGD). In some embodiments, the subject is suspected of having an eyelid disorder (e.g., MGD) or has an increased risk of developing an eyelid disorder (e.g., MGD).

In some embodiments, the methods can be performed by a health care professional (e.g., a physician, a physician's assistant, a nurse, a nurse's assistant, and a laboratory technician). In some embodiments, the subject can be a child, a teenager, or an adult (e.g., at least 18, 20, 25, 30, 35, 40, 45, 50, 55, 60, 65, 70, 75, 80, 85, or 90 years old). A subject can, e.g., present with one or more (e.g., at least two, three, or four) of the symptoms of MGD described herein. In some embodiments, a subject, e.g., may not present with a symptom of MGD that can be easily detected by basic examination of an eye(s) of the subject (examination of the patient that does not involve the magnification of the tissues of the eye).

Some embodiments further include the assessing one or more (e.g., two, three, four, or five) additional symptoms of MGD in the subject (e.g., one or more symptoms of MGD that can be assessed without the aid of an in vivo confocal microscope) (e.g., one or more of dry eyes, pain or a burning sensation in the eyes, increased evaporation, hyperosmolarity, and instability of the tear film, increased bacterial growth on the lid margin, and ocular surface inflammation and damage). Some embodiments further include performing a test to determine tear film quality (e.g., a test to determine tear osmolarity or tear break-up time) or a test to assess corneal damage (e.g., corneal fluorescein staining, Ocular Surface Disease Index (OSDI) scoring, and Dry Eye Questionnaire (DEQ) scoring). Methods for determining tear osmolarity and tear break-up time, and performing corneal fluorescein staining, OSDI scoring, and DEQ scoring are known in the art. In some embodiments, one or more of an elevation in corneal fluorescein staining, tear osmolarity, tear break-up time, OSDI scoring, and DEQ scoring further indicates that the subject has a severe (e.g., advanced) form or case of MGD. Some embodiments further include performing a tear production test (e.g., Schirmer's test), wherein a decrease in tear production as compared to a reference value (e.g., a level of tear production in a healthy subject (e.g., a subject not having an eye disease, e.g., a subject not having MGD)) further indicates that the subject has a severe (e.g., advanced) form or case of an eyelid disorder (e.g., MGD).

Some embodiments further include selecting a subject identified as having MGD (e.g., using any of the methods described herein) or having one or more of the physical characteristics described herein for participation in a clinical trial. Some embodiments further include administering to a subject identified as having an eyelid disorder (e.g., MGD) (e.g., using any of the methods described herein) a treatment for MGD (e.g., one or more of any of the treatments described herein, see, e.g., FIG. 30, and/or known in the art).

The methods described herein can be periodically performed (e.g., at least one a month, once every six months, or once a year) on a subject that has an increased risk of developing MGD (e.g., woman in menopause or a subject having androgen deficiency, Sjogren's syndrome, psoriasis, rosacea, hypertension, or benign prostatic hyperplasia, or a subject that is taking or a subject that was previously administered one or more of: an antiandrogen, a postmenopausal hormone therapy (e.g., estrogens and progestins), an antihistamine, an antidepressant, and a retinoid)). Some embodiments further include recording the results of the test in the subject's medical records (e.g., recording the results in a computer readable medium), performing a diagnostic test for an eyelid disorder (e.g., MGD) on one or more lineal family members of a subject identified as having a mild to severe form of an eyelid disorder (e.g., MGD) using the methods described herein, or monitoring one or more lineal family members of a subject identified as having a mild to severe form of an eyelid disorder (e.g., MGD) using the methods described herein for the development of an eyelid disorder (e.g., MGD) (e.g., using any of the methods described herein).

Methods of Selecting a Subject for Treatment

Provided herein are methods of selecting a subject for treatment of an eyelid disorder (e.g., treatment for MGD) that include: determining in an eyelid of a subject one or more (e.g., two, three, four, or five) physical characteristics selected from the group of (i) the number and/or density of immune cells in the palpebral conjunctival epithelium, (ii) the number and/or density of immune cells in the palpebral conjunctival substantia propria, (iii) the number, area, and/or density of immune cells present within one or more ducts/ductules in one or more meibomian gland(s) and/or around one or more meibomian glands, (iv) the level of glandular/ductal obstruction in one or more meibomian gland(s), and (v) the size of one or more ducts/ductules present in one or more meibomian gland(s); comparing the one or more physical characteristics determined in the eyelid of the subject to one or more corresponding reference values; and selecting a subject having one or more (e.g., two, three, four, or five) of an elevation in the number and/or density of immune cells in the palpebral conjunctival epithelium, an elevation in the number and/or density of immune cells in the palpebral conjunctival substantia propria, an elevation the number, area, and/or density of immune cells present within one or more ducts/ductules in one or more meibomian gland(s) and/or around one or more meibomian glands, an elevation in the level of glandular/ductal obstruction in one or more meibomian gland(s), and an elevation in the size of one or more ducts/ductules present in one or more meibomian gland(s) compared to the one or more corresponding reference values, for treatment of an eyelid disorder (e.g., MGD). In some embodiments, the determining is performed using in vivo confocal microscopy.

Some embodiments of these methods include determining in an eyelid of a subject one or more (e.g., one, two, or three) physical characteristics from the group of (i) the number, area, and/or density of immune cells present within one or more ducts/ductules in one or more meibomian gland(s) and/or around one or more meibomian glands, (ii) the level of glandular/ductal obstruction in one or more meibomian gland(s), and (iii) the size of one or more ducts/ductules present in one or more meibomian gland(s); comparing the one or more physical characteristics determined in the eyelid of the subject to one or more corresponding reference values; and selecting a subject having one or more (e.g., one, two, or three) of an elevation the number, area, and/or density of immune cells present within one or more ducts/ductules in one or more meibomian gland(s) and/or around one or more meibomian gland(s), an elevation in the level of glandular/ductal obstruction in one or more meibomian gland(s), and an elevation in the size of one or more ducts/ductules present in one or more meibomian gland(s), compared to the one or more corresponding reference values, for treatment of an eyelid disorder (e.g., MGD). In some embodiments, these methods further include determining the additional physical characteristics of the number and/or density of immune cells present in the palpebral conjunctival epithelium, and/or the number and/or density of immune cells present in the palpebral conjunctival substantia propria in the eyelid of the subject; comparing one or more of the additional physical characteristics determined in the eyelid of the subject to one or more corresponding reference values; and selecting a subject having one or more of an elevation in the number and/or density of immune cells in the palpebral conjunctival epithelium and an elevation in the number and/or density of immune cells in the palpebral conjunctival substantia propria in the eyelid of the subject compared to the one or more corresponding reference values, for treatment of an eyelid disorder (e.g., MGD).

In some embodiments of the methods described herein, the reference value is a threshold value (e.g., any of the exemplary threshold values described herein or known in the art). In some embodiments of the methods described herein, the reference value is: the number and/or density of immune cells present in the palpebral conjunctival epithelium, the number and/or density of immune cells present in the palpebral conjunctival substantia propria, the number, area, and/or density of immune cells present within one or more ducts/ductules in one or more meibomian gland(s) and/or around one or more meibomian glands, the level of glandular/ductal obstruction in one or more meibomian glands, and the size of one or more ducts/ductules present in one or more meibomian gland(s) determined in the eyelid of a healthy subject (e.g., a subject that does not have an eye disease (e.g., a subject that does not have MGD or has not been diagnosed as having MGD). In some embodiments, the subject is not diagnosed as having an allergy and/or does not have an allergy. In some embodiments, the subject is not diagnosed as having atopic keratoconjunctivitis or vernal conjunctivitis, or does not have atopic keratoconjunctivitis or vernal conjunctivitis. In some embodiments, the subject is a woman in menopause or a subject having androgen deficiency, Sjogren's syndrome, psoriasis, rosacea, hypertension, or benign prostatic hyperplasia. In some embodiments, the subject is taking or was previously administered one or more of: an antiandrogen, a postmenopausal hormone therapy (e.g., estrogens and progestins), an antihistamine, an antidepressant, and a retinoid. In some embodiments, the subject is suspected of having an eyelid disorder (e.g., MGD) or has an increased risk of developing an eyelid disorder (e.g., MGD).

In some embodiments, a subject can be selected for treatment by a health care professional (e.g., a physician, a physician's assistant, a nurse, a nurse's assistant, and a laboratory technician). In some embodiments, the subject selected for treatment can be a child, a teenager, or an adult (e.g., at least 18, 20, 25, 30, 35, 40, 45, 50, 55, 60, 65, 70, 75, 80, 85, or 90 years old). In some embodiments, the subject that is selected can present with one or more (e.g., at least two, three, or four) of the symptoms of MGD described herein. In some embodiments, the subject that is selected may not present with a symptom of MGD that can be easily detected by basic examination of an eye(s) of the subject (examination of the patient that does not involve the magnification of the tissues of the eye).

Some embodiments further include the assessing one or more (e.g., two, three, four, or five) additional symptoms of MGD in the subject (e.g., one or more symptoms of MGD that can be assessed without the aid of an in vivo confocal microscope) (e.g., one or more of dry eyes, pain or a burning sensation in the eyes, increased evaporation, hyperosmolarity, and instability of the tear film, increased bacterial growth on the lid margin, and ocular surface inflammation and damage). Some embodiments further include performing a test to determine tear film quality (e.g., a test to determine tear osmolarity or tear break-up time) or a test to assess corneal damage (e.g., corneal fluorescein staining, Ocular Surface Disease Index (OSDI) scoring, and Dry Eye Questionnaire (DEQ) scoring). Methods for determining tear osmolarity and tear break-up time, and for performing corneal fluorescein staining, OSDI scoring, and DEQ scoring are known in the art. In some embodiments, one or more of an elevation in corneal fluorescein staining, tear osmolarity, tear break-up time, OSDI scoring, and DEQ scoring further indicates that the subject should be selected for treatment of MGD. Some embodiments further include performing a tear production test (e.g., Schirmer's test) in the subject, where a decrease in tear production in the subject as compared to a reference value (e.g., a level of tear production in a healthy subject (e.g., a subject not having an eye disorder, e.g., a subject not having MGD) further indicates that the subject should be selected for treatment of an eyelid disorder (e.g., MGD).

Some embodiments further include selecting the subject for participation in a clinical trial. Some embodiments further include administering a treatment to the subject (e.g., one or more of any of the treatments for MGD described herein, see, e.g., FIG. 30, and/or one or more of the treatments of MGD known in the art).

The methods described herein can be periodically performed (e.g., at least one a month, once every six months, or once a year) on a subject that has an increased risk of developing an eyelid disorder (e.g., MGD) (e.g., woman in menopause or a subject having androgen deficiency, Sjogren's syndrome, psoriasis, rosacea, hypertension, or benign prostatic hyperplasia, or a subject that is taking or a subject that was previously administered one or more of: an antiandrogen, a post-menopausal hormone therapy (e.g., estrogens and progestins), an anti-histamine, an antidepressant, or a retinoid)).

Some embodiments further include recording the results of the test in the subject's medical records (e.g., recording the recommendation of a treatment for an eyelid disorder (e.g., MGD) for the subject in a computer readable medium), performing a diagnostic test for an eyelid disorder (e.g., MGD) on one or more lineal family members of a subject selected for treatment of an eyelid disorder (e.g., MGD) using the methods described herein, or monitoring one or more lineal family members of a subject selected for treatment of an eyelid disorder (e.g., MGD) using the methods described herein for the development of an eyelid disorder (e.g., MGD) (e.g., using any of the methods described herein).

Methods for Determining Efficacy of Treatment of Meibomian Gland Dysfunction

Provided herein are methods of determining the efficacy of treatment of an eyelid disorder (e.g., MGD) in a subject. These methods include (a) determining in an eyelid of a subject having an eyelid disorder (e.g., MGD) one or more (e.g., two, three, four, or five) physical characteristics from the group of (i) the number and/or density of immune cells in the palpebral conjunctival epithelium, (ii) the number and/or density of immune cells in the palpebral conjunctival substantia propria, (iii) the number, area, and/or density of immune cells present within one or more ducts/ductules in one or more meibomian gland(s) and/or around one or more meibomian glands, (iv) the level of glandular/ductal obstruction in one or more meibomian gland(s), and (v) the size of one or more ducts/ductules present in one or more meibomian gland(s) at a first time point; (b) determining in the eyelid of the subject the one or more (e.g., two, three, four, or five) physical characteristics at a second time point; and (c) comparing the one or more (e.g., two, three, four, or five) physical characteristics determined at the first and second time points, where (i) the first time point is prior to treatment and the second time point is any time point following the initiation of treatment, or (ii) the first time point is following the initiation of treatment and the second time point is a later time point during or after treatment, and one or more (e.g., two, three, four, or five) of (i) a decrease in the number and/or density of immune cells in the palpebral conjunctival epithelium, (ii) a decrease in the number and/or density of immune cells in the palpebral conjunctival substantia propria, (iii) a decrease in the number, area, and/or density of immune cells present within one or more ducts/ductules in one or more meibomian gland(s) and/or around one or/more meibomian glands, (iv) a decrease in the level of glandular/ductal obstruction in one or more meibomian gland(s), and (v) a decrease in the size of one or more ducts/ductules present in one or more meibomian gland(s) determined at the second time point compared to the first time point indicates that the treatment was effective in the subject. In some embodiments, the determining in (a) and (b) is performed using in vivo confocal microscopy.

Some embodiments of these methods include (a) determining in an eyelid of a subject having an eyelid disorder (e.g., MGD) one or more (e.g., two or three) of (i) the number, area, and/or density of immune cells present within one or more ducts/ductules in one or more meibomian gland(s) and/or around one or more meibomian glands, (ii) the level of glandular/ductal obstruction in one or more meibomian gland(s), and (iii) the size of one or more ducts/ductules present in one or more meibomian gland(s) at a first time point; (b) determining in the eyelid of the subject one of more of (i) the number, area, and/or density of immune cells present within one or more ducts/ductules in one or more meibomian gland(s) and/or around one or more meibomian glands, (ii) the level of glandular/ductal obstruction in one or more meibomian gland(s), and (iii) the size of one or more ducts/ductules present in one or more meibomian gland(s) at a second time point; and (c) comparing the one or more of (i) the number, area, and/or density of immune cells present within one or more ducts/ductules in one or more meibomian gland(s) and/or around one or more meibomian glands, (ii) the level of glandular/ductal obstruction in one or more meibomian gland(s), and (iii) the size of one or more ducts/ductules present in one or more meibomian gland(s) determined at the first and second time points, where (i) the first time point is prior to treatment and the second time point is any time point following the initiation of treatment, or (ii) the first time point is following the initiation of treatment and the second time point is a later time point during or after treatment, and one or more (e.g., two or three) of (i) a decrease in the number, area, and/or density of immune cells present within one or more ducts/ductules in one or more meibomian gland(s) and/or around one or more meibomian glands, (ii) a decrease in the level of glandular/ductal obstruction in one or more meibomian gland(s), and (iii) a decrease in the size of one or more ducts/ductules present in one or more meibomian gland(s) determined at the second time point compared to the first time point indicates that the treatment was effective in the subject. In some embodiments, the determining in (a) and (b) is performed using in vivo confocal microscopy.

Some embodiments further include (d) determining in the eyelid of the subject having an eyelid disorder (e.g., MGD) one or more of the number and/or density immune cells in the palpebral conjunctival epithelium, and the number and/or density of immune cells in the palpebral conjunctival substantia propria at the first time point; (e) determining in the eyelid of the subject one or more of the number and/or density of immune cells in the palpebral conjunctival epithelium, and the number and/or density of immune cells in the palpebral conjunctival substantia propria, at the second time point; and (f) comparing the one or more of the number and/or density of immune cells in the palpebral conjunctival epithelium, and the number and/or density of immune cells in the palpebral conjunctival substantia propria, determined at the second time point compared to the first time point further indicates that the treatment was effective in the subject. In some embodiments, the subject's positive response to the treatment is recorded in the subject's medical records (e.g., recorded in a computer readable medium).

Alternatively, in the above methods, a subject that has one or more (e.g., two, three, four, five, or six) of a decrease or no substantial change in the number and/or density of immune cells in the palpebral conjunctival epithelium, a decrease or no substantial change in the number and/or average density of immune cells in the palpebral conjunctival substantia propria, a decrease or no substantial change in the number, area, and/or density of immune cells within one or more ducts/ductules in one or more meibomian gland(s) and/or around one or more meibomian cells, a decrease or no substantial change in the level of glandular/ductal obstruction in one or more meibomian gland(s), and a decrease or no substantial change in the size in one or more ducts/ductules present in one or more meibomian glands determined at the second time point compared to the first time point, indicates that the treatment was not effective in the subject. In some embodiments, the subject's negative or neutral response to the treatment is recorded in the subject's medical records (e.g., recorded in a computer readable medium).

Some embodiments, where the treatment has been indicated to be ineffective in the subject, further include administering, recommending, or prescribing an alternate treatment to the subject. In some embodiments, the alternate treatment can be a different therapeutic agent or a different combination of one or more therapeutic agents. In some embodiments, the alternate treatment can be an increased dosage of one or more therapeutic agents currently being taken by the subject, an increase in the frequency of administration of one or more therapeutic agents currently being taken by the subject, or an alteration in the route of delivery of one or more therapeutic agents being currently taken by the subject.

In some embodiments, the amount of time between the first and the second time point can be at least one week (e.g., at least two weeks, three weeks, one month, two months, three months, four months, six months, or one year).

In some embodiments, the subject is not diagnosed as having an allergy and/or does not have an allergy. In some embodiments, the subject is not diagnosed as having atopic keratoconjunctivitis or vernal conjunctivitis, or does not have atopic keratoconjunctivitis or vernal conjunctivitis. In some embodiments, the subject is a woman in menopause or a subject having androgen deficiency, Sjogren's syndrome, psoriasis, rosacea, hypertension, and benign prostatic hyperplasia. In some embodiments, the subject is taking or was previously administered one or more of: an antiandrogen, a post-menopausal hormone therapy (e.g., estrogens and progestins), an anti-histamine, an antidepressant, or a retinoid. In some embodiments, the subject is suspected of having an eyelid disorder (e.g., MGD) or is at risk of developing an eyelid disorder (e.g., MGD).

In some embodiments, the method is performed by a health care professional (e.g., a physician, a physician's assistant, a nurse, a nurse's assistant, and a laboratory technician). In some embodiments, the subject is a child, a teenager, or an adult (e.g., at least 18, 20, 25, 30, 35, 40, 45, 50, 55, 60, 65, 70, 75, 80, 85, or 90 years old). In some embodiments, the subject does not present with a symptom of MGD that can be observed without the use of a microscope. In some embodiments, the subject has a form of MGD that is refractory to previous therapeutic treatment. In some embodiments, the subject has had MGD for at least one week (e.g., at least two weeks, three weeks, one month, two months, three months, four months, six months, or one year). In some embodiments, the subject presents with one or more symptoms of an eyelid disorder (e.g., MGD) described herein.

Some embodiments further include the assessing one or more (e.g., two, three, four, or five) additional symptoms of MGD in the subject (e.g., one or more symptoms of MGD that can be assessed without the aid of an in vivo confocal microscope) (e.g., one or more of dry eyes, pain or a burning sensation in the eyes, increased evaporation, hyperosmolarity, and instability of the tear film, increased bacterial growth on the lid margin, and ocular surface inflammation and damage) at the first and/or the second time point, and optionally comparing the number of symptoms or the severity of the one or more symptoms of MGD at the second time point to the number of symptoms or the severity of the one or more symptoms of MGD at the second time point to the number of symptoms or the severity of symptoms of one or more symptoms of MGD at the first time point, where a decrease in the number of symptoms or a decrease in the severity of one or more symptoms of MGD further indicates that the treatment was effective. Some embodiments further include performing a tear production test (e.g., Schirmer's test) at the first and/or second time point, where an elevation in tear production at the second time point compared to the first time point further indicates that the treatment was effective.

Some embodiments further include performing a test to determine tear film quality (e.g., a test to determine tear osmolarity or tear break-up time) or a test to assess corneal damage (e.g., corneal fluorescein staining, Ocular Surface Disease Index (OSDI) scoring, and Dry Eye Questionnaire (DEQ) scoring) at the first and/or second time points, and optionally, comparing the tear film quality or corneal damage determined at the second time point to the tear film quality or corneal damage determined at the first time point, where an increase in the tear film quality or a decrease in corneal damage determined at the second time point compared to the tear film quality or corneal damage determined at the first time point further indicates that the treatment was effective. Methods for determining tear osmolarity and tear break-up time, and for performing corneal fluorescein staining, OSDI scoring, and DEQ scoring are known in the art.

In some embodiments, the subject is a female (e.g., a post-menopausal female). In some embodiments, the subject is a male. In some embodiments, the subject is already receiving a treatment for MGD, the subject terminates the previous treatment for MGD, and the efficacy of a new treatment is determined using the methods described herein. In some embodiments, the subject is already receiving a treatment for MGD, the subject begins to take one or more additional (new) therapeutic agent(s) in combination with the old treatment, and the efficacy of the combination of the one or more additional (new) therapeutic agents and the old treatment are determined using the methods described above. In some embodiments, the subject is already receiving one or more therapeutic agent(s) for MGD, and the efficacy of an increased dosage and/or an increased frequency of dosing of the previously administered one or more therapeutic agent(s) is determined using the methods described herein. In some embodiments, the subject is already receiving one or more therapeutic agent(s) for MGD, and the efficacy of an alternative route of administration of the one or more therapeutic agent(s) previously administered to the subject is determined using the methods described above.

Some embodiments further include administering a treatment (e.g., one or more therapeutic agents) to the subject between the first and second time points (e.g., one or more of any of the treatments for MGD described herein and/or one or more of the treatments of MGD known in the art). Some embodiments further include administering a treatment to the subject prior to the first time point. Some embodiments further include determining one or more (e.g., two, three, four, or five) of the number and/or density of immune cells in the palpebral conjunctival epithelium, the number and/or density of immune cells in the palpebral conjunctival substantia propria, the number, area, and/or density of immune cells present within one or more ducts/ductules in one or more meibomian gland(s) and/or around meibomian glands, the level of glandular/ductal obstruction in one or more meibomian gland(s), and the size of one or more ducts/ductules present in one or more meibomian gland(s) in the eyelid of the subject at one or more additional time points (e.g., after the second time point). In some embodiments, the one or more additional time points occur after the end of the therapeutic treatment.

The methods described herein can be periodically performed (e.g., at least once every two weeks, once a month, once every six weeks, once every eight weeks, once every six months, or once a year) on a subject that is receiving a treatment for MGD. Some embodiments further include performing a diagnostic test for an eyelid disorder (e.g., MGD) on one or more lineal family members of the subject, or monitoring one or more lineal family members of the subject using the methods described herein for the development of an eyelid disorder (e.g., MGD) (e.g., using any of the methods described herein).

Selecting a Subject for Participation in a Clinical Study

Also provided are methods of selecting a subject for participation in a clinical study (e.g., an asymptomatic subject or a subject having MGD). These method include determining in an eyelid of a subject one or more (e.g., two, three, four, or five) of (i) the number and/or density of immune cells in the palpebral conjunctival epithelium, (ii) the number and/or density of immune cells in the palpebral conjunctival substantia propria, (iii) the number, area, and/or density of immune cells present within one or more ducts/ductules in one or more meibomian gland(s) and/or around one or more meibomian glands, (iv) the level of glandular/ductal obstruction in one or more meibomian gland(s), and (v) the size of one or more ducts/ductules present in one or more meibomian gland(s); comparing the one or more of (i) the number and/or density of immune cells in the palpebral conjunctival epithelium, (ii) the number and/or density of immune cells in the palpebral conjunctival substantia propria, (iii) the number, area, and/or density of immune cells present within one or more ducts/ductules within one or more meibomian gland(s) and/or around one or more meibomian glands, (iv) the level of glandular/ductal obstruction in one or more meibomian gland(s), and (v) the size of one or more ducts/ductules present in one or more meibomian gland(s), determined in the eyelid of the subject to one or more corresponding reference values; and selecting a subject having one or more (e.g., two, three, four, or five) of an elevation in the number and/or density of immune cells in the palpebral conjunctival epithelium, an elevation in the number and/or density of immune cells in the palpebral conjunctival substantia propria, an elevation the number, area, and/or density of immune cells present within one or more ducts/ductules in one or more meibomian gland(s) and/or around one or more meibomian glands, an elevation in the level of glandular/ductal obstruction in one or more meibomian gland(s), and an elevation in the size of one or more ducts/ductules present in one or more meibomian gland(s), compared to the one or more corresponding reference values, for participation in a clinical study. In some embodiments, the determining is performed using in vivo confocal microscopy.

In some embodiments of the methods described herein, the reference value is a threshold value. In some embodiments of the methods described herein, the reference value is: the number and/or density of immune cells present in the palpebral conjunctival epithelium, the number and/or density of immune cells present in the palpebral conjunctival substantia propria, the number, area, and/or density of immune cells present within one or more ducts/ductules in one or more meibomian gland(s) and/or around one or more meibomian glands, the level of glandular/ductal obstruction in one or more meibomian glands, or the size of one or more ducts/ductules present in one or more meibomian gland(s) determined in an eyelid of a healthy subject (e.g., a subject that does not have an eye disease (e.g., a subject that does not have MGD or has not been diagnosed as having MGD)). In some embodiments, the subject is not diagnosed as having an allergy and/or does not have an allergy. In some embodiments, the subject is not diagnosed as having atopic keratoconjunctivitis or vernal conjunctivitis. In some embodiments, the subject has been diagnosed as having hyperproductive MGD or hypoproductive MGD. In some embodiments, the subject is undiagnosed or does not present with one or more symptoms of MGD. In some embodiments, the subject is a woman in menopause or a subject having androgen deficiency, Sjogren's syndrome, psoriasis, rosacea, hypertension, or benign prostatic hyperplasia. In some embodiments, the subject is taken or was previously administered one or more of: an antiandrogen, a postmenopausal hormone therapy (e.g., estrogens and progestins), an anti-histamine, an antidepressant, and a retinoid. In some embodiments, the subject is suspected of having an eyelid disorder (e.g., MGD) or has an increased risk of developing an eyelid disorder (e.g., MGD).

In some embodiments, a subject is selected for participation in a clinical study by a health care professional (e.g., a physician, a physician's assistant, a nurse, a nurse's assistant, and a laboratory technician). In some embodiments, the subject that is selected can be a child, a teenager, or an adult (e.g., at least 18, 20, 25, 30, 35, 40, 45, 50, 55, 60, 65, 70, 75, 80, 85, or 90 years old). In some embodiments, the subject that is selected can present with one or more (e.g., at least two, three, or four) of the symptoms of MGD described herein. In some embodiments, the subject selected may not present with a symptom of MGD that can be easily detected by basic examination of an eye(s) of the subject (examination of the patient that does not involve the magnification of the tissues of the eye).

Some embodiments further include the assessing one or more (e.g., two, three, four, or five) additional symptoms of MGD in the subject (e.g., one or more symptoms of MGD that can be assessed without the aid of an in vivo confocal microscope) (e.g., one or more of dry eyes, pain or a burning sensation in the eyes, increased evaporation, hyperosmolarity, and instability of the tear film, increased bacterial growth on the lid margin, and ocular surface inflammation and damage). Some embodiments further include performing a test to determine tear film quality (e.g., a test to determine tear osmolarity or tear break-up time) and/or a test to assess corneal damage (e.g., corneal fluorescein staining, Ocular Surface Disease Index (OSDI) scoring, and Dry Eye Questionnaire (DEQ) scoring) in the subject. Methods for determining tear osmolarity and tear break-up time, and for performing corneal fluorescein staining, OSDI scoring, and DEQ scoring are known in the art. In some embodiments, a subject having one or more of an elevation in corneal fluorescein staining, tear osmolarity, tear break-up time, OSDI scoring, and DEQ scoring is selected for participation in a clinical study.

Some embodiments further include recording the results of the method in the subject's medical records (e.g., recording the selection of the subject for participation in a clinical trial in a computer readable medium), performing a diagnostic test for an eyelid disorder (e.g., MGD) on one or more lineal family members of a subject selected for participation in a clinical trial using the methods described herein, or monitoring one or more lineal family members of a subject selected for participation in a clinical trial using the methods described herein for the development of an eyelid disorder (e.g., MGD) (e.g., using any of the methods described herein).

Methods of Treating a Subject

Also provided are methods of treating a subject (e.g., a subject having an eyelid disorder, e.g., MGD) that include selectively administering (e.g., oral or topical administration) to a subject (e.g., a subject having MGD), determined to have an elevated number or density of immune cells in the palpebral conjunctival substantia propria as compared to a reference level, at least one (e.g., two, three, or four) oral anti-inflammatory antimicrobial agent (e.g., doxycycline or azithromycin), and/or selecting performing meibomian gland probing on a subject (e.g., a subject having MGD), determined to have an elevation in the level of glandular/ductal obstruction in one or more meibomian gland(s) compared to a reference level. In some embodiments, the subject presents with (has) one or more symptoms of an eyelid disorder (e.g., MGD) described herein. In some embodiments, the subject has been diagnosed as having an eyelid disorder (e.g., MGD). In some embodiments, the subject is suspected of having an eyelid disorder (e.g., MGD) or has an increased risk of developing an eyelid disorder (e.g., MGD). For example, a subject as risk of developing an eyelid disorder is a subject that wears contact lenses or has a lineal family member with an eyelid disorder.

Some embodiments further include one or more of: determining the level of the number or density of immune cells in the palpebral substantia propria and/or the level of glandular/ductal obstruction in one or more meibomian gland(s) (e.g., using in vivo confocal microscopy); comparing level of the number or density of immune cells in the palpebral conjunctival substantia propria and/or the level of glandular/ductal obstruction in one or more meibomian gland(s) in the subject to a reference level; and selecting a subject having an elevated number or density of immune cells in the palpebral conjunctival substantia propria and/or an elevated level of glandular/ductal obstruction in one or more meibomian gland(s) as compared to the reference level for treatment. Some embodiments further include selecting a subject having an eyelid disorder (e.g., MGD).

In some embodiments, these methods are performed by a medical professional (e.g., a physician, a physician's assistant, a nurse, a nurse's assistant, and a laboratory technician). In some embodiments, the subject may already be taking one or more pharmaceutical agents for treatment of MGD, and the subject is instructed or advised to discontinue taking one or more of the previously prescribed one or more pharmaceutical agents. In some embodiments, the subject may already be taking one or more pharmaceutical agents for treatment of MGD, and the at least one oral anti-inflammatory antimicrobial agent is administered to the subject in combination with the one or more pharmaceutical agents previously taken by the subject.

In some embodiments, the reference level can be a threshold level or can be number or average density of immune cells present in the palpebral conjunctival substantia propria in a healthy subject (e.g., a subject that does not have one or more symptoms of MGD or a subject that has not been diagnosed as having an eye disease (e.g., MGD)) or the same subject at an earlier time point.

In some embodiments, the at least one oral anti-inflammatory antimicrobial agent is selected from the group of: azithromycin, doxycycline, clarithromycin, dirithromycin, erythromycin, roxithromycin, telithromycin, carbomycin A, josamycin, kitasamycin, midecamycin, oleandomycin, solithomycin, spiramycin, troleandomycin, and tylocine. In some embodiments, the oral anti-inflammatory antimicrobial agent is doxycycline or azithromycin.

Additional examples of oral anti-inflammatory antimicrobial agents (anti-inflammatory antimicrobial agents that can be administered orally to a subject) that can used in the methods described herein are known in the art. In some embodiments, the at least one oral anti-inflammatory antimicrobial agent is administered to the subject at least once a day (e.g., at least twice, three times, or four times a day). In some embodiments, the at least one oral anti-inflammatory antimicrobial agent is administered to the subject in the morning or with food. In some embodiments, the subject is further administered artificial tears (e.g., Lipiflow treatment (TearScience)).

In some embodiments, meibomian gland probing is a procedure that includes the decompression of one or more meibomian gland(s) (e.g., one or more occluded or obstructed meibomian glands) with a cannula. In some embodiments, the probing procedure further includes a lavage of the decompressed meibomian gland with a physiologically acceptable solution (e.g., a pharmaceutically acceptable solution or medium). A variety of pharmaceutically acceptable solutions/media are known in the art (e.g., phosphate buffered saline). Additional examples of meibomian gland probing procedures are known in the art (see, e.g., Maskin, Cornea 29:1145-1152, 2010). Multiple rounds of meibomian gland probing can be performed on a subject (e.g., one or more rounds of meibomian gland probing on different dates).

The invention is further described in the following example, which does not limit the scope of the invention described in the claims.

EXAMPLES

Example 1

In Vivo Confocal Microscopic Study of Eyelid Tissues in Control Subjects and Subjects having MGD An in vivo confocal microscopy study of eyelid tissues from control (healthy) subjects and subjects having meibomian gland dysfunction (MGD) was performed. In these experiments, clinical examination of the eye and in vivo confocal microscopic imaging of the eyelid was performed on subjects having MGD prior to and/or after treatment with an orally administered anti-inflammatory antibiotic (e.g., pre-treatment or post-treatment, respectively) (see, FIG. 1). Some of the patients having MGD in this study were previously administered a treatment that did not result in a change in the symptoms of MGD. The demographics of the subjects in this study are shown in Table 1.

TABLE 1

Demographics of study participants

| Group | Sex Ratio (F:M) | Age (mean ± SD yrs) | OSDI (mean ± SD) | Corneal Staining (mean ± SD) | TBUT (s) (mean ± SD s) |
|---|---|---|---|---|---|
| Normals | 2:3 | 37 ± 11 | N/A | 0 ± 0 | ≥10 |
| MGD | 8:3 | 52 ± 16 | 40 ± 13 | 1 ± 0.7 | 5 ± 2 |

In vivo confocal microscopy was used to image a variety of eyelid tissue morphological features including but not limited to cells, tissue layers, meibomian glands, sub-anatomical structures, and blood and lymph vessels present in the eyelid of each subject. In these studies, in vivo confocal microscopy was used to quantitatively determine the epithelial immune cell density, stromal (substantia propria) immune cell density, the percentage luminal area occupied by immune cells, periglandular immune cell density, the ductal basement membrane thickness, meibomian gland ductal luminal dimensions (e.g., breadth), meibomian gland acinar density, and meibomian gland acinar epithelial thickness. Qualitatively, stromal fibrosis and vascularity of the eyelid tissue were also assessed. The meibomian gland acinar density, meibomian gland acinar epithelial thickness, palpebral conjunctival epithelial immune cell density, palpebral conjunctival stromal immune cell density, luminal area occupied by intraglandular immune cells, periglandular immune cell density, and the ductal basement membrane thickness were determined for each subject based on an analysis of the in vivo confocal microscopic image(s) gathered for each subject at one or more time point(s).

Figure 2:
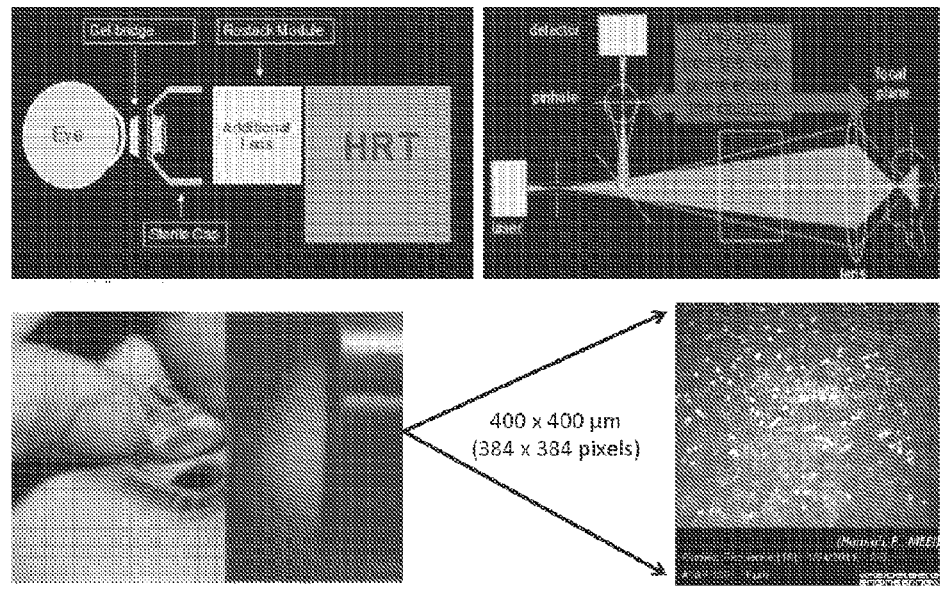
FIG. 2 is a set of three diagrams. The upper left diagram shows the general (exemplary) positioning of an in vivo confocal microscope (e.g., HRT) relative to the subject's eye when structures of the cornea are imaged. The upper right diagram shows the exemplary positioning of the laser, the lens, and the detector in an in vivo confocal microscope. The bottom diagram generally depicts the methods used in the present study: the folding back (everting) of an eyelid of a subject, the contacting of the lens of the in vivo confocal microscope to the eyelid of the subject, and the resulting image of the subject's eyelid tissue gathered using the in vivo confocal microscope.

In vivo confocal microscopy was performed as generally diagramed in FIG. 2. In these studies, a laser scanning in vivo confocal microscopy (Heidelberg Retina Tomograph 3 with the Rostock Cornea Module, Heidelberg Engineering GmbH, Dossenheim, Germany) was used to image the eyelid tissues of each subject. The laser-scanning microscope used a 670-nm red wavelength diode laser source and was equipped with a 63× objective immersion lens with a numerical aperture of 0.9 (Olympus, Tokyo, Japan). The laser-scanning confocal microscope provided images, each of which represents an image sequence of the eyelid measuring 400×400 μm, which is 160,000 μm$^2$ at a selected depth, and separated from adjacent images by approximately 1 to 4 μm with a lateral resolution of 1 μm/pixel. Digital images were stored on a computer workstation at 30 frames per second. A disposable sterile polymethylmethacrylate cap (Tomo-Cap; Heidelberg, Engineering GmbH, Dossenheim, Germany) filled with a layer of hydroxypropyl methylcellulose 2.5% (GenTeal gel; Novartis Ophthalmics, East Hanover, N.J.) in the bottom, was mounted in front of the eyelid module optics for each examination. One drop of topical anesthesia 0.5% proparacaine hydrochloride (Alcaine; Alcon, Fort Worth, Tex.) was instilled in both eyes, followed by a drop of hydroxypropyl methylcellulose 2.5% (GenTeal gel, Novartis Ophthalmics) in the fornices of both eyes. One drop of hydroxypropyl methylcellulose 2.5% was also placed on the outside tip of the cap to improve optical coupling. The tip of the cap was manually advanced towards each patient's folded-back (everted) eyelid until the gel contacted the subject's eyelid.

A total of six to eight sequence and/or volume scans were obtained from an eyelid of the subject, typically at a depth of 10 to 80 μm. Representative image(s) (at least 2-3 images per parameter) were selected for analysis. The criteria used to select the images were the best focused images, visualization of the structure(s) of interest, with the whole image in the same layer, without motion, without folds, and good contrast. ImageJ was used to analyze the obtained images. The specific imaging parameters used in these experiments are listed in Table 2 below.

TABLE 2

Parameters and respective depths

| Imaging parameter (units) | Significance | Method |
| --- | --- | --- |
| Acinar density (acini/mm$^2$) | Density of meibomian glands' meibum-producing units indicating glandular dropout if any. | Number of glandular acini per region of interest per frame. Measured at less than 50 μm depth. |
| Acinar epithelial thickness (μm) | Epithelial proliferation or atrophy of meibum-producing glandular units. | (Total external length of acinus–total internal luminal length of acinus in same plane)/2. |
| Epithelial immune cell density (cells/mm$^2$) | Location and extent of inflammation. | Number of immune cells per region of interest per frame. Measured at less than 30 μm depth. |
| Stromal immune cell density (cells/mm$^2$) | Location and extent of inflammation. | Number of immune cells per region of interest per frame. Measured at between 35-90 μm depth. |
| Periglandular immune cell area (μm$^2$) | Location and extent of inflammation. | Area occupied by immune cells around the duct of a meibomian gland per frame. Measured at between 35-90 μm depth. |
| Periglandular immune cell density (cells/mm$^2$) | Location and extent of inflammation. | Number of immune cells in the area occupied by them around the duct of a meibomian gland per frame. Measured at between 35-90 μm depth. |
| % luminal plugging by intraglandular immune cells (%) | Extent and infiltration of inflammation. | (Area occupied by immune cells within lumen of gland/total luminal area of gland) × 100. Measured at between 30-90 μm depth. |
| Length of ducts with immune cells (μm) | Morphological and possible functional changes in gland. | Total longitudinal internal luminal length of duct. Measured at between 30-90 μm depth. |
| Width of ducts with immune cells (μm) | Morphological and possible functional changes in gland. | Total horizontal internal luminal width of duct. Measured at between 30-90 μm depth. |
| Basement membrane thickness of ducts with immune cells (μm) | Reactive proliferative or atrophic activity within duct. | (Total external length of duct—total internal luminal length of duct in same plane)/2. Measured at between 30-90 μm depth. |
| Length of ducts without immune cells (μm) | Morphological and possible functional changes in gland. | Total longitudinal internal luminal length of duct. Measured at between 30-90 μm depth. |
| Width of ducts without immune cells (μm) | Morphological and possible functional changes in gland. | Total horizontal internal luminal width of duct. Measured at between 30-90 μm depth. |
| Basement membrane thickness of ducts without immune cells (μm) | Reactive proliferative or atrophic activity within duct. | (Total external length of duct—total internal luminal length of duct in same plane)/2. Measured at between 30-90 μm depth. |

Figure 3:
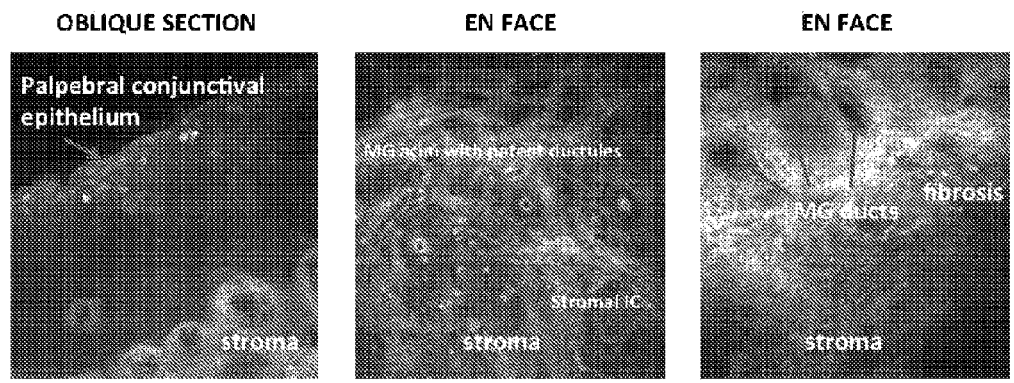
FIG. 3 is a set of three in vivo confocal micrographs. From left to right is shown: an oblique image of a normal subject's eyelid showing the palpebral conjunctival epithelium and the stroma; an en face image of a normal subject's eyelid showing meibomian gland acini with patent ductules, the stroma, and a few stromal immune cells present within the stroma; and an en face image of a normal subject's eyelid showing meibomian gland ducts, fibrosis surrounding the meibomian gland ducts, and the stroma.
Figure 4:
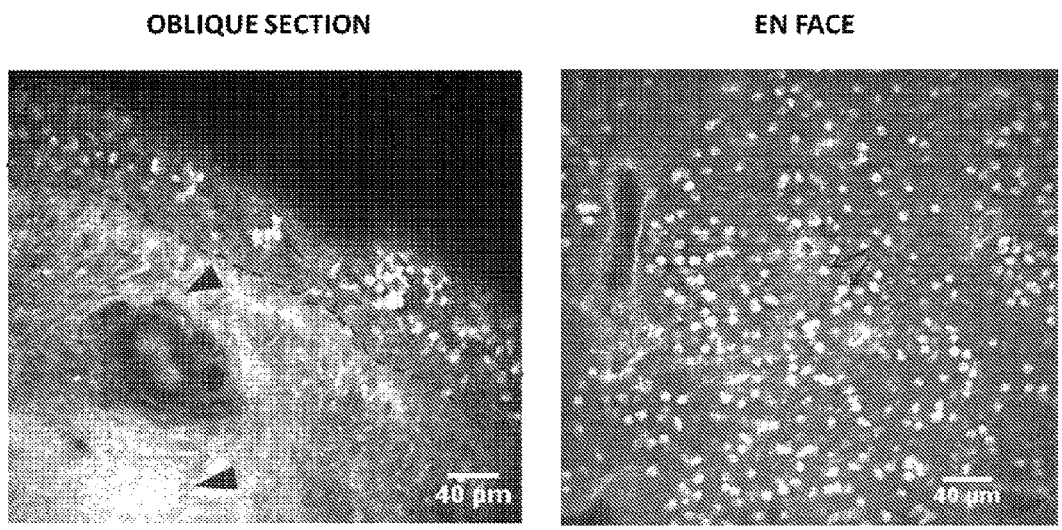
FIG. 4 is a set of two in vivo confocal micrographs: an oblique image (left) and an en face image (right) of an eyelid from a subject with MGD showing epithelial immune cells in the subject's eyelid.
Figure 5:
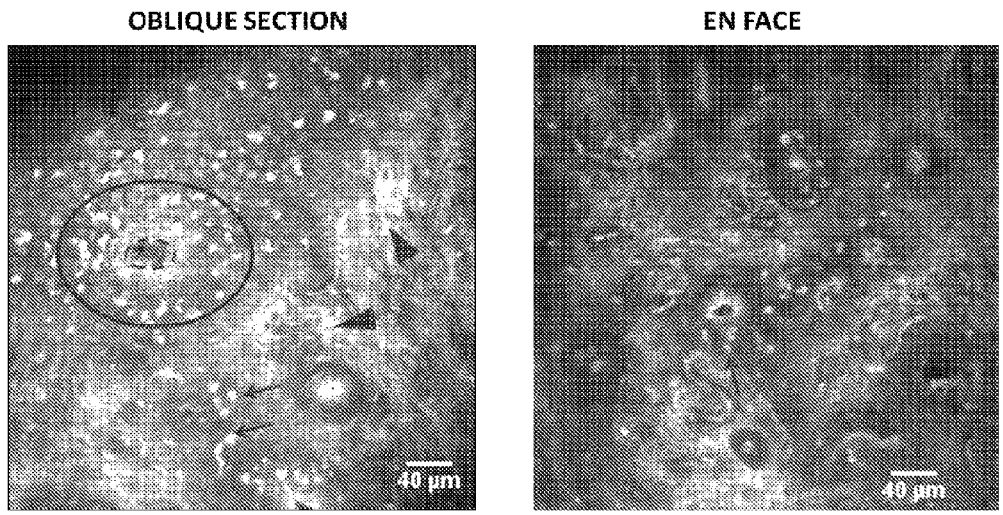
FIG. 5 is a set of two in vivo confocal micrographs: an oblique image (left) and an en face image (right) of an eyelid from a subject with MGD showing stromal immune cells (periglandular) in the subject's eyelid.

FIG. 3 shows a set of in vivo confocal micrographs gathered from normal (control) subjects that demonstrate the ability of this imaging method to detect a variety of structures within the eyelid of subjects (e.g., the palpebral conjunctival epithelium (conjunctival epithelium of the eyelid), meibomian gland acini with patent ductules, the stroma (palpebral conjunctival substantia propria), stromal immune cells, meibomian gland ducts, and fibrosis within the eyelid). In vivo confocal microscopy can also detect the number and density of epithelial immune cells, and stromal immune cell density, periglandular immune cell area, and stromal fibrosis in subjects having MGD (see, e.g., FIGS. 4 and 5, respectively).

Figure 6:
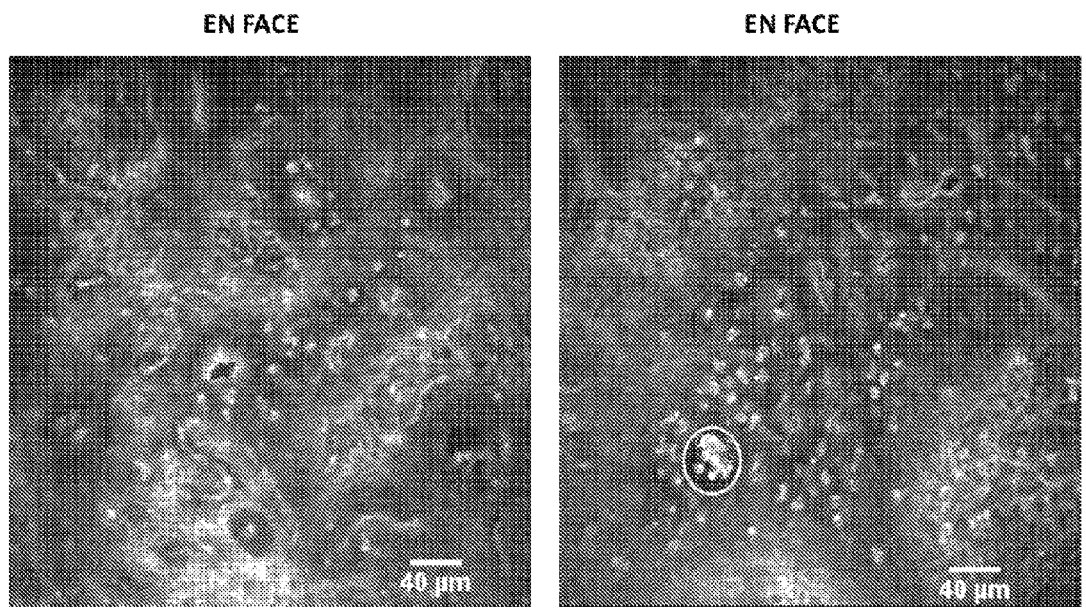
FIG. 6 is a set of two in vivo confocal micrographs: an en face image of an eyelid from a control subject (left) and an en face image of an eyelid from a subject with MGD (right). A comparison of these two microscopic images indicates the changes in the intraglandular area occupied by immune cells and luminal dimensions that occur in the meibomian glands of a subject having MGD as compared to a healthy (control) subject.

A side-by-side comparison of images from a control subject and a subject having MGD (prior to treatment) show that a subject having MGD (prior to treatment) has an elevated percent luminal intraglandular area occupied by immune cells, an elevated ductal membrane thickness, and increased luminal dimensions as compared to the levels detected in the control subject (see, e.g., FIG. 6).

Figure 7:
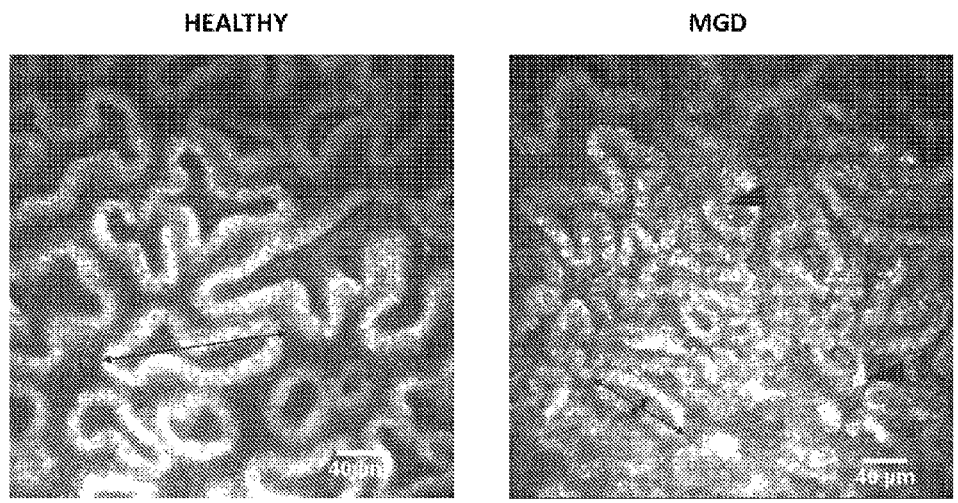
FIG. 7 is a set of two in vivo confocal micrographs: an image of an eyelid from a healthy (control) subject (left), and an image of an eyelid from a subject having MGD (right) that show meibomian gland acini. A comparison of these two images indicates the changes in the acinar density, the appearance of acinar epithelium, luminal reflectance, the external and internal dimensions of acini, and the epithelial thickness of acini that occur in meibomian glands of a subject having MGD as compared to a healthy (control) subject.
Figure 8:
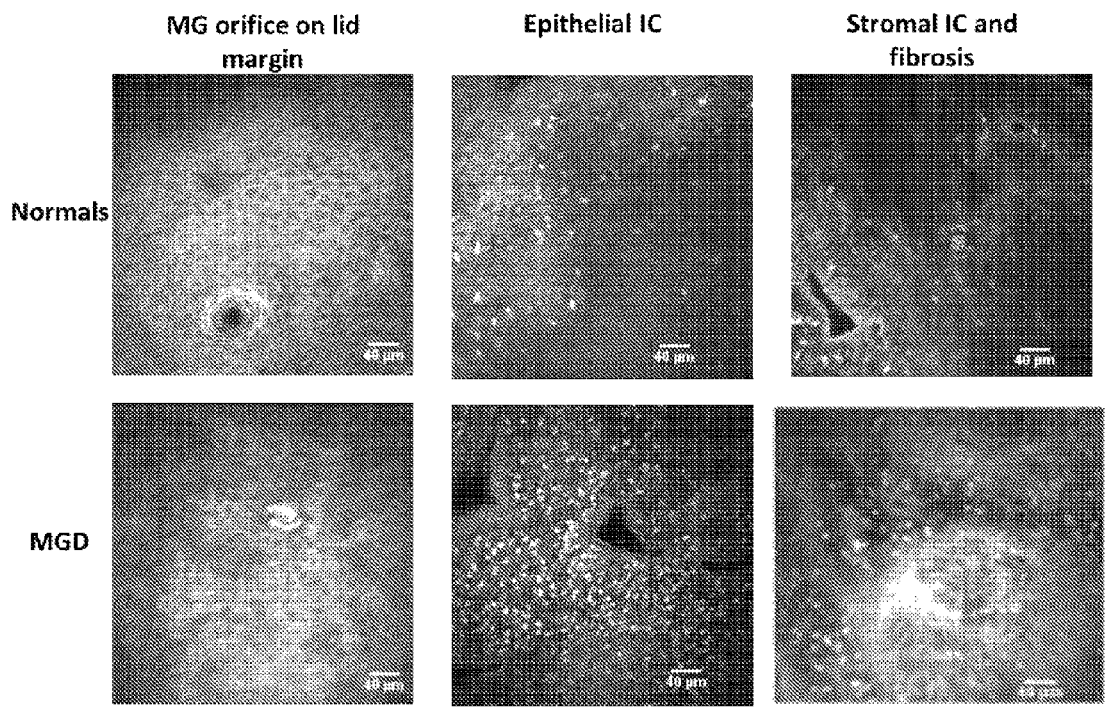
FIG. 8 is a set of five in vivo confocal micrographs: three images of eyelids of normal (healthy) subjects (top row) and three images of eyelids from subjects having MGD (bottom row) that show the meibomian gland orifice at the lid margin (left two images), epithelial immune cells (center two images), and stromal immune cells and fibrosis of the meibomian gland (right two images).

A side-by-side comparison of images from a control subject and a subject having MGD (prior to treatment) show that a subject having MGD (prior to treatment) has a decrease in acinar density, a decrease in external and internal acinar dimensions, and an increase in acinar epithelial thickness compared to the levels detected in the control subject (see, e.g., FIG. 7). An additional side-by-side comparison of images from a control subject and a subject having MGD (prior to treatment) show that a subject having MGD (prior to treatment) has plugging of meibomian gland orifices on the lid margin, an elevated number or density of epithelial immune cells, an elevated number or density of stromal immune cells, and an increased level of fibrosis as compared to a normal (control) subject (see, e.g., FIG. 8). Plugging of meibomian gland orifices on the lid margin suggests that a subject having MGD has one or more obstructed meibomian glands.

Figure 9:
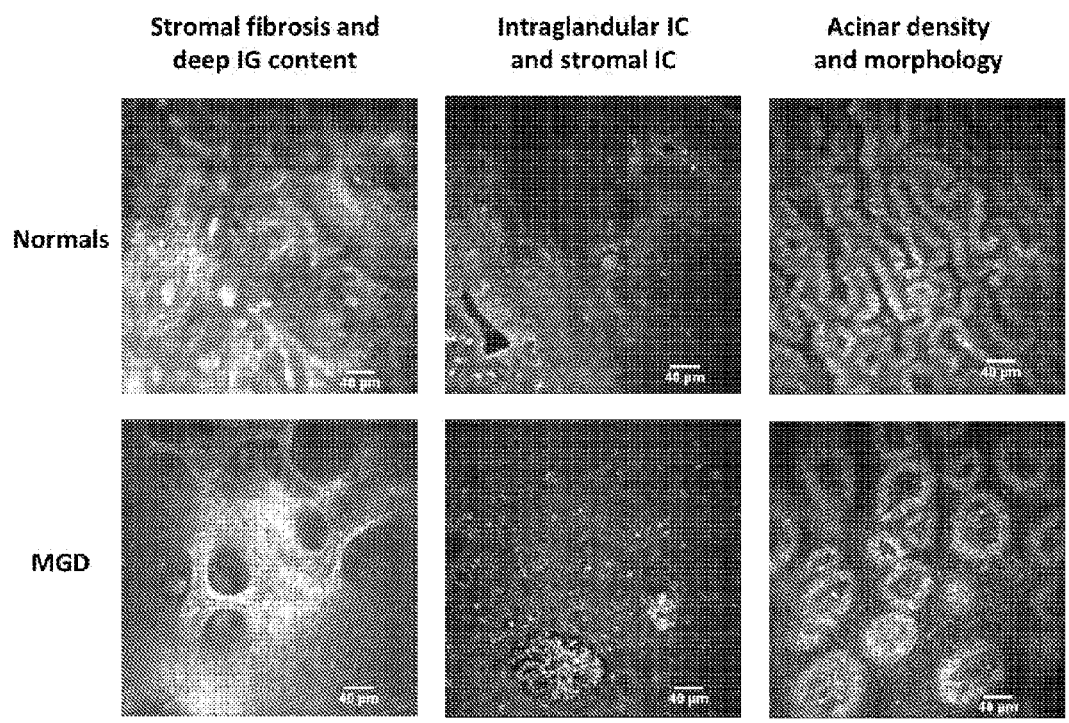
FIG. 9 is a set of six in vivo confocal micrographs: three images of eyelids of normal (healthy) subjects (top row) and three images of eyelids from subjects having MGD (bottom row) that show stromal fibrosis and deep intraglandular (IG) content (left two images), intraglandular immune cells and stromal immune cells (center two images), and acinar density and morphology (right two images).
Figure 14:
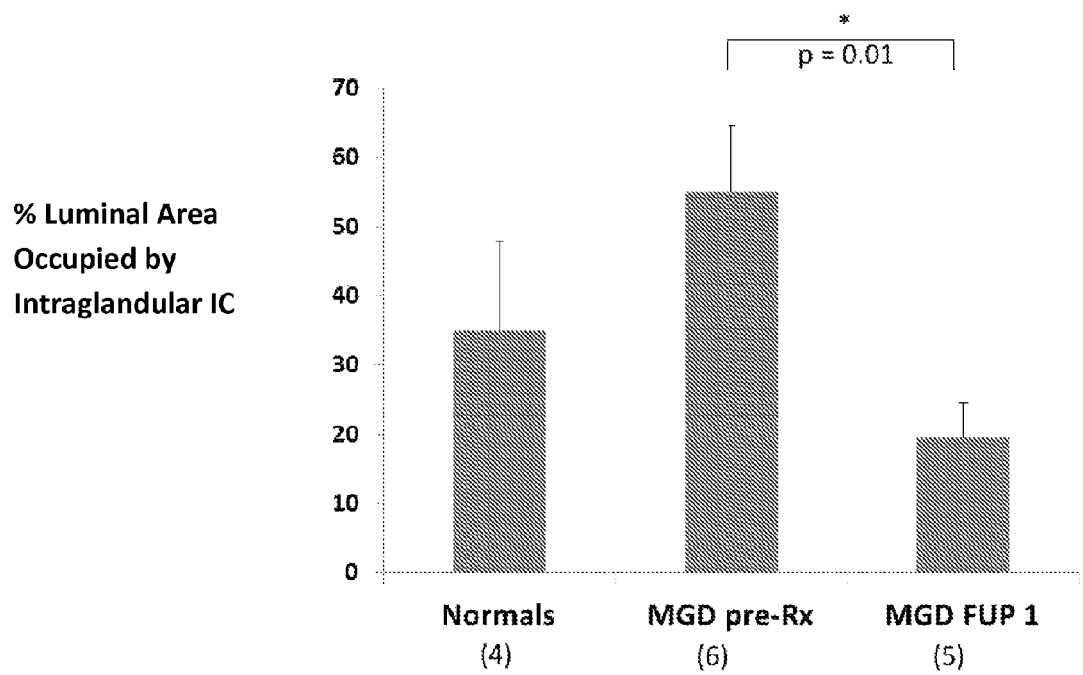
FIG. 14 is a graph showing the percent meibomian gland luminal area occupied by intraglandular immune cells in normal (control) subjects (n=4), subjects having MGD prior to treatment (MGD pre-Rx; n=6), and subjects having subjects having MGD following treatment (MGD FUP 1; n=5).

A comparison of a different set of images from a control subject and a subject having MGD (prior to treatment) show that a subject having MGD has an elevated level of stromal fibrosis, elevated deep immune cell content, an elevated number, area, or density of intraglandular immune cells, an elevated number or density of stromal (substantia propria) immune cells, a decrease in the density and/or size of acini, increased thickness of acinar epithelium, and an alteration in acini morphology as compared to a normal (healthy) subject (see, e.g., FIG. 9).

cells is decreased in MGD subjects following treatment as compared to MGD subjects prior to treatment (FIG. 14).

Figure 15:
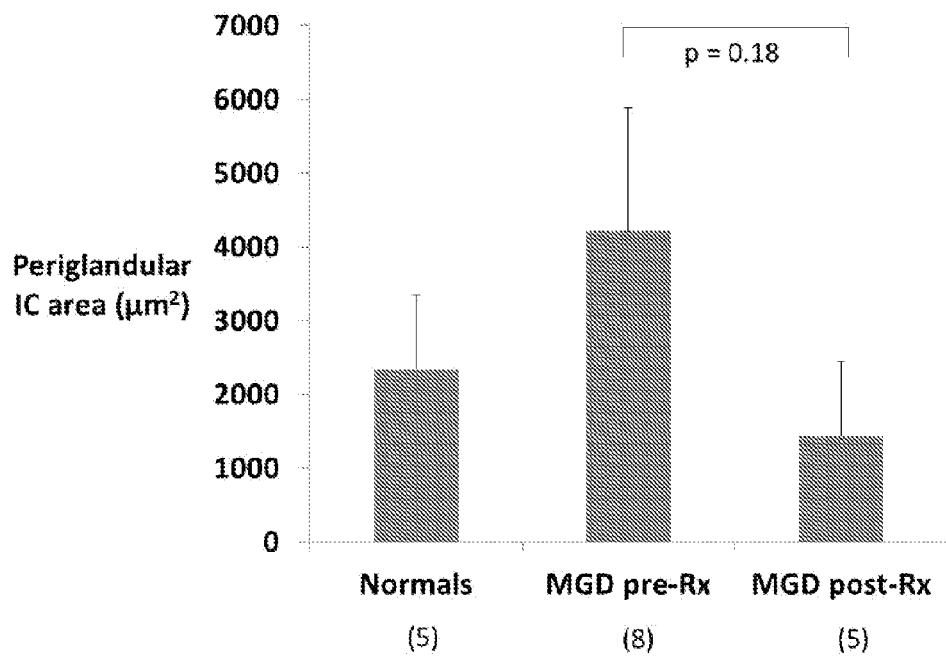
FIG. 15 is a graph showing the periglandular (meibomian gland) immune cell area (μm$^2$) in normal (control) subjects (n=5), subjects having MGD prior to treatment (MGD pre-Rx; n=8), and subjects having MGD following treatment (MGD FUP 1; n=5). The data shown are the mean±SEM.

The periglandular immune cell area was also examined in control (healthy) subjects and MGD subjects. These resulting data show that MGD subjects (prior to treatment) have an elevated (increased) periglandular immune cell area as compared to normal (healthy) subjects, and that MGD subjects following treatment have a decreased periglandular immune cell area as compared to MGD subjects prior to treatment (FIG. 15).

Figure 16:
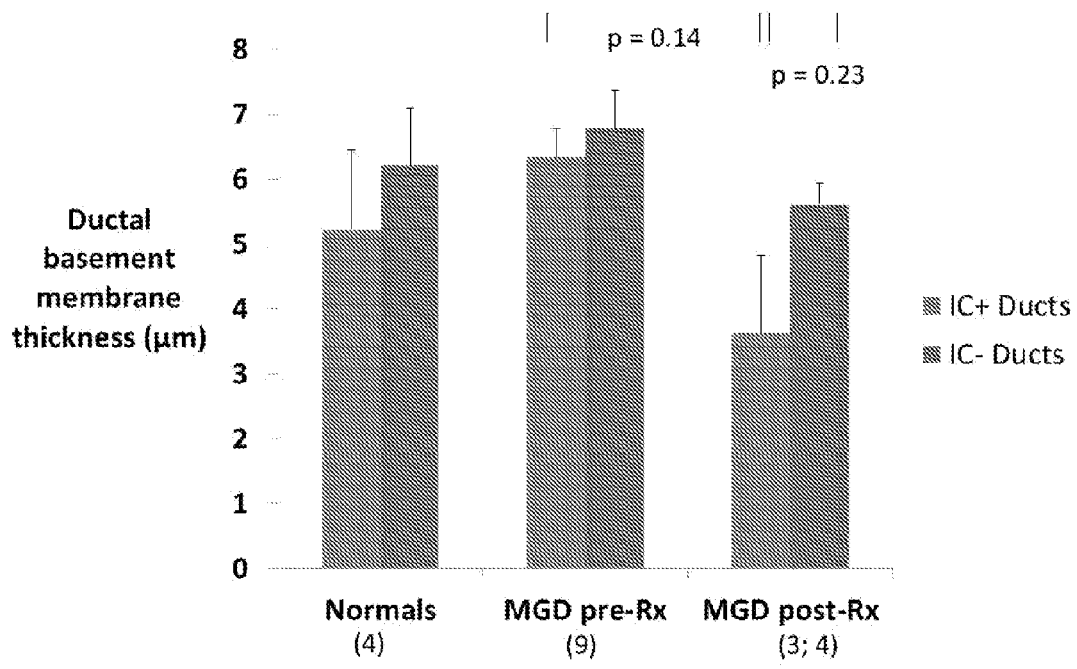
FIG. 16 is a graph showing the meibomian gland ductal basement membrane thickness (μm) in immune cell-positive (IC+) ducts (left bar in each grouping) and in immune cell-negative (IC−) ducts (right bar in each grouping) from normal (control) subjects (n=4 for both IC+ and IC− ducts), subjects having MGD prior to treatment (MGD pre-Rx; n=9 for both IC+ and IC− ducts) and subjects having MGD following treatment (MGD FUP 1; n=3 for IC+ ducts, and n=4 for IC− ducts). The data shown are the mean±SEM.

Ductal basement membrane thickness was also assessed in the control (healthy) subjects and MGD subjects. The data show that MGD subjects following treatment have a decrease in ductal membrane thickness as compared to MGD subjects prior to treatment (FIG. 16). Table 3 (below) lists the mean epithelial immune cell density, stromal immune cell density, intraglandular immune cell density, periglandular immune cell density, acinar density, and acinar epithelial thickness for the normal (healthy) subject. MGD subjects prior to treatment, and MGD subjects following treatment.

TABLE 3

Palpebral conjunctival and glandular immune response in normal (healthy) subjects, and MGD subjects pre- and post-anti-inflammatory therapy

| Imaging Parameter | Normals | MGD Pre-Treatment | p-value | MGD Post-treatment | p-value |
|---|---|---|---|---|---|
| Epithelial IC Density (cells/mm$^2$; mean ± SD) | 278 ± 203 | 576 ± 285 | 0.03 | 162 ± 191 | 0.003 |
| Stromal IC Density (cells/mm$^2$; mean ± SD) | 100 ± 79 | 118 ± 139 | 0.74 | 17 ± 23 | 0.04 |
| Intraglandular IC (% lumenal area occupied; mean ± SD) | 35 ± 26 | 55 ± 23 | 0.3 | 19 ± 12 | 0.01 |
| Periglandular IC area (mm$^2$; mean ± SD) | 0.002 ± 0.002 | 0.004 ± 0.005 | 0.36 | 0.001 | 0.18 |
| Acinar Density (acini/mm$^2$; mean ± SD) | 127 ± 48 | 76 ± 43 | 0.08 | 115 ± 44 | 0.18 |
| Acinar Epithelial Thickness (μm; mean ± SD) | 15 ± 3 | 19 ± 3 | 0.04 | 21 ± 4 | 0.59 |

Figure 10:
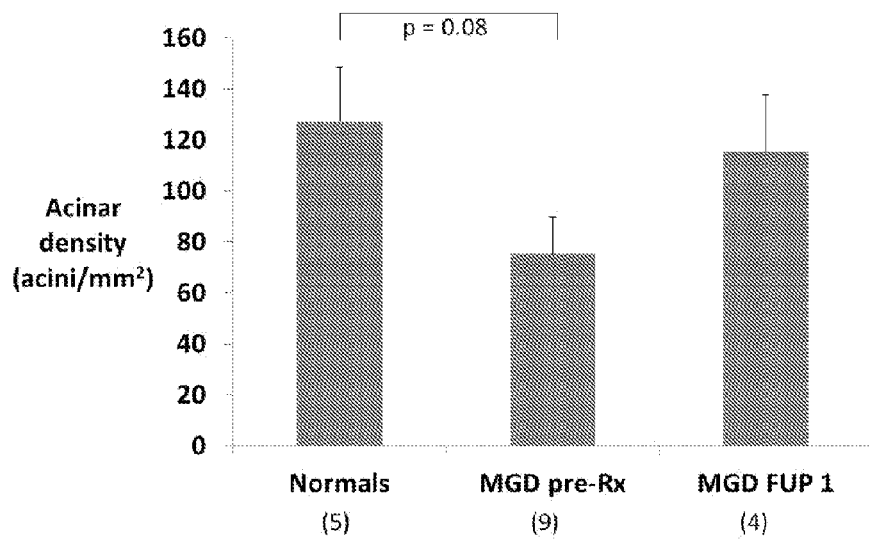
FIG. 10 is a graph showing the meibomian gland acinar density (acini/mm$^2$) in normal (control) subjects (n=5), subjects having MGD prior to treatment (MGD pre-Rx; n=9), and subjects having MGD following treatment (MGD FUP 1; n=4). The data shown are the mean±standard error of the mean (SEM).
Figure 11:
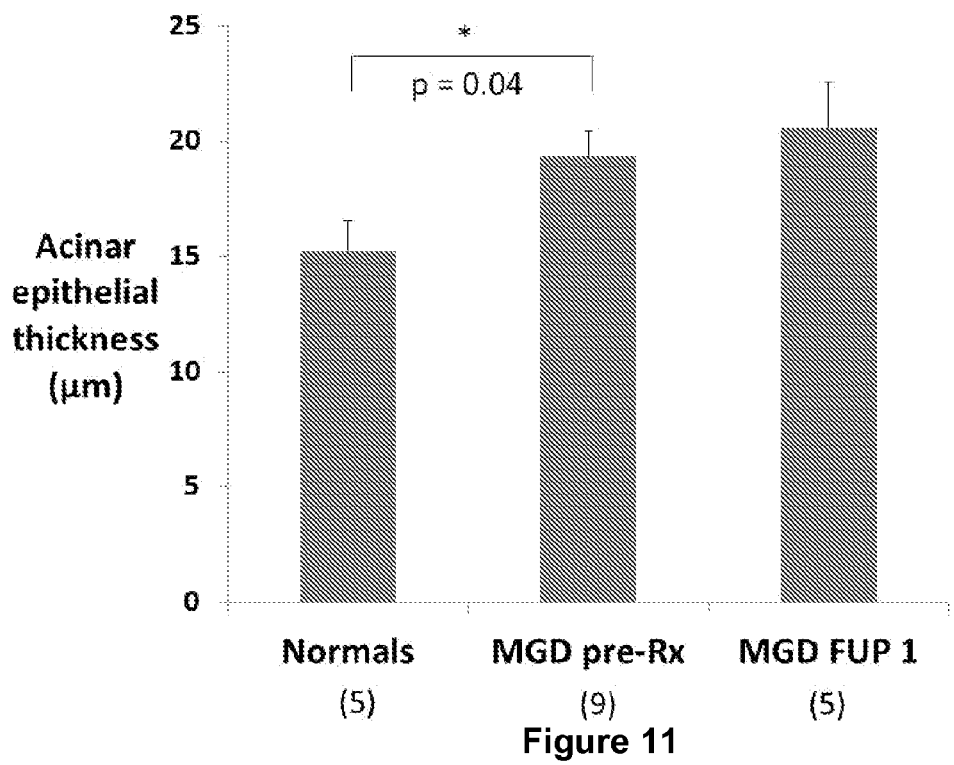
FIG. 11 is a graph showing the meibomian gland acinar epithelial thickness (μm) in normal (control) subjects (n=5), subjects having MGD prior to treatment (MGD pre-Rx; n=9), and subjects having MGD following treatment (MGD FUP 1; n=5). The data shown are the mean±SEM.
Figure 12:
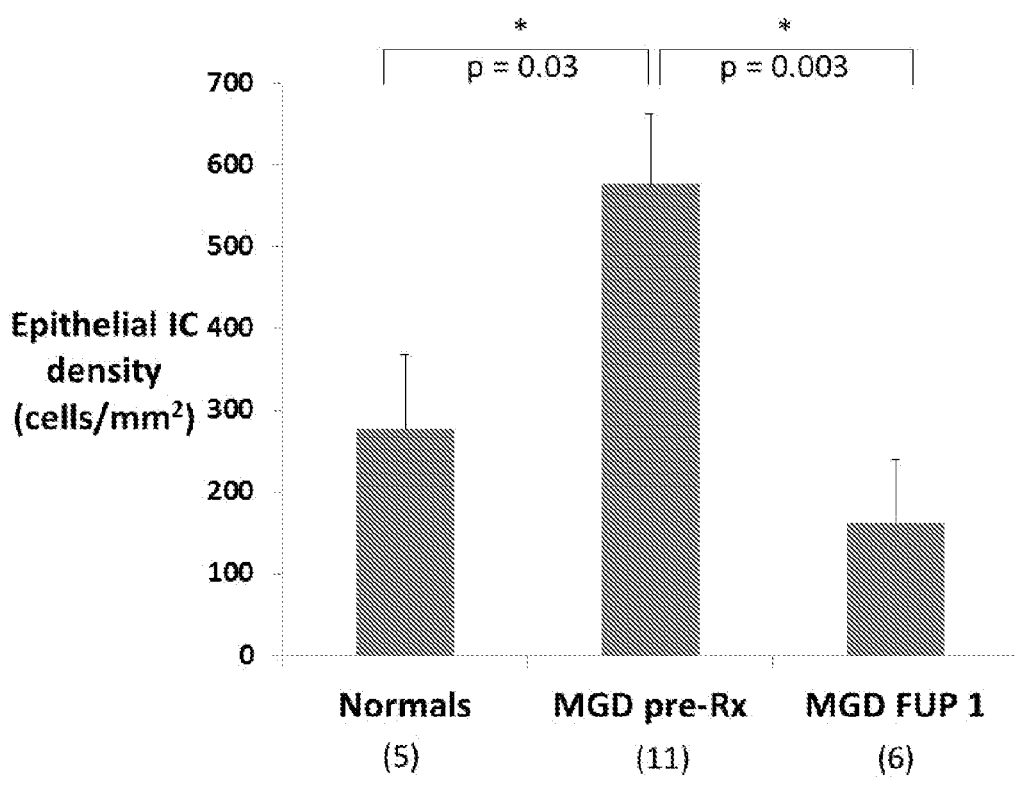
FIG. 12 is a graph showing the epithelial immune cell density (cells/mm$^2$) in the eyelid of normal (control) subjects (n=5), subjects having MGD prior to treatment (MGD pre-Rx; n=11), and subjects having MGD following treatment (MGD FUP 1; n=6). The data shown are the mean±SEM.

The resulting data gathered from normal (healthy) subjects, subjects having MGD prior to treatment (MGD pre-Rx), and subjects having MGD following systemic treatment with an anti-inflammatory antibiotic (MGD FUP-1) show that subjects having MGD have decreased acinar density compared to normal subjects, and an elevation in acinar density in MGD subjects following treatment as compared to MGD subjects prior to treatment (FIG. 10). The data also show that subjects having MGD have an increase in acinar epithelial thickness compared to normal (control) subjects (FIG. 11), that MGD subjects (prior to treatment) have an elevated palpebral conjunctival epithelial immune cell density compared to control (healthy) subjects (FIG. 12), and that MGD subjects following treatment have decreased palpebral conjunctival epithelial immune cell density compared to MGD subjects prior to treatment (FIG. 12).

Figure 13:
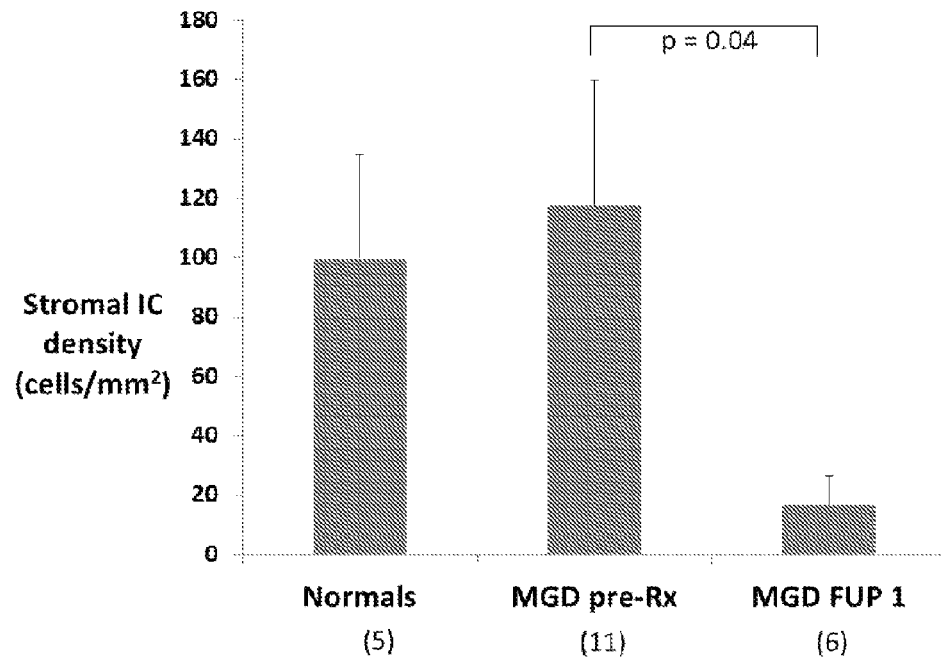
FIG. 13 is a graph showing the stromal immune cell density (cells/mm$^2$) in the eye lids of normal (control) subjects (n=5), subjects having MGD prior to treatment (MGD pre-Rx; n=11), and subjects having MGD following treatment (MGD FUP 1; n=6). The data shown are the mean±SEM.

The data further show that palpebral conjunctival stromal (substantia propria) immune cell density is decreased in MGD subjects following treatment as compared to MGD subjects prior to treatment (FIG. 13). In addition, the data reveal that the percent luminal area occupied by intraglandular immune cells is elevated in MGD subjects prior to treatment compared to control (healthy) subjects, and that the percent luminal area occupied by intraglandular immune cells is decreased in MGD subjects following treatment as compared to MGD subjects prior to treatment (FIG. 14).

The resulting data indicate that a subject can be diagnosed as having MGD by determining one of more the number and/or density of immune cells in the palpebral conjunctival epithelium, the number and/or density of immune cells in the palpebral conjunctival substantia propria, the number, area, and/or density of immune cells present within one or more ducts/ductules in one or more meibomian gland(s) and/or around one or more meibomian glands, the level of glandular/ductal obstruction in one or more meibomian gland(s), and the size of one or more acini and/or ducts/ductules present in one or more meibomian gland(s) in an eyelid of a subject using in vivo confocal microscopy, where one or more of an elevation in the number and/or density of immune cells in the palpebral conjunctival epithelium, an elevation in the number and/or density of immune cells in the palpebral conjunctival substantia propria, an elevation in the number, area, and/or density of immune cells present within one or ducts/ductules in one or more meibomian gland(s) and/or around one or more meibomian glands, an elevation in the level of glandular/ductal obstruction in one or more meibomian gland(s), and an elevation in the size of one or more acini and/or ducts/ductules present in one or more meibomian gland(s) in the subject compared to the one or more corresponding reference values (e.g., a level from a subject not having an eye disease (e.g., a subject not having MGD), indicates that the subject has MGD.

Figure 17:
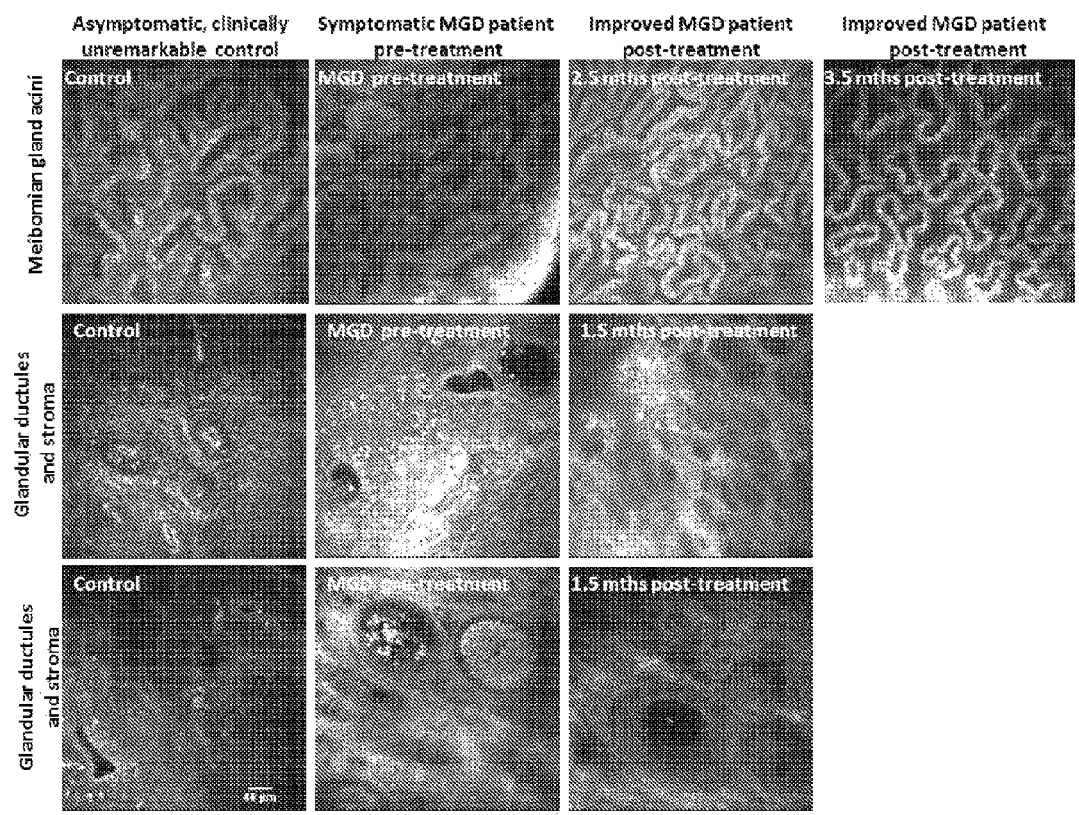
FIG. 17 is a set of ten in vivo confocal micrographs of eyelids of control (healthy) subjects (left three images), subjects with symptomatic MGD prior to treatment (center left images), and subjects having MGD after treatment that show improvement (center right images and right images) that show meibomian gland acini (top row), and glandular ductules and stroma (center and bottom rows).
Figure 18:
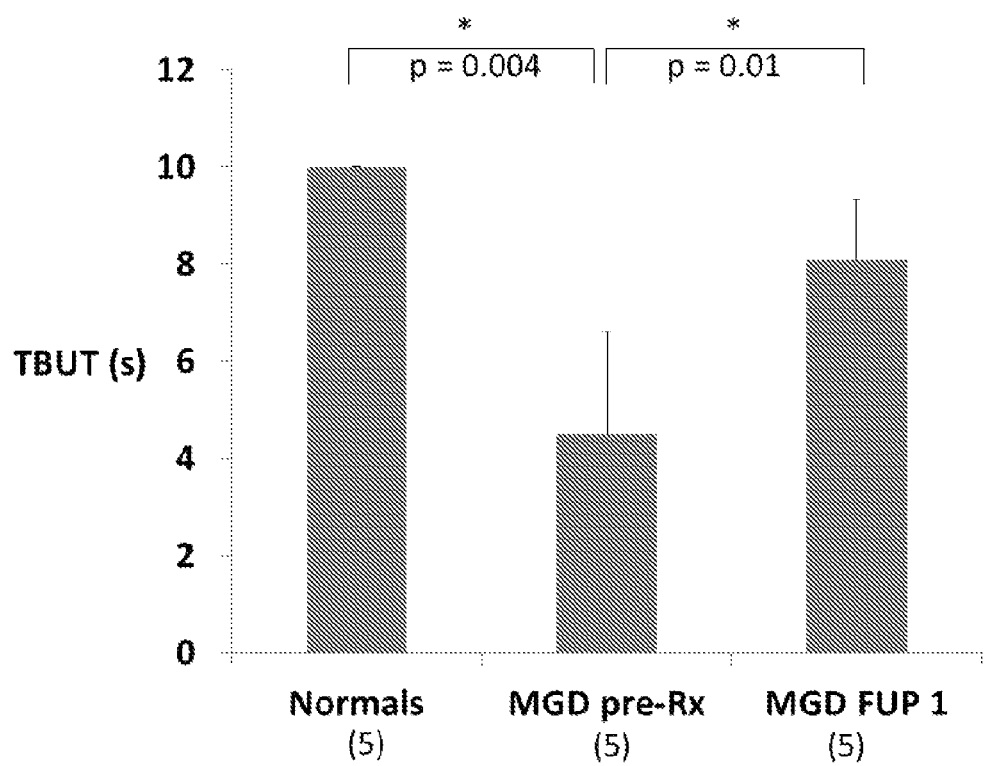
FIG. 18 is a graph showing the tear break-up time (TBUT) in normal (control) subjects (n=5), subjects with MGD prior to treatment (n=5), and subjects with MGD following treatment (MGD FUP 1; n=5). The data shown are the mean±SEM.

The meibomian gland acini, meibomian glandular ductules, and stroma of the eyelid in control (healthy) patients, subjects with symptomatic MGD prior to treatment, and subjects having MGD after treatment that show improvement were compared. The data indicate that subjects that have received successful treatment of MGD have a reduced number, area, or density of immune cells present within one or more ducts/ductules of one or more meibomian glands and/or around one or more meibomian glands, a decrease in the level of glandular/ductal obstruction in one or more meibomian gland(s), an increase in the size or area one or more acini, a decrease in acinar epithelial thickness, a decrease in ductal dimensions, increased heterogeneity of acinar morphology, and a decrease in the size or area of one or more ducts/ductules present in one or more meibomian gland(s) compared to the levels present in a control (healthy) subject (FIG. 17).

The above described changes in the one or more eyelid structures as measured using in vivo confocal microscopy also correlated with other assessments of the severity of MGD in a subject. Tear break-up time (TBUT) was calculated in normal subjects, subjects having MGD prior to treatment, and subjects having MGD following treatment. The data show that subjects having MGD (prior to treatment) have a decreased TBUT compared to control (healthy subjects), and subjects having MGD following treatment have an increased TBUT compared to MGD subjects prior to treatment. There was progressive improvement in symptom severity as evident by decreasing (OSDI) scores from the first follow-up visit to the second follow-up visit.

Figure 19:
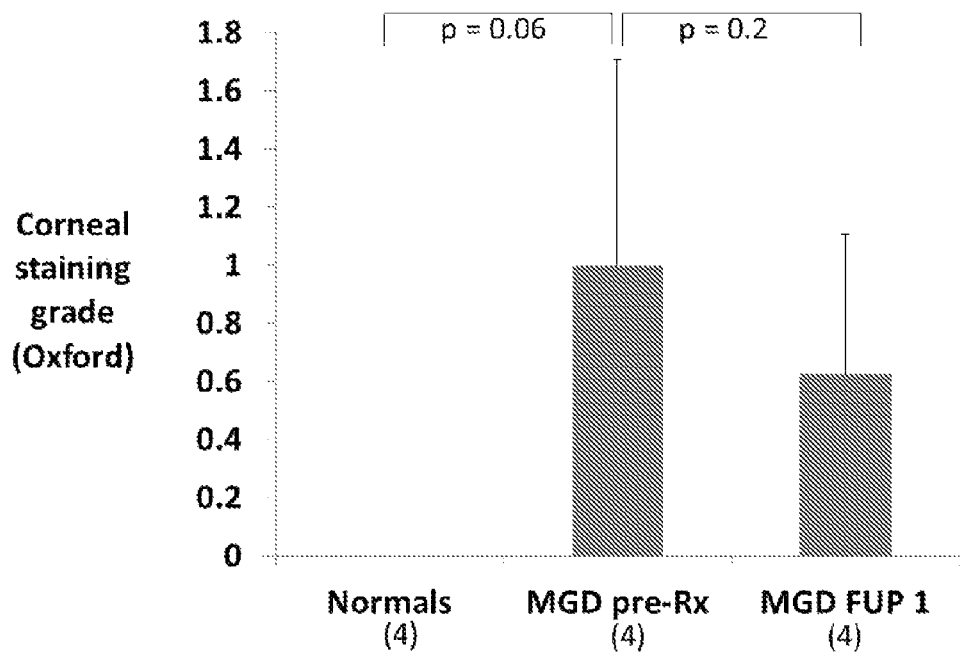
FIG. 19 is a graph showing the corneal staining grade (Oxford) in normal (control) subjects (n=4), subjects with MGD prior to treatment (n=4), and subjects with MGD following treatment (MGD FUP 1; n=4). The data shown are the mean±SEM.
Figure 20:
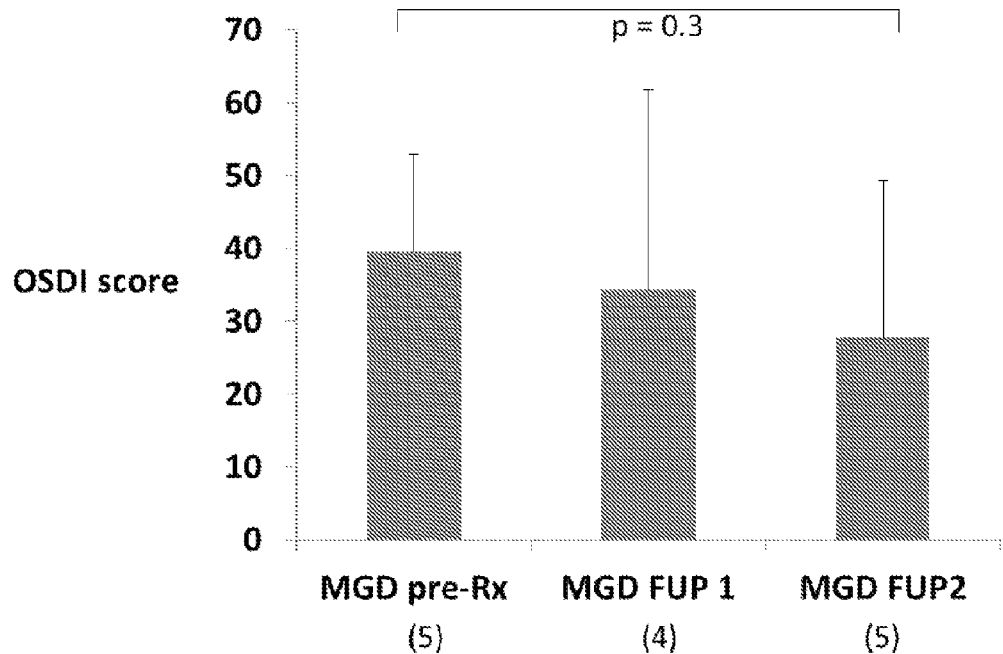
FIG. 20 is a graph showing the ocular surface disease index (OSDI) score in subjects with MGD prior to treatment (n=5), subjects with MGD at a first time point post-treatment (MGD FUP 1; n=4), and subjects with MGD at a second time point post-treatment (e.g., a time point following the first time point post-treatment) (MGD FUP 2; n=5). The data shown are the mean±SEM.

Corneal staining was also performed to assess the severity of MGD in the study subjects. These data show that subjects having MGD (prior to treatment) have increased corneal staining compared to control (healthy) subjects, and that subjects having MGD following treatment have a decreased level of corneal staining compared to subjects having MGD prior to treatment (FIG. 19). Subjects having MGD following treatment also had a decrease in the Optical Surface Disease Index (ODSI) score compared to MGD subjects prior to treatment (FIG. 20).

Figure 21:
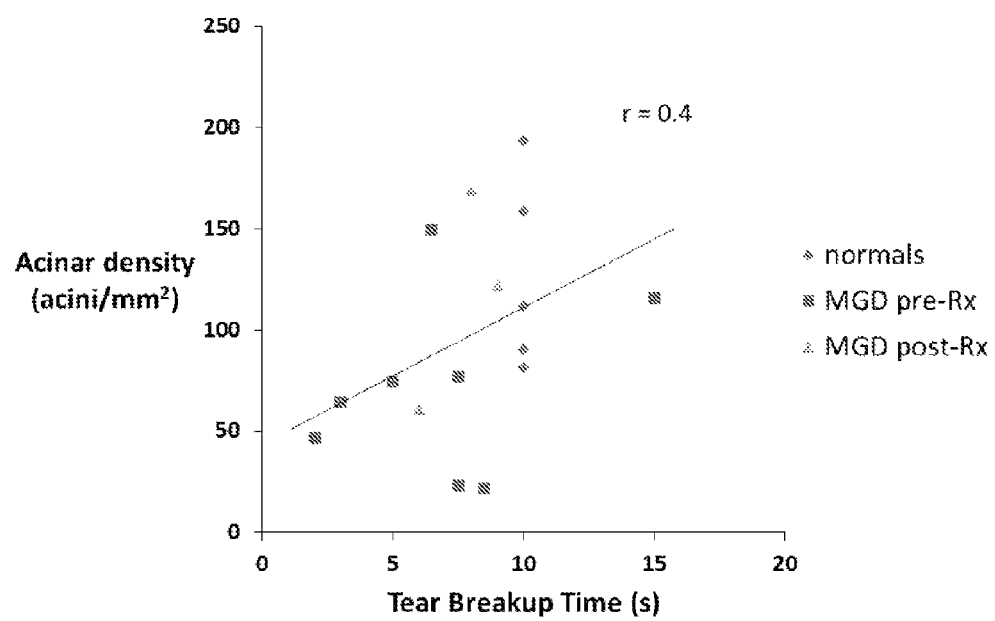
FIG. 21 is a linear regression analysis of the relationship between meibomian gland acinar density (acini/mm$^2$) and tear break-up time (seconds) using data gathered from normal (control) subjects, subjects with MGD prior to treatment (MGD pre-Rx), and subjects with MGD following treatment (MGD post-Rx) (r=0.04).
Figure 22:
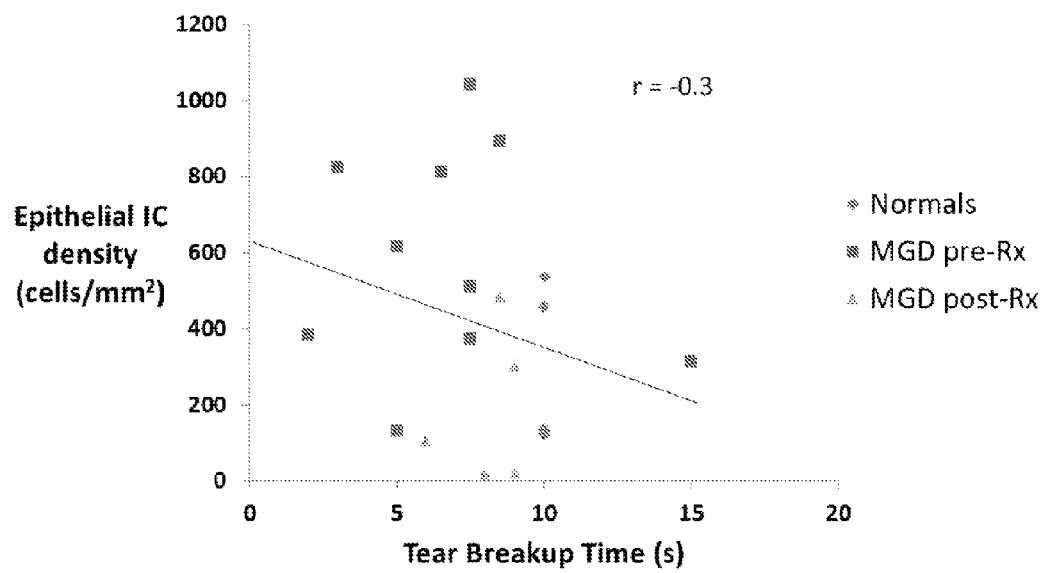
FIG. 22 is a linear regression analysis of the relationship between epithelial immune cell density (cells/mm$^2$) and tear break-up time using data gathered from normal (control) subjects, subjects having MGD prior to treatment (MGD pre-Rx), and subjects having MGD following treatment (MGD post-Rx) (r=−0.3).
Figure 23:
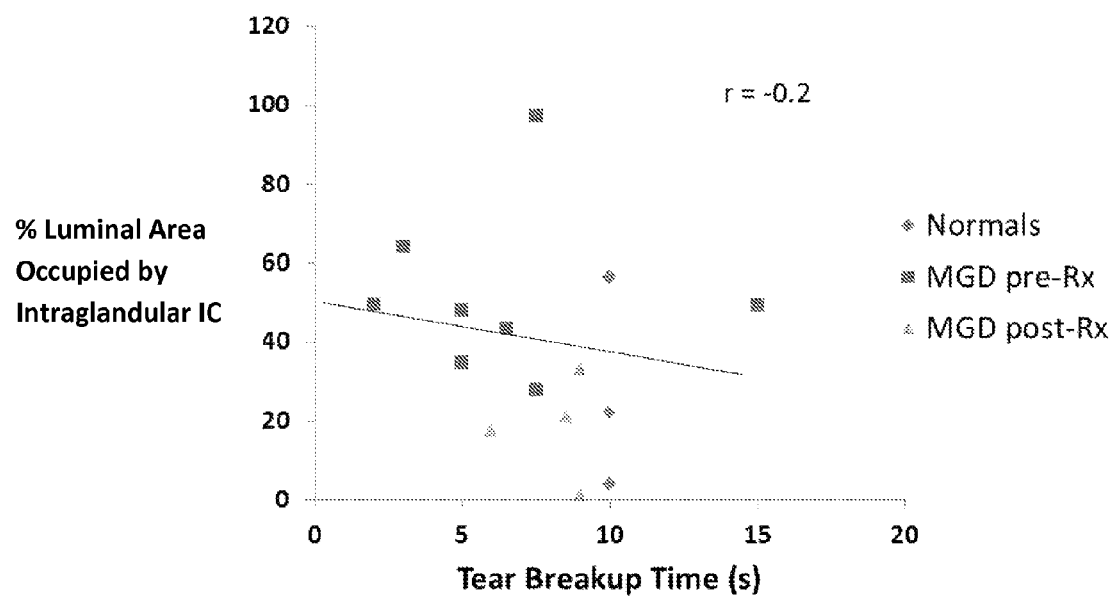
FIG. 23 is a linear regression analysis of the relationship between the percent meibomian gland ductal luminal area occupied by intraglandular immune cells (percentage) and tear break-up time (seconds) using data gathered from normal (control) subjects, subjects having MGD prior to treatment (MGD pre-Rx), and subjects having MGD following treatment (MGD post-Rx) (r=−0.2).
Figure 24:
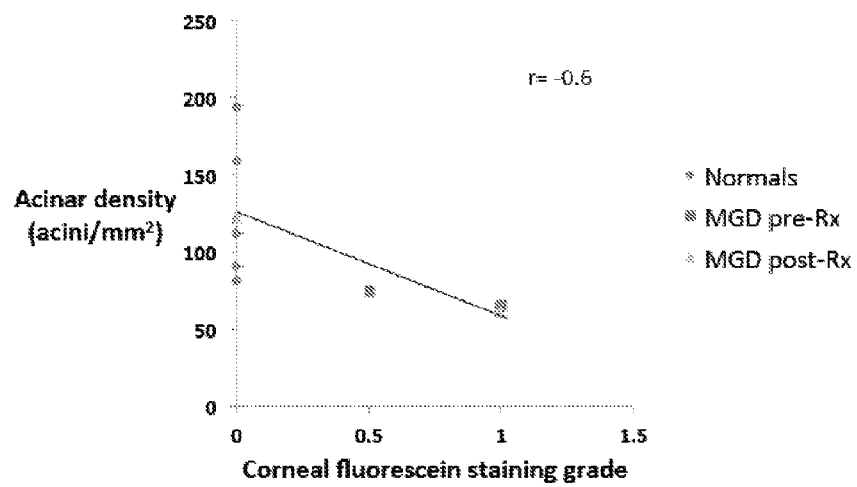
FIG. 24 is a linear regression analysis of the relationship between the meibomian gland acinar density (acini/mm$^2$) and corneal fluorescein staining grade using data gathered from normal (control) subjects, subjects having MGD prior to treatment (MGD pre-Rx), and subjects having MGD following treatment (MGD post-Rx) (r=−0.6).

Linear regression analysis was also performed to compare the eyelid tissue structures determined using in vivo confocal microscopy with other tests of the severity of MGD in a subject. These analyses show that acinar density positively correlates with tear break-up time in the subjects participating in the study (r=0.4) (FIG. 21). In addition, linear regression analysis shows that palpebral conjunctival epithelial immune cell density shows an inverse relationship to tear break-up time in subjects in this study (r=−0.3) (FIG. 22), and the percent luminal area occupied by intraglandular immune cells also shows an inverse relationship to tear break-up time in the subjects in this study (r=−0.2) (FIG. 23). In a separate linear regression analysis, acinar density shows an inverse relationship to corneal fluorescein staining in the subjects in this study (r=−0.6) (FIG. 24).

In sum, the above data show that patients having MGD prior to treatment have an elevation in palpebral conjunctival epithelial inflammation and a decrease in tear break-up time compared to healthy controls (576±86 vs. 278±91 cells/mm$^2$ (p=0.03) and 4.5±2 vs. 10±0 seconds (p=0.004)). Subjects having MGD prior to treatment also show a thicker, more globular acinar epithelium compared to control subjects (19±1 vs. 15±1 μm; p=0.04), an increase in periglandular and intraglandular immune cells compared to healthy controls (4213±1674 μm$^2$ vs. 2335±1013 μm$^2$ (p=0.4), and 55±10 vs. 35±13% (p=0.3), respectively), a decrease in acinar density compared to healthy controls (76±14 vs. 127±21 acini/mm$^2$; p=0.08), and an increase in corneal staining compared to healthy controls (grade 1±0.7 vs. 0; p=0.06).

The data described above further show that subjects having MGD after treatment have a decrease in palpebral conjunctival epithelial, stromal, and intraglandular inflammation compared to subjects having MGD prior to treatment (162±78 vs. 576±86 cells/mm$^2$ (p=0.003), 17±10 vs. 118±42 cells/mm$^2$ (p=0.04), and 19±5 vs. 55±10% (p=0.01), respectively), and an increase in tear break-up time compared to subjects having MGD prior to treatment (8±1 vs. 5±2 seconds (p=0.01)). The data also show a trend towards a decrease in periglandular inflammation and corneal fluorescein staining in subjects having MGD after treatment compared to subjects having MGD prior to treatment (1441±1005 μm$^2$ vs. 4213±1674 μm$^2$ (p=0.2), and 0.6±0.5 vs. 1±0.7 (p=0.2), respectively). In addition, the data show a decrease in OSDI score in subjects having MGD at a later point in treatment as compared to subjects having MGD at an earlier time point in treatment (28±22 vs. 40±13; p=0.3).

The above described linear regression analyses show that tear break-up time correlates positively with acinar density (r=0.4; n=16), and correlates negatively with palpebral conjunctival epithelial and intraglandular inflammation (r=−0.3 (n=20), and r=−0.2 (n=16), respectively) in the subjects in this study. The analyses further show that corneal staining score correlates negatively with acinar density (r=−0.6; n=9).

Example 2

Changes in Eyelid Tissue Structures in MGD Subjects Receiving Treatment

Figure 25:
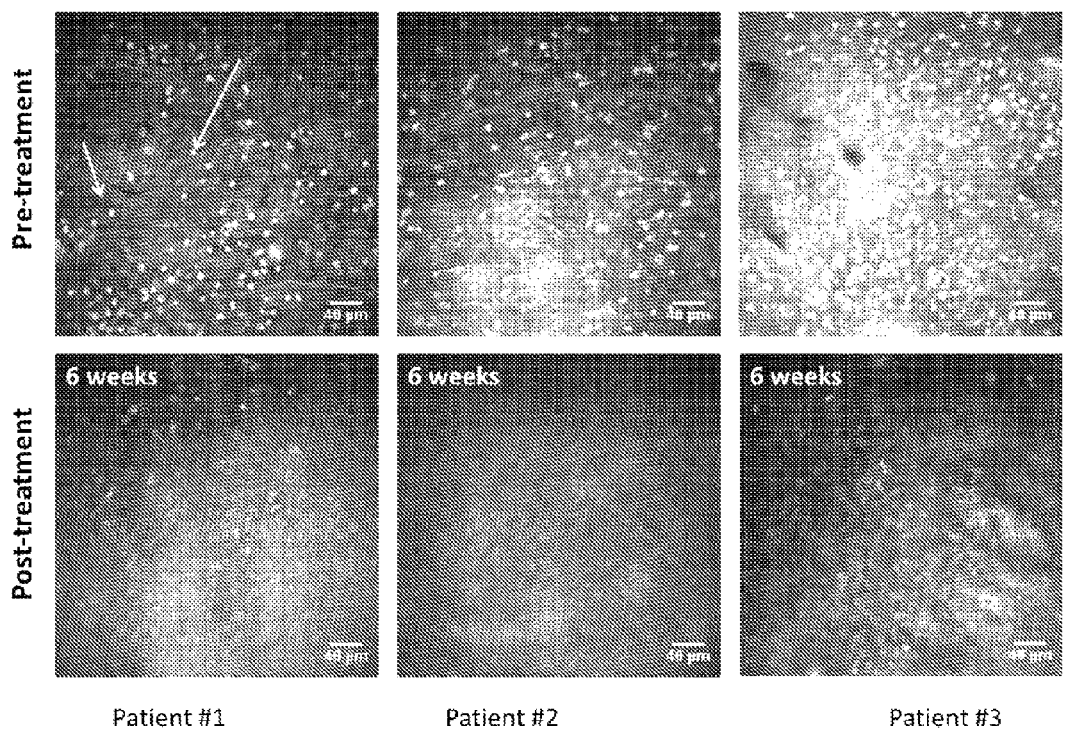
FIG. 25 is a set of six in vivo confocal micrographs of eyelids from three human subjects having MGD (patient #1, left images; patient #2, center images; and patient #3, right images) before treatment (pre-treatment) (top row) or after treatment (6 weeks post-treatment) (bottom row) that show the immune cells present in the palpebral conjunctival epithelium.
Figure 26:
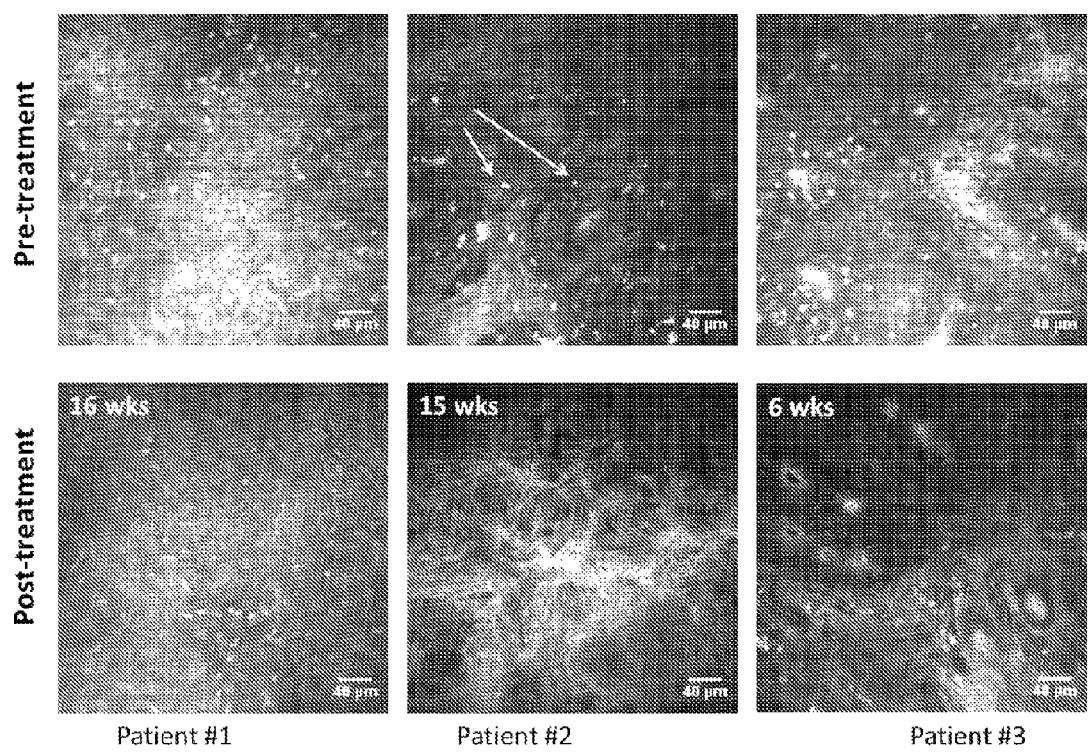
FIG. 26 is a set of six in vivo confocal micrographs of eyelids from three human subjects having MGD (patient #1, left images; patient #2, center images; and patient #3, right images) before treatment (pre-treatment) (top row) or after treatment (16 weeks, 15 weeks, and 6 weeks post-treatment for patient #1, patient #2, and patient #3, respectively) (bottom row) that show the immune cells present in the palpebral conjunctival substantia propria.
Figure 27:
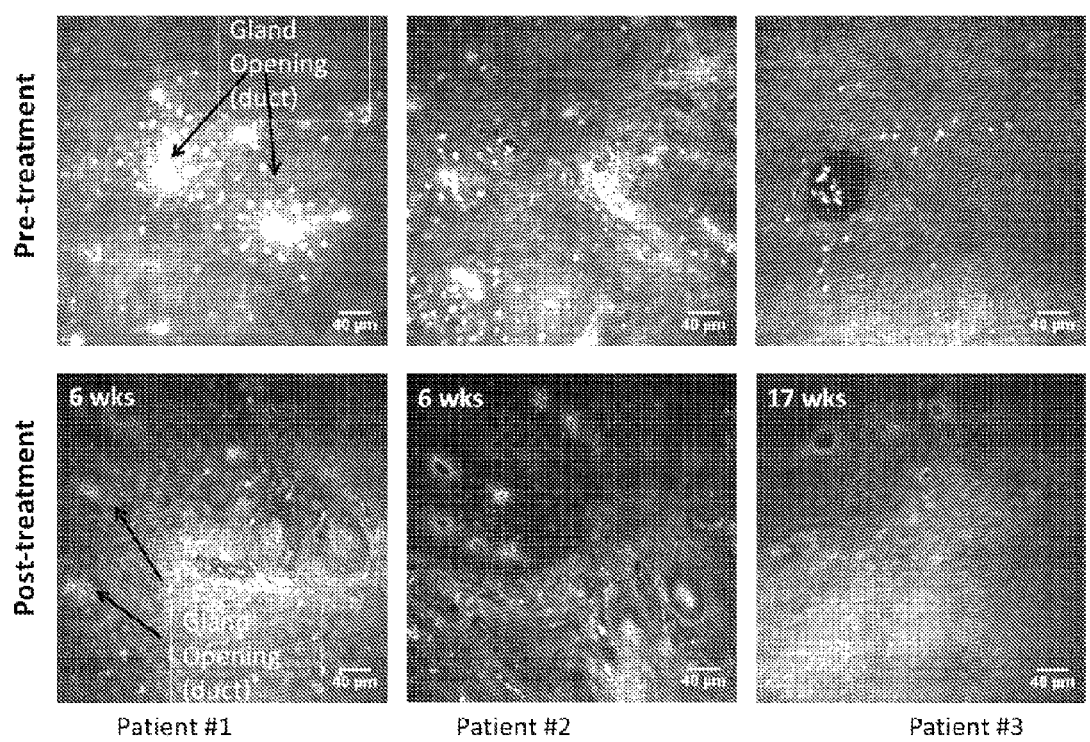
FIG. 27 is a set of six in vivo confocal micrographs of eyelids from three human subjects having MGD (patient #1, left images; patient #2, center images; and patient #3, right images) before treatment (pre-treatment) (top row) or after treatment (6 weeks, 6 weeks, and 17 weeks post-treatment for patient #1, patient #2, and patient #3, respectively) (bottom row) that show the periglandular immune cells (right and center panels) and intraglandular with periglandular immune cells (left panels).
Figure 28:
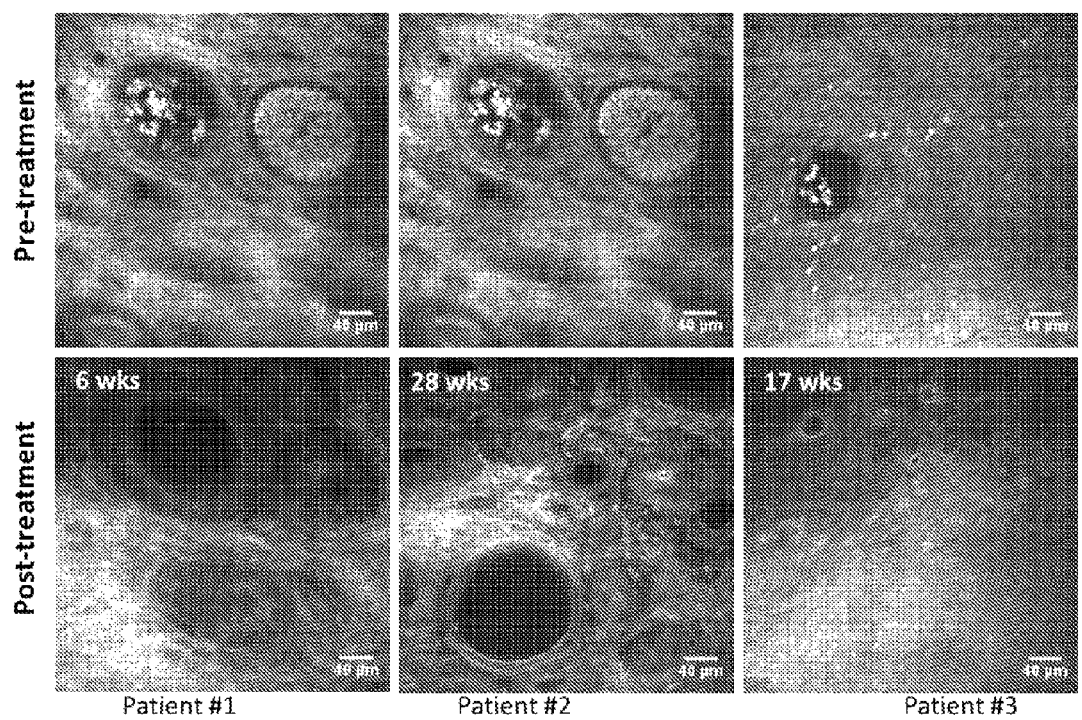
FIG. 28 is a set of six in vivo confocal micrographs of eyelids from three human subjects having MGD (patient #1, left images; patient #2, center images; and patent #3, right images) before treatment (pre-treatment) (top row) or after treatment (6 weeks, 28 weeks, and 17 weeks post-treatment for patient #1, patient #2, and patient #3, respectively) (bottom row) that show the intraglandular (meibomian gland duct) immune cells.
Figure 29:
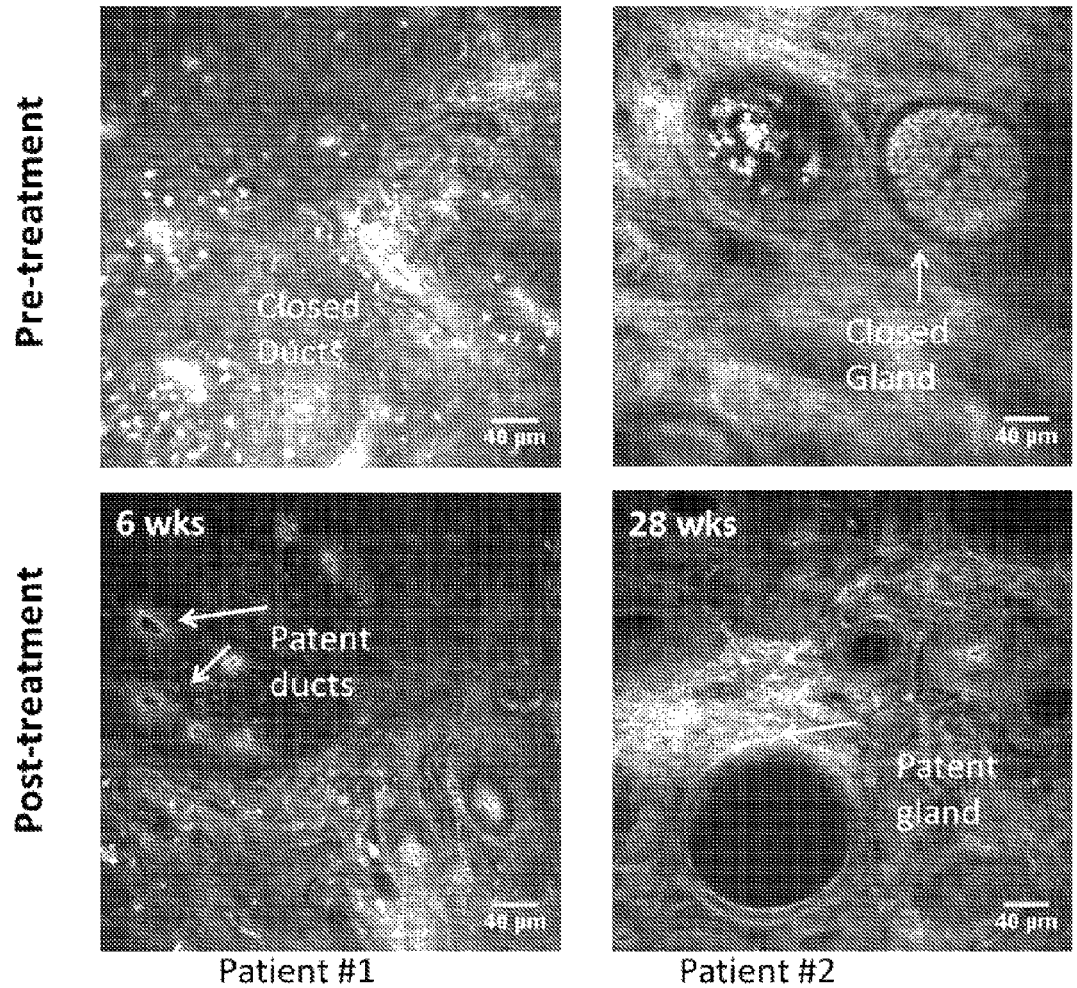
FIG. 29 is a set of four in vivo confocal micrographs of eyelids from two human subjects having MGD (patient #1, left images, and patient #2, left images) before treatment (pre-treatment) (top row) or after treatment (6 weeks and 28 weeks post-treatment for patient #1 and patient #2, respectively) (bottom row) that show the patency of meibomian glands and its ducts.

The changes in the palpebral conjunctival epithelial immune cells, the palpebral conjunctival substantia propria immune cells, the periglandular immune cells, the intraglandular immune cells, and the patency of meibomian glands at a time point following treatment and a time point prior to treatment were determined in three subjects having MGD (patient #1, patient #2, and patient #3). The data show that each patient had a decrease in the number and density of palpebral conjunctival epithelial immune cells following treatment as compared to the number and density of palpebral conjunctival epithelial immune cells present prior to treatment (FIG. 25). A separate set of images shows that each patient had a decrease in the number and density of palpebral conjunctival substantia propria immune cells following treatment compared to the number and density of palpebral conjunctival substantial propria immune cells present prior to treatment (FIG. 26). An additional set of images shows that subjects following treatment had a decrease in the number and density of periglandular immune cells and extent of luminal intraglandular immune cells compared to the number and density of periglandular immune cells and extent of luminal intraglandular immune cells prior to treatment (FIGS. 27 and 28, respectively). Images gathered from subjects #1 and #2 show an increase in the patency of meibomian glands in these subjects following treatment as compared to the patency of meibomian glands in these subjects prior to treatment (FIG. 29).

In sum, these data show that efficacy of treatment of MGD can be determined by assessing changes in the density of acini, thickness of acinar epithelium, the number and/or density of palpebral conjunctival epithelial immune cells, palpebral conjunctival substantia propria immune cells, periglandular immune cells, intraglandular immune cells, the number or presence of obstructed glands and ducts, and the size of gland acini and/or ducts/ductules, wherein one or more of an increase in acinar density, a decrease in acinar epithelial thickness, a decrease in the number and/or density of palpebral conjunctival epithelial immune cells, a decrease in palpebral conjunctival substantia propria immune cells, a decrease in intraglandular immune cells, a decrease in the number or absence of or decreased extent of obstruction of obstructed meibomian glands and ducts, and a decrease in the size of ducts/ductules in the subject at a time point following treatment or at a later time point in treatment compared to an earlier time point (e.g., a time point prior to treatment) indicate successful treatment of MGD in a subject.

Figure 30:
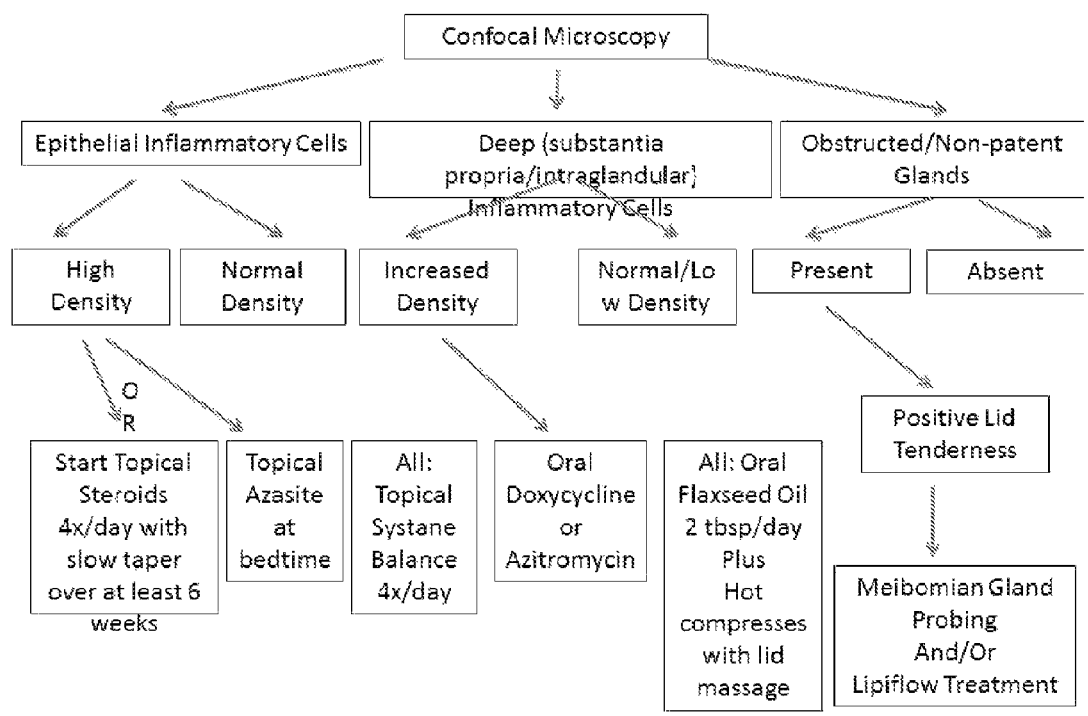
FIG. 30 is a flow chart showing the therapeutic treatments provided herein that include the selective administration of one or more therapeutic agents to a subject having MGD on the basis of the number and/or density of epithelial immune cells, the number and/or density of deep immune cells (e.g., intraglandular immune cells or immune cells present in the palpebral substantia propria), and/or the presence, number, extent, and/or percentage of obstructed or non-patent meibomian glands present in the eyelid of a subject as compared to a corresponding reference value. The therapeutic treatments shown can be cumulative (e.g., a subject having an elevated or "high" number and/or density of epithelial immune cells in the eyelid and an elevated or "increased" density of intraglandular immune cells (as compared to corresponding reference values) can be administered a topical steroid or topical azasite, and orally administered an anti-inflammatory antibiotic (e.g., doxycycline or azithromycin).

In view of the data above, new methods for treating a subject (e.g., a subject having MGD) are provided herein (see, e.g., FIG. 30). For example, a subject having an increased number and/or density of palpebral conjunctival epithelial immune cells in the eyelid can be treated with a topical steroid (e.g., four times a day) or a topical antibiotic (e.g., azasite), a subject having an increased number and/or density of palpebral conjunctival substantia propria or intraglandular immune cells can be systemically treated (orally administered) or topically treated (ocularly administered) with an anti-inflammatory antibiotic (e.g., doxycycline or azithromycin), and a subject having an obstructed, non-patent gland can be treated with meibomian gland probing and/or Lipiflow® treatment. Any of the treatments listed in FIG. 30 can be used in any combination. For example, a subject having a high density of epithelial immune cells, and an increased density of immune cells in the substantia propria or an increased number of intraglandular immune cells can be treated with a combination of (i) a topical steroid or a topical antibiotic, and (ii) a systemically administered (orally administered) or topically administered (ocularly administered) an anti-inflammatory antibiotic. FIG. 30 also indicates that all subjects having MGD can be treated with topical systane, oral flaxseed oil, and/or hot compresses with eyelid massage. The methods of treatment herein can also include further administration of one or more additional therapeutic agents, and therefore, the treatments listed in FIG. 30 are not limiting or exclusive.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of diagnosing and treating meibomian gland dysfunction (MGD) in a subject, the method comprising:
   (a) determining in an eyelid of a subject one or more of: (i) a number and/or density of immune cells present within one or more ducts/ductules in one or more meibomian gland(s), (ii) a level of glandular/ductal obstruction in one or more meibomian gland(s), and (iii) a size of one or more ducts/ductules present in one or more meibomian gland(s);
   (b) comparing the one or more of: (i) the number and/or density of immune cells present within one or more ducts/ductules in one or more meibomian gland(s), (ii) the level of glandular/ductal obstruction in one or more meibomian gland(s), and (iii) the size of one or more ducts/ductules present in one or more meibomian gland(s), determined in the eyelid of the subject to one or more corresponding reference values;
   (c) identifying a subject having in an eyelid one or more of: (i) an elevation in the number and/or density of immune cells present within one or more ducts/ductules in one or more meibomian gland(s), (ii) an elevation in the level of glandular/ductal obstruction in one or more meibomian gland(s), and (iii) an elevation in the size of one or more ducts/ductules present in one or more meibomian gland(s), compared to the one or more corresponding reference values, as having MGD;
   (d) determining the number and/or density of immune cells in a palpebral conjunctival epithelium, and/or a number and/or density of immune cells in a palpebral conjunctival substantia propria in the eyelid of the subject;
   (e) comparing the number and/or density of immune cells in the palpebral conjunctival epithelium, and/or the number and/or density of immune cells in the palpebral conjunctival substantia propria determined in the eyelid of the subject, to one or more corresponding reference values;
   (f) further identifying a subject having in an eyelid one or more of an elevation in the number and/or density of immune cells in the palpebral conjunctival epithelium, and an elevation in the number and/or density of immune cells in the palpebral conjunctival substantia propria, compared to the one or more corresponding reference values, as having MGD; and
   (g) selectively orally or topically administering to a subject identified as having MGD and determined to have an elevated number and/or density of immune cells in the palpebral conjunctival substantia propria as compared to a reference level, at least one anti-inflammatory antimicrobial agent, and/or
   selectively performing meibomian gland probing on a subject identified as having MGD and determined to have an elevation in the level of glandular/ductal obstruction in one or more meibomian gland(s) compared to a reference level.

2. The method of claim 1, wherein the determining in (a) is performed using in vivo confocal microscopy.

3. The method of claim 1, wherein the determining in (d) is performed using in vivo confocal microscopy.

4. The method of claim 1, wherein one or more of the reference values are threshold values.

5. The method of claim 1, wherein one or more of the reference values is selected from the group consisting of: (i) the number and/or density of immune cells present within one or more ducts/ductules in one or more meibomian gland(s), (ii) the level of glandular/ductal obstruction in one or more meibomian gland(s), and (iii) the size of one or more ducts/ductules present in one or more meibomian gland(s), determined in an eyelid of a healthy subject.

6. A method comprising using in vivo confocal microscopy to determine in an eyelid of a subject one or both of:
   (i) a number and/or density of immune cells present within one or more ducts/ductules in one or more meibomian gland(s), and
   (ii) a size of one or more ducts/ductules present in one or more meibomian gland(s).

* * * * *